(12) United States Patent
Chan Chun Kong et al.

(10) Patent No.: US 8,076,349 B2
(45) Date of Patent: Dec. 13, 2011

(54) SPIROTROPANE COMPOUNDS AND METHODS FOR THE MODULATION OF CHEMOKINE RECEPTOR ACTIVITY

(75) Inventors: Laval Chan Chun Kong, Kirkland (CA); Christophe Moinet, Laval (CA); Marc Courchesne, Laval (CA); Louis Vaillancourt, Mascouche (CA); Monica Bubenik, Montreal (CA)

(73) Assignee: Virochem Pharma Inc., Quebec (CA)

( * ) Notice: Subject to any disclaimer, the term of this patent is extended or adjusted under 35 U.S.C. 154(b) by 917 days.

(21) Appl. No.: 11/792,577

(22) PCT Filed: Dec. 9, 2005

(86) PCT No.: PCT/CA2005/001877
§ 371 (c)(1), (2), (4) Date: Apr. 9, 2008

(87) PCT Pub. No.: WO2006/060918
PCT Pub. Date: Jun. 15, 2006

(65) Prior Publication Data
US 2009/0047238 A1 Feb. 19, 2009

Related U.S. Application Data

(60) Provisional application No. 60/634,257, filed on Dec. 9, 2004.

(51) Int. Cl.
*A61K 31/439* (2006.01)
*A61K 31/4709* (2006.01)
*C07D 471/18* (2006.01)

(52) U.S. Cl. ............. 514/278; 546/18; 546/20; 548/408

(58) Field of Classification Search .................. 514/278; 546/18, 20; 548/408
See application file for complete search history.

(56) References Cited

U.S. PATENT DOCUMENTS

| 5,407,938 | A | 4/1995 | Fisher et al. |
| 5,534,520 | A | 7/1996 | Fisher et al. |
| 5,852,029 | A | 12/1998 | Fisher et al. |

FOREIGN PATENT DOCUMENTS

| CA | 2310458 | | 6/1999 |
| WO | WO 95/03303 | A2 | 2/1995 |
| WO | WO 01/66546 | | 9/2001 |
| WO | WO 01/66546 | A1 * | 9/2001 |
| WO | WO 02/13824 | A1 | 2/2002 |
| WO | WO 2004/041279 | A1 | 5/2004 |
| WO | WO 2005/007656 | A1 | 1/2005 |
| WO | WO 2005/023809 | | 3/2005 |
| WO | WO 2005/023810 | A1 | 3/2005 |
| WO | WO 2005/000096 | | 1/2006 |
| WO | WO 2006/060919 | A1 | 6/2006 |
| WO | WO 2007/143847 | A1 | 12/2007 |

OTHER PUBLICATIONS

Dr. Rolf Eberbard Nitz, et al., Arzneimittel-Forschung, Jul. 1955, pp. 357-364.
Por A. Garcia Sacristan, et al., Arch. De Farmacol y Toxicol, 1977, pp. 57-66.
George W. Smith, et al., Journal of the American Chemical Society, Jul. 5, 1955, pp. 3541-3543.
International Preliminary Report on Patentability for International Application No. PCT/CA2005/001877 issued Jun. 13, 2007.
Written Opinion of the International Searching Authority for International Patent Application No. PCT/CA2005/001877 completed Mar. 15, 2006.
International Search Report for PCT/CA2005/001877 mailed Mar. 29, 2006.
Abstract of WO2001066546, Date: Sep. 13, 2001.
CAPLUS 77699151, Date: Oct. 26, 2010.
CAPLUS 72402245, Date: Oct. 26, 2010.
CAPLUS 64192796, Date: Oct. 26, 2010.
CAPLUS 64192774, Date: Oct. 26, 2010.
Abstract of Dr. Rolf Eberbard Nitz, et al., "Chemistry and anticonvulsive activity of new hydantoin derivatives" CAPLUS Accession No: 1956:2309 Copyright © 2008 ACS on SciFinder®.
Abstract of Por A. Garcia Sacristan, et al., "N-substituted nortropane hydantoins. Action on smooth muscle, and antiarrhythmic and anticonvulsant effects" Accession No. 1977:593826 CAPLUS Copyright © 2008 ACS on SciFinder®.
Dr. Rolf Eberbard Nitz, et al., Arzneimittel-Forschung, pp. 357-364, Jul. 1955.
Por A. Garcia Sacristan, et al., Arch. De. Farmacol y Toxicol, 1977, pp. 57-66.
International Search Report for International Application No. PCT/CA2007/001062 mailed Sep. 6, 2007.
International Search Report for International Application No. PCT/CA2005/001878 mailed Mar. 29, 2006.
Supplementary European Search Report for European Application No. 05 81 9431.7-2117 / 1831222 of Sep. 18, 2009.
Written Opinion of the International Searching Authority for International Application No. PCT/CA2005/001877 mailed Mar. 29, 2006.
Extended European Search Report in European Application No. 05 819 950.6-2101 / 1824853 dated Oct. 5, 2010.
International Search Report for International Application No. PCT/CA2005/001877 mailed Mar. 29, 2006.
International Search Report dated Jun. 21, 2007 corresponding to International Application PCT/CA2005/001877.

* cited by examiner

*Primary Examiner* — Susannah Chung
(74) *Attorney, Agent, or Firm* — Millen, White, Zelano & Branigan, P.C.

(57) ABSTRACT

Compounds according to formula (I):

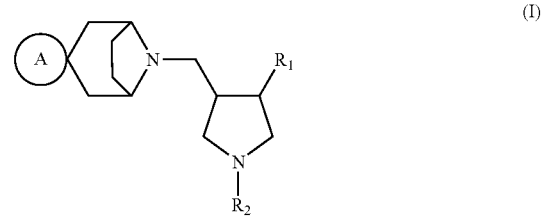

(I)

wherein A, $R_1$ and $R_2$ are as defined herein, and the pharmaceutically acceptable salts, hydrates and solvates thereof are useful for the modulation of CCR5 chemokine receptor activity.

19 Claims, No Drawings

SPIROTROPANE COMPOUNDS AND METHODS FOR THE MODULATION OF CHEMOKINE RECEPTOR ACTIVITY

The application claims the benefit of U.S. Ser. No. 60/634,257 filed on Dec. 9, 2004 which is herein incorporated by reference.

FIELD OF THE INVENTION

The present invention relates to novel spirotropane compounds and a method of modulating chemokine receptor activity using these compounds. The present invention is also directed to novel spirotropane compounds which are useful in the prevention or treatment of diseases associated with the modulation of CCR5 chemokine receptor activity. The present invention is further directed to a method of blocking cellular entry of HIV in a subject and to compositions using these compounds.

BACKGROUND OF THE INVENTION

Chemokines are chemotactic cytokines that are released by a wide variety of cells to attract macrophages, T cells, eosinophils, basophils and neutrophils to sites of inflammation and they also play a role in the maturation of cells of the immune system. Chemokines play an important role in immune and inflammatory responses in various diseases and disorders, including asthma, rhinitis and allergic diseases, as well as autoimmune pathologies such as rheumatoid arthritis and atherosclerosis. Chemokines are small 70 to 80 amino acid proteins with well-characterized three-dimensional structures, usually stabilized by two disulfide bridges. They are divided into four families on the basis of pattern of conserved cysteine residues.

Chemokine receptors have been designated such as, CCR1, CCR2, CCR2A, CCR2B, CCR3, CCR4, CCR5, CCR6, CCR7, CCR8, CCR9, CCR10, CXCR1, CXCR2, CXCR3, and CXCR4 and therefore agents which modulate these receptors may be useful in the prevention and treatment of diseases as mentioned above.

One of them, the C—C chemokines family, includes potent chemoattractants of monocytes and lymphocytes such as RANTES (Regulated on Activation, Normal T Expressed and Secreted), eotaxin, MIP-1α and MIP-1β (Macrophage Inflammatory Proteins) and human monocyte chemotactic proteins 1-3 (MCP-1, MCP-2 and MCP-3). More specifically, C—C chemokine receptor 5 (CCR5), a β-chemokine receptor with a seven-transmembrane-protein structure, was found to serve as a coreceptor for non-syncytium-inducing or macrophage-tropic HIV-1 (R5 viruses). It was also established that CCR5 is the principal chemokine receptor required for the entry of HIV into the cell during primary infection. Therefore, interfering with the interaction between the viral receptor CCR5 and HIV can block HIV entry into the cell. It would therefore be useful to provide novel compounds which are modulators of chemokine receptor activity.

SUMMARY OF THE INVENTION

In one aspect, the present invention provides novel compounds represented by formula (I):

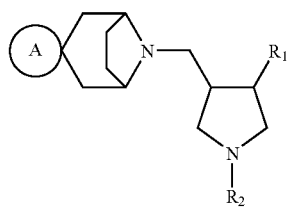

(I)

or pharmaceutically acceptable salts, hydrates or solvates thereof, wherein

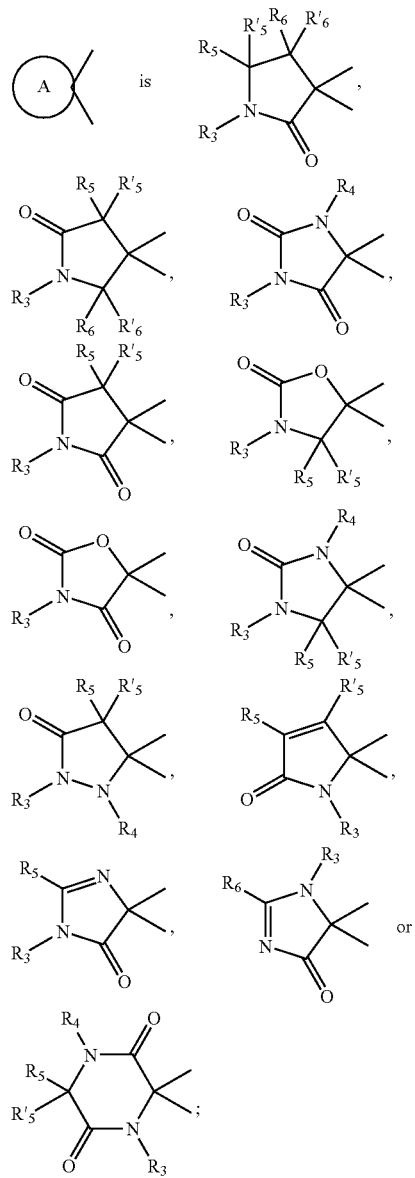

$R_1$ is optionally substituted $C_{1-10}$ alkyl, optionally substituted $C_{2-10}$ alkenyl (e.g. $C_{2-6}$ alkenyl), optionally substituted $C_{2-10}$ alkynyl (e.g. $C_{2-6}$ alkynyl), optionally substituted $C_{6-12}$ aryl, optionally substituted 3 to 10 membered heterocycle, optionally substituted $C_{7-12}$ aralkyl or optionally substituted heteroaralkyl (e.g., wherein the heterocycle portion has 3 to 10 members and the alkyl portion has 1 to 6 carbon atoms);

$R_2$ is H,

(II)

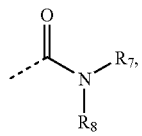

(III)

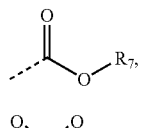

(IV)

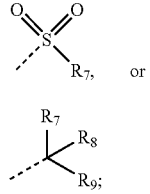

(V)

R_7, or (VI)

$R_3$, $R_4$, $R_5$, $R'_5$, $R_6$ and $R'_6$ are each, independently, H, optionally substituted $C_{1-10}$ alkyl, optionally substituted $C_{2-10}$ alkenyl (e.g. $C_{2-6}$ alkenyl), optionally substituted $C_{2-10}$ alkynyl (e.g. $C_{2-6}$ alkynyl), optionally substituted $C_{6-12}$ aryl, optionally substituted 3 to 10 membered heterocycle, optionally substituted $C_{7-12}$ aralkyl or optionally substituted heteroaralkyl (e.g., wherein the heterocycle portion has 3 to 10 members and the alkyl portion has 1 to 6 carbon atoms);

$R_7$ is H, optionally substituted $C_{1-10}$ alkyl, optionally substituted $C_{2-10}$ alkenyl (e.g. $C_{2-6}$ alkenyl), optionally substituted $C_{2-10}$ alkynyl (e.g. $C_{2-6}$ alkynyl), optionally substituted $C_{6-12}$ aryl, optionally substituted 3 to 10 membered heterocycle, or optionally substituted heteroaralkyl (e.g., wherein the heterocycle portion has 3 to 10 members and the alkyl portion has 1 to 6 carbon atoms);

$R_8$ is H or optionally substituted $C_{1-10}$ alkyl, optionally substituted $C_{2-10}$ alkenyl (e.g. $C_{2-6}$ alkenyl), or optionally substituted $C_{2-10}$ alkynyl (e.g. $C_{2-6}$ alkynyl), or $R_7$ and $R_8$ can be taken together to form an optionally substituted 3 to 10 membered heterocycle; and $R_9$ is H or optionally substituted $C_{1-10}$ alkyl.

In another aspect, there is provided a method of modulating chemokine receptor activity in a subject comprising administering to the subject an effective amount of a compound of formula (I) or composition of the invention.

In still another aspect, there is provided a method for prevention or treatment of certain inflammatory diseases, immunoregulatory diseases, organ transplantation reactions and in the prevention and treatment of infectious diseases such as HIV infections in a subject in need of such treatment comprising administering to the subject a therapeutically effective amount of a compound of formula (I) or composition of the invention.

In still another aspect, there is provided a method for the prevention or treatment of diseases associated with the modulation of CCR5 chemokine receptor activity in a subject in need of such treatment comprising administering to the subject a therapeutically effective amount of a compound of formula (I) or composition of the invention.

In still another aspect, there is provided a method for blocking cellular entry of HIV in a subject comprising administering to the subject in need thereof an effective amount of a compound of formula (I) or composition of the invention to block HIV from cellular entry in said subject.

In still another aspect, there is provided a method for the prevention or treatment of diseases associated with the modulation of chemokine receptor activity in a subject in need of such treatment comprising administering to the subject a pharmaceutical combination comprising at least one compound of formula (I) and at least one further therapeutic agent.

In another aspect, there is provided a pharmaceutical formulation comprising the compound of the invention in combination with a pharmaceutically acceptable carrier or excipient.

In another aspect of the invention is the use of a compound according to formula (I), for the manufacture of a medicament for the prevention or treatment of diseases associated with the modulation of chemokine receptor activity.

DETAILED DESCRIPTION OF THE INVENTION

In one embodiment, compounds of the present invention comprise those wherein the following embodiments are present, either independently or in combination.

In one embodiment, the present invention provides novel compounds represented by formula I:

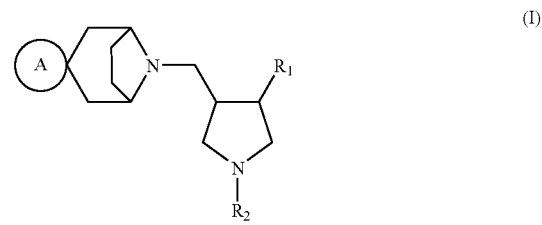

(I)

or pharmaceutically acceptable salts, hydrates or solvates thereof wherein A, $R_1$ and $R_2$ are defined above.

In one embodiment, the present invention provides novel compounds represented by formula (Ia):

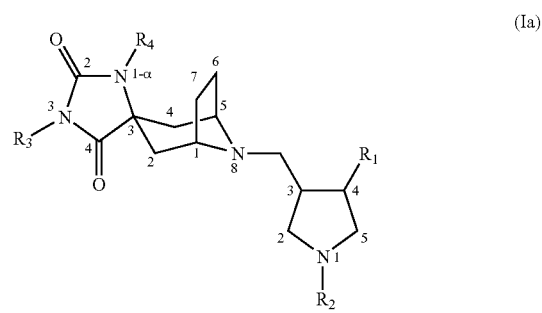

(Ia)

or pharmaceutically acceptable salts, hydrates or solvates thereof wherein $R_1$, $R_2$, $R_3$ and $R_4$ are defined above.

In one embodiment, the present invention provides novel compounds represented by formula (Ib):

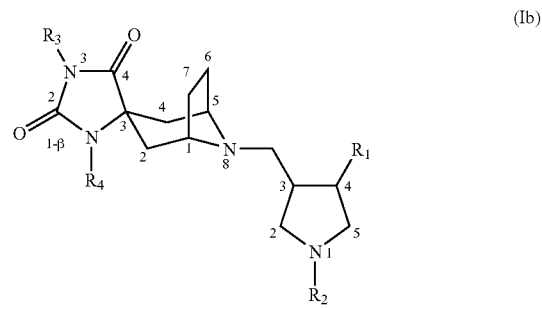

(Ib)

or pharmaceutically acceptable salts, hydrates or solvates thereof wherein $R_1$, $R_2$, $R_3$ and $R_4$ are defined above.

In one embodiment, the present invention provides novel compounds represented by formula (Ic):

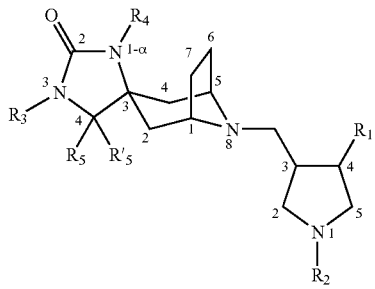

(Ic)

or pharmaceutically acceptable salts, hydrates or solvates thereof wherein $R_1$, $R_2$, $R_3$, $R_4$, $R_5$ and $R'_5$ are defined above.

In one embodiment, the present invention provides novel compounds represented by formula (Id):

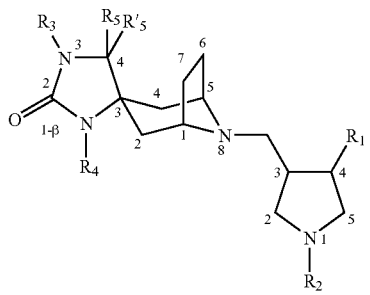

(Id)

or pharmaceutically acceptable salts, hydrates or solvates thereof wherein $R_1$, $R_2$, $R_3$, $R_4$, $R_5$ and $R'_5$ are defined above In one embodiment, the compounds of the present invention are represented by formula (I):

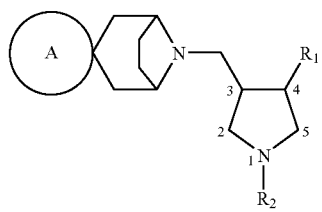

(I)

or pharmaceutically acceptable salts, hydrates or solvates thereof wherein A, $R_1$ and $R_2$ are defined above.

In one embodiment, the compounds of the present invention are in the (3R,4R)-diastereomer;

In one embodiment, the compounds of the present invention are in the (3S,4R)-diastereomer;

In one embodiment, the compounds of the present invention are in the (3R,4S)-diastereomer;

In one embodiment, the compounds of the present invention are in the (3S,4S)-diastereomer.

In a further embodiment, $R_1$ is chosen from a $C_{6-12}$ aryl, or 3-10 member heterocycle which in each case are optionally substituted.

In a further embodiment, $R_1$ is a $C_{6-12}$ aryl, or a 3-6 member heterocycle which in each case are optionally substituted.

In a further embodiment, $R_1$ is $C_{6-12}$ aryl.

In a further embodiment, $R_1$ is an aryl chosen from phenyl, indenyl, naphthyl and biphenyl which in each case are optionally substituted.

In a further embodiment, $R_1$ is unsubstituted phenyl or phenyl substituted with at least one substituent chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, $NR_{63}R_{64}$, $C(O)OR_{62}$, cyano, azido, amidino and guanido;

wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

In a further embodiment, $R_1$ is unsubstituted phenyl or phenyl substituted with at least one substituent chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-12 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_1$ is unsubstituted phenyl or phenyl substituted with at least one substituent chosen from halogen, $C_{1-6}$ alkyl, $NR_{63}R_{64}$, nitro, $CONR_{63}R_{64}$, $C(O)OC_{1-6}$ alkyl, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_1$ is unsubstituted phenyl or phenyl substituted with at least one substituent chosen from a halogen, $C_{1-6}$ alkyl, $C_{1-6}$ alkyloxy, $CF_3$, $COOH$, $COOC_{1-6}$ alkyl, cyano, $NH_2$, nitro, $NH(C_{1-6}$ alkyl), $N(C_{1-6}$ alkyl)$_2$ and a 3-8 member heterocycle.

In a further embodiment, $R_1$ is chosen from thienyl, furanyl, pyridyl, oxazolyl, thiazolyl, pyrrolyl, benzofuranyl, indolyl, benzoxazolyl, benzothienyl, benzothiazolyl and quinolinyl, any of which can be unsubstituted or substituted by at least one substituent chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, $NR_{63}R_{64}$, $C(O)OR_{62}$, cyano, azido, amidino and guanido;

wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

In a further embodiment, $R_1$ is chosen from thienyl, furanyl, pyridyl, oxazolyl, thiazolyl, pyrrolyl, benzofuranyl, indolyl, benzoxazolyl, benzothienyl, benzothiazolyl and quinolinyl, any of which can be unsubstituted or substituted by at least one substituent chosen from $C_{1-6}$ alkyl, amino, halogen, nitro, amido, CN, $COOC_{1-6}$ alkyl, $C_{1-6}$ alkyloxy.

In a further embodiment, $R_1$ is chosen from pyridinyl, thiophenyl, benzofuran, thiazole, and pyrazole, any of which can be unsubstituted or substituted with at least one substituent chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl$)_2$ and a 3-8 member heterocycle.

In a further embodiment, $R_2$ is H,

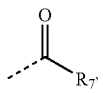  (II)

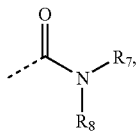  (III)

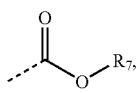  (IV)

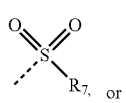  (V)

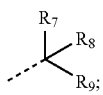  (VI)

In a further embodiment, $R_2$ is H,

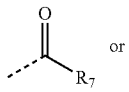  (II) or

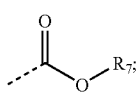  (IV)

In a further embodiment, $R_2$ is:

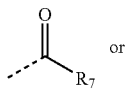  (II) or

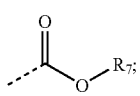  (IV)

In a further embodiment, $R_2$ is:

  (II)

In a further embodiment, $R_2$ is:

  (II)

wherein:
$R_7$ is 4,4-difluorocyclohexyl; or
$R_7$ is $CH_2$-cyclopropyl.

In a further embodiment, $R_2$ is:

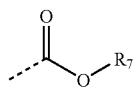  (IV)

wherein $R_7$ is tert-butyl.

$R_7$ is H, optionally substituted $C_{1-10}$ alkyl, optionally substituted $C_{2-10}$ alkenyl, optionally substituted $C_{2-10}$ alkynyl, optionally substituted $C_{6-12}$ aryl, optionally substituted $C_{7-12}$ aralkyl, optionally substituted 3 to 10 membered heterocycle, or optionally substituted heteroaralkyl (e.g., wherein the heterocycle portion has 3 to 10 members and the alkyl portion has 1 to 6 carbon atoms).

$R_7$ is $C_{1-10}$ alkyl, $C_{2-10}$ alkenyl, 3 to 10 membered heterocycle, or heteroaralkyl (e.g., wherein the heterocycle portion has 3 to 10 members and the alkyl portion has 1 to 6 carbon atoms) which in each case are optionally substituted.

$R_7$ is optionally substituted $C_{7-12}$ aralkyl.

$R_7$ is 3 to 10 membered heterocycle or 4-16 member heteroaralkyl any of which can be unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, $NR_{63}R_{64}$, $C(O)OR_{62}$, cyano, azido, amidino and guanido;

wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

$R_7$ is 3 to 10 membered heterocycle or 4-16 member heteroaralkyl any of which can be unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

$R_7$ is 3 to 10 membered heterocycle or 4-16 member heteroaralkyl any of which can be unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

$R_7$ is 3 to 10 membered heterocycle or 4-16 member heteroaralkyl any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido.

$R_7$ is azetidinyl, pyrrolidinyl, piperazinyl, piperidyl, piperidino, oxetanyl, tetrahydropyranyl, tetrahydrofuranyl, morpholinyl, $CH_2$-azetidinyl, $CH_2$-pyrrolidinyl, $CH_2$-piperazinyl, $CH_2$-piperidyl, $CH_2$-oxetanyl, $CH_2$-tetrahydropyranyl, $CH_2$-tetrahydrofuranyl, $CH_2$-morpholinyl any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido.

$R_7$ is H, optionally substituted $C_{1-10}$ alkyl, optionally substituted $C_{2-10}$ alkenyl, optionally substituted $C_{2-10}$ alkynyl.

In accordance with a further aspect of the invention, $R_7$ is optionally substituted $C_{1-12}$ alkyl (e.g., methyl, ethyl, isopropyl, cyclopropyl, cyclobutyl, tert-butyl, cyclopentyl, cyclohexyl, or cycloheptyl, especially cyclohexyl).

In a further embodiment, $R_7$ is $C_{1-12}$ alkyl optionally substituted.

In a further embodiment, $R_7$ is $C_{3-12}$ cycloalkyl optionally substituted.

In a further embodiment, $R_7$ is $C_{3-10}$ cycloalkyl optionally substituted.

In a further embodiment, $R_7$ is $C_{5-7}$ cycloalkyl optionally substituted.

In one embodiment, $R_7$ is optionally substituted $C_{6-7}$ cycloalkyl.

In one embodiment, $R_7$ is optionally substituted $C_6$ cycloalkyl.

In a further embodiment, $R_7$ is $C_{1-12}$ alkyl unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino and guanido;

wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

In a further embodiment, $R_7$ is $C_{1-12}$ alkyl unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_7$ is $C_{1-12}$ alkyl unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_7$ is $C_{3-12}$ cycloalkyl unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino, and guanido;

wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

In a further embodiment, $R_7$ is $C_{3-12}$ cycloalkyl unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_7$ is $C_{3-12}$ cycloalkyl unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl;

or $R_{63}$ and $R_{64}$ are taken together with the nitrogen to form a 3 to 10 member heterocycle.

In a further embodiment, $R_7$ is chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which can be unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-member heteroaralkyl, hydroxyl, oxo, oxime, $NR_{63}R_{64}$, $C(O)OR_{62}$, cyano, azido, amidino, and guanido;

wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

In a further embodiment, $R_7$ is chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which can be unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_7$ is chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl any of which can be unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl;

or $R_{63}$ and $R_{64}$ are taken together with the nitrogen to form a 3 to 10 member heterocycle.

In a further embodiment, $R_7$ is cyclohexyl, cyclopentyl or cyclobutyl unsubstituted or substituted by one or more substituents independently chosen from halogen, nitro, nitroso, $SO_3Rf$, $SO_2Rf$, $PO_3R_{65}R_{66}$, $CONRgRh$, $C_{1-6}$ alkyl, $C_{7-18}$ aralkyl, $C_{6-12}$ aryl, $C_{1-6}$ alkyloxy, $C_{6-12}$ aryloxy, $C(O)C_{1-6}$ alkyl, $C(O)C_{6-12}$ aryl, $C(O)C_{7-12}$ aralkyl, $C(O)NHRf$, 3-10 member heterocycle, 4-16 member heteroaralkyl, hydroxyl, oxo, oxime, $NRgRh$, $C(O)ORf$, cyano, azido, amidino and guanido;

wherein Rf, $R_{65}$, $R_{66}$, Rg and Rh in each case are independently H, $C_{1-6}$ alkyl, $C_{2-6}$ alkenyl, $C_{2-6}$ alkynyl, $C_{6-12}$ aryl, 3-10 member heterocycle, 4-16 member heteroaralkyl, or $C_{7-18}$ aralkyl.

In still a further embodiment, $R_7$ is cyclohexyl, cyclopentyl or cyclobutyl unsubstituted or substituted by one or more substituents chosen from halogen, $SO_2Rf$, $CONRgRh$, $C_{1-6}$ alkyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{6-12}$ aryl, $C(O)C_{7-12}$ aralkyl, $C(O)NHRf$, 3-10 member heterocycle, 4-16 member heteroaralkyl, hydroxyl, oxo, oxime, $NRgRh$, $C(O)ORf$, cyano and azido;

wherein Rf, Rg and Rh in each case are independently H, $C_{1-6}$ alkyl, $C_{6-12}$ aryl, 3-10 member heterocycle, 4-16 member heteroaralkyl, $C_{7-18}$ aralkyl.

In one embodiment, $R_7$ is cyclohexyl, cyclopentyl or cyclobutyl unsubstituted or substituted by one or more substituents independently chosen from $C_{1-6}$ alkyl, halogen, $C_{2-6}$ alkenyl, $C_{2-6}$ alkynyl, $C_{1-6}$ alkyloxy, $C_{2-6}$ alkenyloxy and $C_{2-6}$ alkynyloxy.

In one embodiment, $R_7$ is cyclobutyl.

In one embodiment, $R_7$ is cyclobutyl substituted by one or more substituents independently chosen from fluoro, chloro, bromo and iodo.

In one embodiment, $R_7$ is cyclobutyl substituted by one or more fluoro.

In one embodiment, $R_7$ is trifluoromethyl-cyclobutyl.

In one embodiment, $R_7$ is 1-trifluoromethyl-cyclobutyl.

In one embodiment, $R_7$ is cyclopentyl.

In one embodiment, $R_7$ is cyclopentyl substituted by one or more substituents independently chosen from fluoro, chloro, bromo and iodo.

In one embodiment, $R_7$ is cyclopentyl substituted by one or more fluoro.

In one embodiment, $R_7$ is cyclohexyl.

In one embodiment, $R_7$ is cyclohexyl substituted by one or more substituents independently chosen from fluoro, chloro, bromo and iodo.

In one embodiment, $R_7$ is cyclohexyl substituted by one or more fluoro.

In one embodiment, $R_7$ is 4,4-difluorocyclohexyl.

In one embodiment, $R_7$ is $CH_2$-tertbutyl.

In one embodiment, $R_3$ or $R_4$ are independently optionally substituted $C_{6-12}$ aryl or optionally substituted 3 to 10 membered heterocycle.

In a further embodiment, $R_3$ or $R_4$ are independently optionally substituted $C_{6-12}$ aryl.

In a further embodiment, $R_3$ or $R_4$ are independently optionally substituted 3 to 10 membered heterocycle.

In a further embodiment, $R_3$ or $R_4$ are independently optionally substituted $C_{7-12}$ aralkyl.

In a further embodiment, $R_3$ or $R_4$ are independently optionally 4-16 member heteroaralkyl.

In further embodiments:

$R_3$ or $R_4$ are independently benzyl;

$R_3$ or $R_4$ are independently benzyl substituted with a halogen;

$R_3$ or $R_4$ are independently benzyl substituted with Br;

$R_3$ or $R_4$ are independently benzyl substituted with F;

$R_3$ or $R_4$ are independently benzyl substituted with Cl;

$R_3$ or $R_4$ are independently benzyl substituted with at least one halogen;

$R_3$ or $R_4$ are independently benzyl substituted with a $C_{1-3}$ alkoxy;

$R_3$ or $R_4$ are independently benzyl substituted with methoxy;

$R_3$ or $R_4$ are independently benzyl substituted with ethoxy;

$R_3$ or $R_4$ are independently benzyl substituted with $SO_2C_{1-3}$alkyl;

$R_3$ or $R_4$ are independently benzyl substituted with methane sulfonyl;

$R_3$ or $R_4$ are independently benzyl substituted with difluoromethoxy;

$R_3$ or $R_4$ are independently benzyl substituted with trifluoromethoxy;

$R_3$ or $R_4$ are independently benzyl substituted with trifluoromethyl;

$R_3$ or $R_4$ are independently benzyl substituted with CN;

$R_3$ or $R_4$ are independently benzyl substituted with pyrrazoyl;

$R_3$ or $R_4$ are independently benzyl optionally substituted in the para (p) position.

$R_3$ or $R_4$ are independently optionally substituted $C_{6-12}$ aryl, optionally substituted $C_{7-12}$ aralkyl or optionally substituted 3 to 10 membered heterocycle.

$R_3$ or $R_4$ are independently optionally substituted $C_{6-12}$ aryl.

$R_3$ or $R_4$ are independently optionally substituted 3 to 10 membered heterocycle.

$R_3$ or $R_4$ are independently optionally substituted $C_{7-12}$ aralkyl.

$R_3$ or $R_4$ are independently $C_{6-12}$ aryl, $C_{7-12}$ aralkyl, 3 to 10 membered heterocycle or 4-16 member heteroaralkyl which are unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, C(O)C$_{2-6}$ alkynyl, C(O)C$_{6-12}$ aryl, C(O)C$_{7-12}$ aralkyl, 3-10 member heterocycle, 4-member heteroaralkyl, hydroxyl, oxo, oxime, NR$_{63}$R$_{64}$, C(O)OR$_{62}$, cyano, azido, amidino and guanido;

wherein R$_{62}$, R$_{65}$, R$_{66}$, R$_{63}$ and R$_{64}$ are each independently chosen from H, C$_{1-12}$ alkyl, C$_{2-12}$ alkenyl, C$_{2-12}$ alkynyl, C$_{6-12}$ aryl, 3-10 member heterocycle, 4-16 member heteroaralkyl, and C$_{7-18}$ aralkyl, or R$_{65}$ and R$_{66}$ are taken together with the oxygen atoms to form a 5 to 10 member heterocycle, or R$_{63}$ and R$_{64}$ are taken together with the nitrogen atom to form a 3 to 10 member heterocycle.

In a further embodiment, R$_3$ or R$_4$ are independently C$_{6-12}$ aryl, C$_{7-12}$ aralkyl, 3 to 10 membered heterocycle or 4-16 member heteroaralkyl which are unsubstituted or substituted by one or more substituents chosen from halogen, C$_{1-6}$ alkyl, NR$_{63}$R$_{64}$, nitro, CONR$_{63}$R$_{64}$, C$_{1-6}$ alkyloxy, C(O)OR$_{62}$, cyano, and azido;

wherein R$_{62}$, R$_{63}$ and R$_{64}$ are each independently chosen from H, C$_{1-12}$ alkyl, C$_{6-12}$ aryl, 3-10 member heterocycle, 4-16 member heteroaralkyl, and C$_{7-18}$ aralkyl, or R$_{63}$ and R$_{64}$ are taken together with the nitrogen to form a 3 to 10 member heterocycle.

In a further embodiment, R$_3$ or R$_4$ are independently C$_{6-12}$ aryl, C$_{7-12}$ aralkyl, 3 to 10 membered heterocycle or 4-16 member heteroaralkyl which are unsubstituted or substituted by one or more substituents chosen from a halogen, C$_{1-6}$ alkyl, C$_{1-6}$ alkyloxy, CF$_3$, COOH, COOC$_{1-6}$ alkyl, cyano, NH$_2$, nitro, NH(C$_{1-6}$ alkyl), N(C$_{1-6}$ alkyl)$_2$ and a 3-8 member heterocycle.

In a further embodiment, R$_3$ or R$_4$ are independently phenyl or benzyl which are unsubstituted or substituted by one or more substituents chosen from halogen, nitro, CONR$_{63}$R$_{64}$, C$_{1-6}$ alkyl, C$_{2-6}$ alkenyl, C$_{1-6}$ alkyloxy, C$_{2-6}$ alkenyloxy, C$_{2-6}$ alkynyloxy, C(O)C$_{1-6}$ alkyl, C$_{6-12}$ aryl, 3-10 member heterocycle, 4-16 member heteroaralkyl, hydroxyl, NR$_{63}$R$_{64}$, C(O)OR$_{62}$, cyano, and azido;

wherein R$_{62}$, R$_{63}$ and R$_{64}$ are each independently chosen from H, C$_{1-12}$ alkyl, C$_{6-12}$ aryl, 3-10 member heterocycle, 4-16 member heteroaralkyl, and C$_{7-18}$ aralkyl, or R$_{63}$ and R$_{64}$ are taken together with the nitrogen to form a 3 to 10 member heterocycle.

In a further embodiment, R$_3$ or R$_4$ are independently phenyl or benzyl which are unsubstituted or substituted by one or more substituents chosen from halogen, C$_{1-6}$ alkyl, NR$_{63}$R$_{64}$, nitro, CONR$_{63}$R$_{64}$, C$_{1-6}$ alkyloxy, C(O)OR$_{62}$, cyano, and azido;

wherein R$_{62}$, R$_{63}$ and R$_{64}$ are each independently chosen from H, C$_{1-12}$ alkyl, C$_{6-12}$ aryl, 3-10 member heterocycle, 4-16 member heteroaralkyl, and C$_{7-18}$ aralkyl, or R$_{63}$ and R$_{64}$ are taken together with the nitrogen to form a 3 to 10 member heterocycle.

In a further embodiment, R$_3$ or R$_4$ are independently benzyl which are unsubstituted or substituted by one or more substituents chosen from halogen, C$_{1-6}$ alkyl, NR$_{63}$R$_{64}$, nitro, CONR$_{63}$R$_{64}$, C$_{1-6}$ alkyloxy, C(O)OR$_{62}$, cyano, and azido;

wherein R$_{62}$, R$_{63}$ and R$_{64}$ are each independently chosen from H, C$_{1-12}$ alkyl, C$_{6-12}$ aryl, 3-10 member heterocycle, 4-16 member heteroaralkyl, and C$_{7-18}$ aralkyl;

or R$_{63}$ and R$_{64}$ are taken together with the nitrogen to form a 3 to 10 member heterocycle.

In a further embodiment, R$_3$ or R$_4$ are independently chosen from phenyl, benzyl, pyridinyl, thiophenyl, benzofuran, thiazole, and pyrazole, which are unsubstituted or substituted by one or more substituents chosen from a halogen, C$_{1-6}$ alkyl, C$_{1-6}$ alkyloxy, CF$_3$, COOH, COOC$_{1-6}$ alkyl, cyano, NH$_2$, nitro, NH(C$_{1-6}$ alkyl), N(C$_{1-6}$ alkyl)$_2$ and a 3-8 member heterocycle.

R$_3$ or R$_4$ are independently benzyl unsubstituted or substituted by one or more substituents chosen from halogen, C$_{1-3}$ alkoxy, SO$_2$C$_{1-3}$alkyl, difluoromethoxy, trifluoromethoxy, trifluoromethyl, CN and pyrazoyl.

R$_3$ or R$_4$ are independently benzyl optionally substituted in the para (p) position.

R$_3$ or R$_4$ are independently azetidinyl, pyrrolidinyl, piperazinyl, piperidyl, piperidino, oxetanyl, tetrahydropyranyl, tetrahydrofuranyl, morpholinyl, CH$_2$-azetidinyl, CH$_2$-pyrrolidinyl, CH$_2$-piperazinyl, CH$_2$-piperidyl, CH$_2$-oxetanyl, CH$_2$-tetrahydropyranyl, CH$_2$-tetrahydrofuranyl, CH$_2$-morpholinyl any of which can be unsubstituted or substituted by one or more substituents chosen from halogen, nitro, nitroso, SO$_3$R$_{62}$, PO$_3$R$_{65}$R$_{66}$, CONR$_{63}$R$_{64}$, C$_{1-6}$ alkyl, C$_{2-6}$ alkenyl, C$_{2-6}$ alkynyl, C$_{7-12}$ aralkyl, C$_{6-12}$ aryl, C$_{1-6}$ alkyloxy, C$_{2-6}$ alkenyloxy, C$_{2-6}$ alkynyloxy, C$_{6-12}$ aryloxy, C(O)C$_{1-6}$ alkyl, C(O)C$_{2-6}$ alkenyl, C(O)C$_{2-6}$ alkynyl, C(O)C$_{6-12}$ aryl, C(O)C$_{7-12}$ aralkyl, 3-10 member heterocycle, 4-16 member heteroaralkyl, hydroxyl, oxo, oxime, NR$_{63}$R$_{64}$, C(O)OR$_{62}$, cyano, azido, amidino and guanido;

wherein R$_{62}$, R$_{65}$, R$_{66}$, R$_{63}$ and R$_{64}$ are each independently chosen from H, C$_{1-12}$ alkyl, C$_{2-12}$ alkenyl, C$_{2-12}$ alkynyl, C$_{6-12}$ aryl, 3-10 member heterocycle, 4-16 member heteroaralkyl, and C$_{7-18}$ aralkyl, or R$_{65}$ and R$_{66}$ are taken together with the oxygen atoms to form a 5 to 10 member heterocycle, or R$_{63}$ and R$_{64}$ are taken together with the nitrogen atom to form a 3 to 10 member heterocycle.

In a further embodiment, R$_3$ or R$_4$ are independently azetidinyl, pyrrolidinyl, piperazinyl, piperidyl, piperidino, oxetanyl, tetrahydropyranyl, tetrahydrofuranyl, morpholinyl, CH$_2$-azetidinyl, CH$_2$-pyrrolidinyl, CH$_2$-piperazinyl, CH$_2$-piperidyl, CH$_2$-oxetanyl, CH$_2$-tetrahydropyranyl, CH$_2$-tetrahydrofuranyl, CH$_2$-morpholinyl any of which can be unsubstituted or substituted by one or more substituents chosen from halogen, C$_{1-6}$ alkyl, NR$_{63}$R$_{64}$, nitro, CONR$_{63}$R$_{64}$, C$_{1-6}$ alkyloxy, C(O)OR$_{62}$, cyano, and azido;

wherein R$_{62}$, R$_{63}$ and R$_{64}$ are each independently chosen from H, C$_{1-12}$ alkyl, C$_{6-12}$ aryl, 3-10 member heterocycle, 4-16 member heteroaralkyl, and C$_{7-18}$ aralkyl;

or R$_{63}$ and R$_{64}$ are taken together with the nitrogen to form a 3 to 10 member heterocycle.

In a further embodiment, R$_3$ or R$_4$ are independently azetidinyl, pyrrolidinyl, piperazinyl, piperidyl, piperidino, oxetanyl, tetrahydropyranyl, tetrahydrofuranyl, morpholinyl, CH$_2$-azetidinyl, CH$_2$-pyrrolidinyl, CH$_2$-piperazinyl, CH$_2$-piperidyl, CH$_2$-oxetanyl, CH$_2$-tetrahydropyranyl, CH$_2$-tetrahydrofuranyl, CH$_2$-morpholinyl any of which can be unsubstituted or substituted by one or more substituents chosen from a halogen, C$_{1-6}$ alkyl, C$_{1-6}$ alkyloxy, CF$_3$, COOH, COOC$_{1-6}$ alkyl, cyano, NH$_2$, nitro, NH(C$_{1-6}$ alkyl), N(C$_{1-6}$ alkyl)$_2$ and a 3-8 member heterocycle.

R$_3$ or R$_4$ are independently oxetanyl, tetrahydropyranyl, tetrahydrofuranyl, morpholinyl, CH$_2$-oxetanyl, CH$_2$-tetrahydropyranyl, CH$_2$-tetrahydrofuranyl, any of which can be unsubstituted or substituted by one or more substituents chosen from halogen, C$_{1-6}$ alkyl, NH$_2$, nitro, C(O)OC$_{1-6}$ alkyl, COOH, C$_{1-6}$ alkyloxy, cyano, and azido.

R$_3$ or R$_4$ are independently CH$_2$-oxetanyl, CH$_2$-tetrahydropyranyl, CH$_2$-tetrahydrofuranyl any of which can be unsubstituted or substituted by one or more substituents chosen from halogen, C$_{1-6}$ alkyl, NH$_2$, nitro, C(O)OC$_{1-6}$ alkyl, COOH, C$_{1-6}$ alkyloxy, cyano, and azido.

$R_3$ or $R_4$ are independently optionally substituted $C_{1-12}$ alkyl (e.g., methyl, ethyl, isopropyl, cyclopropyl, cyclobutyl, tert-butyl, cyclopentyl, cyclohexyl, or cycloheptyl).

$R_3$ or $R_4$ are independently $C_{1-12}$ alkyl optionally substituted.

$R_3$ or $R_4$ are independently $C_{1-6}$ alkyl optionally substituted.

$R_3$ or $R_4$ are independently $C_{3-12}$ cycloalkyl optionally substituted.

$R_3$ or $R_4$ are independently $C_{3-10}$ cycloalkyl optionally substituted.

$R_3$ or $R_4$ are independently $C_{5-7}$ cycloalkyl optionally substituted.

$R_3$ or $R_4$ are independently optionally substituted $C_{6-7}$ cycloalkyl.

$R_3$ or $R_4$ are independently optionally substituted $C_6$ cycloalkyl.

In a further embodiment, $R_3$ or $R_4$ are independently chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino and guanido;
wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl,
or $R_{65}$ and $R_{66}$ are taken together with the oxygen atoms to form a 5 to 10 member heterocycle,
or $R_{63}$ and $R_{64}$ are taken together with the nitrogen atom to form a 3 to 10 member.

In a further embodiment, $R_3$ or $R_4$ are independently chosen from methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl any of which unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;
wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
or $R_{63}$ and $R_{64}$ are taken together with the nitrogen to form a 3 to 10 member heterocycle.

In a further embodiment, $R_3$ or $R_4$ are independently methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl any of which unsubstituted or substituted by one or two substituents chosen from halogen, $C_{1-6}$ alkyl, $NR_{63}R_{64}$, nitro, $CONR_{83}R_{84}$, $C_{1-6}$ alkyloxy, $C(O)OR_{62}$, cyano, and azido;
wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl;
or $R_{63}$ and $R_{64}$ are taken together with the nitrogen to form a 3 to 10 member heterocycle.

In a further embodiment, $R_3$ or $R_4$ are independently methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl any of which unsubstituted or substituted by one or more substituents chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ and a 3-8 heterocycle.

In a further embodiment, $R_3$ or $R_4$ are independently chosen from methyl, ethyl, vinyl, propyl, propenyl, isopropyl, butyl, isobutyl, pentyl, neopentyl, or tert-butyl.

In a further embodiment, $R_3$ or $R_4$ are independently unsubstituted methyl or methyl substituted by one or more halogens.

In a further embodiment, $R_3$ or $R_4$ are independently unsubstituted methyl or methyl substituted by one or more fluoro.

In a further embodiment, $R_3$ or $R_4$ are independently H.

In a further embodiment, $R_3$ is chosen from methyl, ethyl, vinyl, propyl, propenyl, isopropyl, butyl, isobutyl, pentyl, neopentyl, or tert-butyl.

In a further embodiment, $R_3$ is methyl, ethyl, isopropyl or isobutyl.

In a further embodiment, $R_3$ is methyl.

In a further embodiment, $R_4$ is chosen from methyl, ethyl, vinyl, propyl, propenyl, isopropyl, butyl, isobutyl, pentyl, neopentyl, or tert-butyl.

In a further embodiment, $R_4$ is isopropyl or isobutyl. In a further embodiment, $R_4$ is isopropyl.

In a further embodiment, $R_4$ is isobutyl.

In a further embodiment, $R_5$, $R'_5$, $R_6$, $R'_6$, $R_8$ and $R_9$ are independently H or $C_{1-12}$ alkyl unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino and guanido;
wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl,
or $R_{65}$ and $R_{66}$ are taken together with the oxygen atoms to form a 5 to 10 member heterocycle,
or $R_{63}$ and $R_{64}$ are taken together with the nitrogen atom to form a 3 to 10 member heterocycle.

In a further embodiment, $R_5$, $R'_5$, $R_6$, $R'_6$, $R_8$ and $R_9$ are independently H or $C_{1-12}$ alkyl unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;
wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
or $R_{63}$ and $R_{64}$ are taken together with the nitrogen to form a 3 to 10 member heterocycle.

In a further embodiment, $R_5$, $R'_5$, $R_6$, $R'_6$, $R_8$ and $R_9$ are independently H or $C_{1-12}$ alkyl unsubstituted or substituted by one or more substituents chosen from halogen, $C_{1-8}$ alkyl, $NR_{63}R_{64}$, nitro, $CONR_{63}R_{64}$, $C_{1-8}$ alkyloxy, $C(O)OR_{62}$, cyano, and azido;
wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl,
or $R_{63}$ and $R_{64}$ are taken together with the nitrogen to form a 3 to 10 member heterocycle.

In a further embodiment, $R_5$, $R'_5$, $R_6$, $R'_6$, $R_8$ and $R_9$ are independently H or $C_{1-6}$ alkyl unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino and guanido;

wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

In a further embodiment, $R_5$, $R'_5$, $R_6$, $R'_6$, $R_8$ and $R_9$ are independently H or $C_{1-6}$ alkyl unsubstituted or substituted by one or more substituents chosen from halogen, nitro, $CONR_{63}R_{64}$, $C_{1-6}$ alkyl, $C_{2-6}$ alkenyl, $C_{1-6}$ alkyloxy, $C_{2-6}$ alkenyloxy, $C_{2-6}$ alkynyloxy, $C(O)C_{1-6}$ alkyl, $C_{6-12}$ aryl, 3-10 member heterocycle, 4-16 member heteroaralkyl, hydroxyl, $NR_{63}R_{64}$, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl, or $R_{63}$ and $R_{64}$ are taken together with the nitrogen to form a 3 to 10 member heterocycle.

In a further embodiment, $R_5$, $R'_5$, $R_6$, $R'_6$, $R_8$ and $R_9$ are independently H or $C_{1-6}$ alkyl unsubstituted or substituted by one or more substituents chosen from halogen, $C_{1-6}$ alkyl, $NR_{63}R_{64}$, nitro, $CONR_{63}R_{64}$, $C_{1-6}$ alkyloxy, $C(O)OR_{62}$, cyano, and azido;

wherein $R_{62}$, $R_{63}$ and $R_{64}$ are each independently chosen from H, $C_{1-12}$ alkyl, $C_{6-12}$ aryl, 3-10 member heterocycle, 4-16 member heteroaralkyl, and $C_{7-18}$ aralkyl;

or $R_{63}$ and $R_{64}$ are taken together with the nitrogen to form a 3 to 10 member heterocycle.

In a further embodiment $R_5$, $R'_5$, $R_6$, $R'_6$, $R_8$ and $R_9$ are independently H, methyl, ethyl, vinyl, propyl, propenyl, isopropyl, butyl, isobutyl, pentyl, neopentyl, tert-butyl, cyclopropyl, cyclobutyl, cyclopentyl, cyclohexyl.

In a further embodiment $R_5$, $R'_5$, $R_6$, $R'_6$, $R_8$ and $R_9$ are independently H.

In a further embodiment, the present invention provides a process and compounds used in the process for producing the compounds in accordance with the present invention.

In one embodiment the present invention provides a compound of formula A:

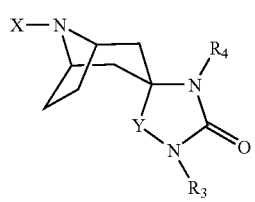

A wherein:
X is H or a nitrogen protecting group;
Y is C=O or $CR_5R'_5$;
wherein $R_3$, $R_4$, $R_5$ and $R'_5$ are as defined herein and provided that when Y is C=O one of $R_3$ or $R_4$ is not H.

The compounds of the present inventions have at least two asymmetric centers at the C-3 and C-4. As 2 optical isomers can independently be obtained from each asymmetric center, it is intended that all the possible optical isomers and diastereomers in mixtures and as pure or partially purified compounds are included in this invention.

In one embodiment, the compounds of the present invention are the (+) diastereoisomers having a diastereoisomeric excess of 99%.

In one embodiment, the compounds of the present invention are the (+) diastereoisomers having a diastereoisomeric excess of 95%.

In one embodiment, the compounds of the present invention are the (+) diastereoisomers having a diastereoisomeric excess of 90%.

In one embodiment, the compounds of the present invention are the (−) diastereoisomers having a diastereoisomeric excess of 99%.

In one embodiment, the compounds of the present invention are the (−) diastereoisomers having a diastereoisomeric excess of 95%.

In one embodiment, the compounds of the present invention are the (−) diastereoisomers having a diastereoisomeric excess of 90%.

In one embodiment the compounds of the present invention comprise diastereomers where C-3 and C-4 substituents are in the trans configuration.

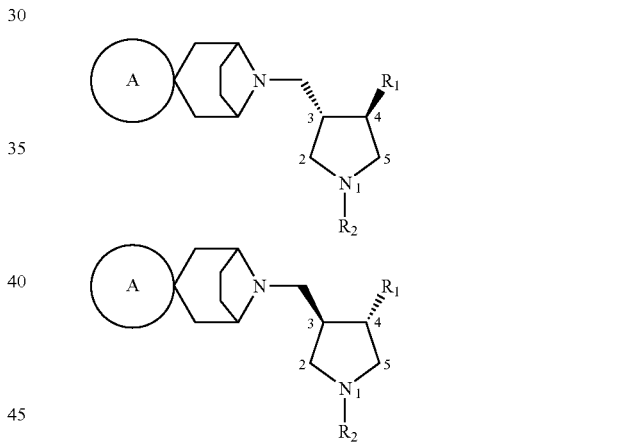

In one embodiment, there is provided a method of modulating chemokine receptor activity in a subject comprising administering to the subject a therapeutically effective amount of a compound of formula (I) or composition of the invention.

In another embodiment, there is provided a method for the prevention or treatment of diseases associated with the modulation of chemokine receptor activity in a subject in need of such treatment comprising administering to the subject a therapeutically effective amount of a compound of formula (I) or composition of the invention.

In a further embodiment, there is provided a method for prevention or treatment of certain inflammatory diseases, immunoregulatory diseases, organ transplantation reactions and in the prevention and treatment of infectious diseases such as HIV infections in a subject in need of such treatment comprising administering to the subject a therapeutically effective amount of a compound of formula (I) or composition of the invention.

In another embodiment, there is provided a method for the prevention or treatment of diseases associated with the modulation of CCR5 chemokine receptor activity in a subject in need of such treatment comprising administering to the subject a therapeutically effective amount of a compound of formula (I) or composition of the invention.

In still another aspect, there is provided a method for blocking cellular entry of HIV in a subject in need thereof comprising administering to the subject a therapeutically effective amount of a compound of formula (I) to block HIV from cellular entry in said subject.

In still another aspect, there is provided a method for prevention or treatment of HIV infections in a subject in need of such treatment comprising administering to the subject a therapeutically effective amount of a compound of formula (I) or composition of the invention.

In still another aspect, there is provided a method for delaying the onset of AIDS or treating AIDS in a subject in need of such treatment comprising administering to the subject a therapeutically effective amount of a compound of formula (I) or composition of the invention.

In a further embodiment, there is provided a method for the prevention or treatment of diseases associated with the modulation of chemokine receptor activity in a subject in need of such treatment comprising administering to the subject a pharmaceutical combination comprising at least one compound of formula (I) and at least one further therapeutic agent.

In a further embodiment, there is provided a method for the prevention or treatment of diseases associated with the modulation of CCR5 chemokine receptor activity in a subject in need of such treatment comprising administering to the subject a pharmaceutical combination comprising at least one compound of formula (I) and at least one further therapeutic agent.

In still another aspect, there is provided a method for blocking cellular entry of HIV in a subject or for the prevention or treatment of HIV infections in a subject in need of such treatment comprising administering to the subject a pharmaceutical combination comprising at least one compound of formula (I) and at least one further therapeutic agent.

In still another aspect, there is provided a method for delaying the onset of AIDS or treating AIDS in a subject in need of such treatment comprising administering to the subject a pharmaceutical combination comprising at least one compound of formula (I) and at least one further therapeutic agent.

In another embodiment, there is provided a combination useful for the prevention or treatment of diseases associated with the modulation of chemokine receptor activity which is a therapeutically effective amount of a compound of formula (I) and therapeutically effective amount of at least one further therapeutic agent.

In one embodiment, combinations of the present invention comprise those wherein the following embodiments are present, either independently or in combination.

In a further embodiment, the pharmaceutical combinations of this invention may contain at least one further therapeutic agent chosen from an agent used in inflammatory diseases, immunoregulatory diseases and in organ transplantation reactions.

In another embodiment, the pharmaceutical combination of this invention may contain at least one further therapeutic agent which is an antiviral agent.

In one embodiment, the pharmaceutical combination of this invention may contain at least one further antiviral agent which is chosen from nucleoside and nucleotide analog reverse transcriptase inhibitors, non-nucleoside reverse transcriptase inhibitors, protease inhibitors, attachment and fusion inhibitors, integrase inhibitors or maturation inhibitors.

In one embodiment, the pharmaceutical combinations of this invention may contain at least one other antiviral agent which is a nucleoside and nucleotide analog reverse transcriptase inhibitors chosen from 3TC (lamivudine, Epivir®), AZT (zidovudine, Retrovir®), Emtricitabine (Coviracil®, formerly FTC), d4T (2',3'-dideoxy-2',3'-didehydro-thymidine, stavudine and Zerit®), tenofovir (Viread®), 2',3'-dideoxyinosine (ddI, didanosine, Videx®), 2',3'-dideoxycytidine (ddC, zalcitabine, Hivid®), Combivir® (AZT/3TC or zidovudine/lamivudine combination), Trivizir® (AZT/3TC/abacavir or zidovudine/lamivudine/abacavir combination), abacavir (1592U89, Ziagen®), SPD-754, ACH-126,443 (Beta-L-Fd4C), Alovudine (MIV-310), DAPD (amdoxovir), Racivir, 9-[(2-hydroxymethyl)-1,3-dioxolan-4-yl]guanine or 2-amino-9-[(2-hydroxymethyl)-1,3-dioxolan-4-yl]adenine.

In another embodiment, the pharmaceutical combination of this invention may contain at least one other antiviral agent which is a non-nucleoside reverse transcriptase inhibitor chosen from Nevirapine (Viramune®, NVP, BI-RG-587), delavirdine (Rescriptor®, DLV), efavirenz (DMP 266, Sustiva®), (+)-Calanolide A, Capravirine (AG1549, formerly S-1153), DPC083, MIV-150, TMC120, TMC125 or BHAP (delavirdine), calanolides or L-697,661 (2-Pyridinone 3benzoxazolMeNH derivative).

In another embodiment, the pharmaceutical combination of this invention may contain at least one other antiviral agent which is a protease inhibitor chosen from nelfinavir (Viracept®, NFV), amprenavir (141W94, Agenerase®), indinavir (MK-639, IDV, Crixivan®), saquinavir (Invirase®, Fortovase®, SQV), ritonavir (Norvir®, RTV), lopinavir (ABT-378, Kaletra®), Atazanavir (BMS232632), mozenavir (DMP-450), fosamprenavir (GW433908), RO033-4649, Tipranavir (PNU-140690), TMC114 or VX-385.

In another embodiment, the pharmaceutical combination of this invention may contain at least one other antiviral agent which is an attachment and fusion inhibitor chosen from T-20 (enfuvirtide, Fuzeon®), T-1249, Schering C (SCH-C), Schering D (SCH-D), FP21399, PRO-140, PRO 542, PRO 452, TNX-355, GW873140 (AK602), TAK-220, TAK-652, UK-427,857 or soluble CD4, CD4 fragments, CD4-hybrid molecules, BMS-806, BMS-488043, AMD3100, AMD070 or KRH-2731.

In another embodiment, the pharmaceutical combination of this invention may contain at least one other antiviral agent which is an integrase inhibitor chosen from S-1360, L-870, 810, L-870,812, JTK-303 or C-2507.

In another embodiment, the pharmaceutical combination of this invention may contain at least one other antiviral agent which is a maturation inhibitor and is PA-457.

In another embodiment, the pharmaceutical combination of this invention may contain at least one other antiviral agent which is a zinc finger inhibitor and is azodicarbonamide (ADA).

In another embodiment, the pharmaceutical combination of this invention may contain at least one other antiviral agent which is an antisense drug and is HGTV43.

In another embodiment, the pharmaceutical combination of this invention may contain at least one other antiviral agent which is an immunomodulator, immune stimulator or cytokine chosen from interleukin-2 (IL-2, Aldesleukin, Proleukin), granulocyte macrophage colony stimulating factor (GM-CSF), erythropoietin, Multikine, Ampligen, thymomodulin, thymopentin, foscarnet, HE2000, Reticulose, Murabutide, Resveratrol, HRG214, HIV-1 Immunogen (Remune) or EP HIV-1090.

In another embodiment, the pharmaceutical combination of this invention may contain at least one other antiviral agent chosen from 2',3'-dideoxyadenosine, 3'-deoxythymidine, 2',3'-dideoxy-2',3'-didehydrocytidine and ribavirin; acyclic nucleosides such as acyclovir, ganciclovir; interferons such as alpha-, beta- and gamma-interferon; glucuronation inhibitors such as probenecid; or TIBO drugs, HEPT, TSAO derivatives.

The combinations referred to above may conveniently be presented for use in the form of a pharmaceutical formulation and thus pharmaceutical formulations comprising a combination as defined above together with a pharmaceutically acceptable carrier thereof comprises a further aspect of the invention.

The individual components of such combinations may be administered either sequentially or simultaneously in separate or combined pharmaceutical formulations.

In a further embodiment, the said compound of formula (I) and said therapeutic agent are administered sequentially.

In a further embodiment, the said compound of formula (I) and said therapeutic agent are administered simultaneously.

The subject to which the compounds are administered can be, for example, a mammal or a human. Preferably, the subject is a human.

In one embodiment, the present invention further provides a pharmaceutical composition comprising at least one compound having the formula (I) or pharmaceutically acceptable salts or pharmaceutically acceptable hydrates or pharmaceutically acceptable solvates thereof and at least one pharmaceutically acceptable carrier or excipient.

In another embodiment, the invention provides the use of a compound having the formula (I) for the manufacture of a medicament for prevention and treatment of diseases associated with the modulation of CCR5 chemokine receptor activity in a host comprising administering a therapeutically effective amount of a compound of formula (I).

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "alkyl" represents a linear, branched or cyclic hydrocarbon moiety having, for example, 1 to 10 carbon atoms, which may have one or more double bonds or triple bonds in the chain, and is optionally substituted. For example, unless otherwise stated, suitable substituents include halogen, amino, amidino, amido, azido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{7-12}$ aralkyl or 3 to 10 membered heterocycle), $NR_{29}C(O)R_{30}$, $NR_{29}C(O)OR_{30}$, $NR_{31}C(O)NR_{29}R_{30}$, $C(O)NR_{29}R_{30}$, $OC(O)NR_{29}R_{30}$ (wherein $R_{29}$, $R_{30}$ and $R_{31}$ are each independently selected from H, $C_{1-6}$ alkyl, $C_{6-12}$ aryl, $C_{7-12}$ aralkyl or 3 to 10 membered heterocycle, or $R_{29}$ and $R_{30}$ are taken together with the atoms to which they are attached to form a 3 to 10 membered heterocycle), $SO_2NR_{32}R_{33}$, $NR_{32}SO_2R_{33}$ (wherein $R_{32}$ and $R_{33}$ are each independently selected from the group consisting of H, $C_{1-6}$ alkyl, $C_{6-12}$ aryl, 3 to 10 membered heterocycle and $C_{7-12}$ aralkyl), $C(R_{34})NR_{35}$ or $C(R_{34})NOR_{35}$ (wherein $R_{34}$ and $R_{35}$ are each independently selected from the group consisting of H, $C_{1-6}$ alkyl, or $C_{6-12}$ aryl).

Preferred substituents for the alkyl groups include halogen (Br, Cl, I or F), cyano, nitro, oxo, amino, COOH, COO—$C_{1-4}$ alkyl, CO—$C_{1-4}$ alkyl, and phenyl.

Examples of alkyl groups include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, allyl, vinyl, acetylenyl, ethylenyl, propenyl, isopropenyl butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl, hexynyl, cyclopropyl, cyclobutyl, cycloheptyl, cyclohexenyl, cyclohex-dienyl and cyclohexyl.

The term alkyl is also meant to include alkyls in which one or more hydrogen atom is replaced by a halogen, i.e. an alkylhalide. Examples include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl.

The term "alkenyl" refers to alkyl groups may have one or more double bonds in the chain. The term "alkynyl" refers to alkyl groups may have one or more triple bonds in their chain. The alkenyl and alkynyl groups can be optionally substituted as described above for the alkyl groups.

The term "alkoxy" represents an alkyl which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy and neohexyloxy.

The term "alkylamino" represents an alkyl which is covalently bonded to the adjacent atom through a nitrogen atom and may be monoalkylamino or dialkylamino, wherein the alkyl groups may be the same or different. Examples include but are not limited to methylamino, dimethylamino, ethylamino, diethylamino, methylethylamino, propylamino, isopropylamino, butylamino, isobutylamino, sec-butylamino, tert-butylamino, pentylamino, isopentylamino, neopentylamino, tert-pentylamino, hexylamino, isohexylamino and neohexylamino.

The term "alkyloxycarbonyl" represents an alkyloxy which is covalently bonded to the adjacent atom through carbonyl (C=O). Examples include but are not limited to methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl, isohexyloxycarbonyl and neohexyloxycarbonyl.

The term "amidino" represents —C(=$NR_{10}$)$NR_{11}R_{12}$, wherein $R_{10}$, $R_{11}$ and $R_{12}$ are each independently selected from H, $C_{1-6}$ alkyl, $C_{6-12}$ aryl or $C_{7-12}$ aralkyl, or $R_{11}$ and $R_{12}$ are taken together with the nitrogen to which they are attached to form a 3 to 10 membered heterocycle.

The term "amido" represents —CONH$_2$, —CONHR$_{13}$ and —CONR$_{13}$R$_{14}$ wherein R$_{13}$ and R$_{14}$ are each independently selected from C$_{1-6}$ alkyl, C$_{6-12}$ aryl, 3 to 10 membered heterocycle or C$_{7-12}$ aralkyl, or R$_{13}$ and R$_{14}$ are taken together with the nitrogen to which they are attached to form a 3 to 10 membered heterocycle.

The term "amino" represents a derivative of ammonia obtained by substituting one or more hydrogen atom and include —NHR$_{15}$ and —NR$_{15}$R$_{16}$, wherein R$_{15}$ and R$_{16}$ are each independently selected from C$_{1-6}$ alkyl, C$_{6-12}$ aryl or C$_{7-12}$ aralkyl, or R$_{15}$ and R$_{16}$ are taken together with the nitrogen to which they are attached to form a 3 to 10 membered heterocycle.

The term "aryl" represents a carbocyclic moiety containing at least one benzenoid-type ring (i.e. the aryl group may be monocyclic or polycyclic), and which is optionally substituted with one or more substituents. For example, unless otherwise stated, suitable substituents include halogen, halogenated C$_{1-6}$ alkyl, halogenated C$_{1-6}$ alkoxy, amino, amidino, amido, azido, cyano, guanido, hydroxyl, nitro, nitroso, urea, OS(O)$_2$R$_{21}$ (wherein R$_{21}$ is selected from C$_{1-6}$ alkyl, C$_{6-12}$ aryl or 3 to 10 membered heterocycle), OS(O)$_2$OR$_{22}$ (wherein R$_{22}$ is selected from H, C$_{1-6}$ alkyl, C$_{6-12}$ aryl or 3 to 10 membered heterocycle), S(O)$_2$OR$_{23}$ (wherein R$_{23}$ is selected from H, C$_{1-6}$ alkyl, C$_{6-12}$ aryl or 3 to 10 membered heterocycle), S(O)$_{0-2}$R$_{24}$ (wherein R$_{24}$ is selected from H, C$_{1-6}$ alkyl, C$_{6-12}$ aryl or 3 to 10 membered heterocycle), OP(O)OR$_{25}$OR$_{26}$, P(O)OR$_{25}$OR$_{26}$ (wherein R$_{25}$ and R$_{26}$ are each independently selected from H or C$_{1-6}$ alkyl), C$_{1-6}$alkyl, C$_{7-12}$aralkyl, C$_{1-6}$alkoxy, C$_{7-12}$aralkyloxy (e.g. C$_{7-12}$ aralkyloxy), C$_{6-12}$aryloxy, 3 to 10 membered heterocycle, C(O)R$_{27}$ (wherein R$_{27}$ is selected from H, C$_{1-6}$ alkyl, C$_{6-12}$ aryl or 3 to 10 membered heterocycle), C(O)OR$_{28}$ (wherein R$_{28}$ is selected from H, C$_{1-6}$ alkyl, C$_{6-12}$ aryl, C$_{7-12}$ aralkyl or 3 to 10 membered heterocycle), NR$_{29}$C(O)R$_{30}$, NR$_{29}$C(O)OR$_{30}$, NR$_{31}$C(O)NR$_{29}$R$_{30}$, C(O)NR$_{29}$R$_{30}$, OC(O)NR$_{29}$R$_{30}$ (wherein R$_{29}$, R$_{30}$ and R$_{31}$ are each independently selected from H, C$_{1-6}$ alkyl, C$_{6-12}$ aryl, C$_{7-12}$ aralkyl or 3 to 10 membered heterocycle, or R$_{29}$ and R$_{30}$ are taken together with the atoms to which they are attached to form a 3 to 10 membered heterocycle), SO$_2$NR$_{32}$R$_{33}$, NR$_{32}$SO$_2$R$_{33}$ (wherein R$_{32}$ and R$_{33}$ are each independently selected from the group consisting of H, C$_{1-6}$ alkyl, C$_{6-12}$ aryl, 3 to 10 membered heterocycle and C$_{7-12}$ aralkyl), C(R$_{34}$)NR$_{35}$ or C(R$_{34}$)NOR$_{35}$ (wherein R$_{34}$ and R$_{35}$ are each independently selected from the group consisting of H, C$_{1-6}$ alkyl, or C$_{6-12}$ aryl).

Preferred substituents for the aryl groups include halogen (Br, Cl, I or F), cyano, nitro, oxo, amino, C$_{1-4}$ alkyl (e.g., CH$_3$, C$_2$H$_5$, isopropyl), C$_{1-4}$ alkoxy (e.g., OCH$_3$, OC$_2$H$_5$), halogenated C$_{1-4}$ alkyl (e.g., CF$_3$, CHF$_2$), halogenated C$_{1-4}$ alkoxy (e.g., OCF$_3$, OC$_2$F$_5$), COOH, COO—C$_{1-4}$ alkyl, CO—C$_{1-4}$ alkyl, C$_{1-4}$ alkyl-S— (e.g., CH$_3$S, C$_2$H$_5$S), halogenated C$_{1-4}$ alkyl-S— (e.g., CF$_3$S, C$_2$F$_5$S), benzyloxy, and pyrazolyl.

Examples of aryl include but are not limited to phenyl, tolyl, dimethylphenyl, aminophenyl, anilinyl, naphthyl, anthryl, phenanthryl or biphenyl.

The term "aralkyl" represents an aryl group attached to the adjacent atom by a C$_{1-6}$alkyl. Examples include but are not limited to benzyl, benzhydryl, trityl, phenethyl, 3-phenylpropyl, 2-phenylpropyl, 4-phenylbutyl and naphthylmethyl. The aryl and alkyl portions can be optionally substituted as described above.

The term "aralkyloxy" represents an aralkyl which is covalently bonded to the adjacent atom through an oxygen atom. Examples include but are not limited to benzyloxy, benzhydryloxy, trityloxy, phenethyloxy, 3-phenylpropyloxy, 2-phenylpropyloxy, 4-phenylbutyloxy and naphthylmethoxy. The aryl and alkyl portions can be optionally substituted as described above.

The term "aryloxy" represents an aryl which is covalently bonded to the adjacent atom through an oxygen atom. Examples include but are not limited to phenoxy and naphthyloxy. The aryl portion can be optionally substituted as described above.

There is also provided "enantiomers" and "diastereoisomers" of the present invention. It will be appreciated that the compounds in accordance with the present invention can contain one or more chiral centers. The compounds in accordance with the present invention may thus exist in the form of two different optical isomers, that is (+) or (−) enantiomers or in the form of different diastereomers. All such enantiomers, diastereomers and mixtures thereof, including racemic or other ratio mixtures of individual enantiomers and diastereomers, are included within the scope of the invention. The single diastereomer can be obtained by methods well known to those of ordinary skill in the art, such as HPLC, crystallization and chromatography. The single enantiomer can be obtained by methods well known to those of ordinary skill in the art, such as chiral HPLC, enzymatic resolution and chiral auxiliary derivatization.

The optical purity is numerically equivalent to the "enantiomeric excess". The term "enantiomeric excess" is defined in percentage (%) value as follows: [mole fraction (major enantiomer)−mole fraction (minor enantiomer)]×100. An example of enantiomeric excess of 99% represents a ratio of 99.5% of one enantiomer and 0.5% of the opposite enantiomer.

The term "guanido" or "guanidino" represents —NR$_{17}$C(=NR$_{18}$)NR$_{19}$R$_{20}$ wherein R$_{17}$, R$_{18}$, R$_{19}$ and R$_{20}$ are each independently selected from H, C$_{1-6}$ alkyl, C$_{6-12}$ aryl or C$_{7-12}$ aralkyl, or R$_{19}$ and R$_{20}$ are taken together with the nitrogen to which they are attached to form a 3 to 10 membered heterocycle.

The term "halogen" is specifically a fluoride atom, chloride atom, bromide atom or iodide atom.

The term "heterocycle" represents an optionally substituted saturated, unsaturated or aromatic cyclic moiety wherein said cyclic moiety is interrupted by at least one heteroatom selected from oxygen (O), sulfur (S) or nitrogen (N). Heterocycles may be monocyclic or polycyclic rings. For example, unless otherwise stated, suitable substituents include halogen, halogenated C$_{1-6}$ alkyl, halogenated C$_{1-6}$ alkoxy, amino, amidino, amido, azido, cyano, guanido, hydroxyl, nitro, nitroso, urea, OS(O)$_2$R$_{21}$ (wherein R$_{21}$ is selected from C$_{1-6}$ alkyl, C$_{6-12}$ aryl or 3 to 10 membered heterocycle), OS(O)$_2$OR$_{22}$ (wherein R$_{22}$ is selected from H, C$_{1-6}$ alkyl, C$_{6-12}$ aryl or 3 to 10 membered heterocycle), S(O)$_2$OR$_{23}$ (wherein R$_{23}$ is selected from H, C$_{1-6}$ alkyl, C$_{6-12}$ aryl or 3 to 10 membered heterocycle), S(O)$_{0-2}$R$_{24}$ (wherein R$_{24}$ is selected from H, C$_{1-6}$ alkyl, C$_{6-12}$ aryl or 3 to 10 membered heterocycle), OP(O)OR$_{25}$OR$_{26}$, P(O)OR$_{25}$OR$_{26}$ (wherein R$_{25}$ and R$_{26}$ are each independently selected from H or C$_{1-6}$ alkyl), C$_{1-6}$ alkyl, C$_{7-12}$aralkyl, C$_{1-6}$alkoxy, C$_{6-12}$ aryl, C$_{7-12}$aralkyloxy (e.g. C$_{7-12}$ aralkyloxy), C$_{6-12}$ aryloxy, C(O)R$_{27}$ (wherein R$_{27}$ is selected from H, C$_{1-6}$ alkyl, C$_{6-12}$ aryl or 3 to 10 membered heterocycle), C(O)OR$_{28}$ (wherein R$_{28}$ is selected from H, C$_{1-6}$ alkyl, C$_{6-12}$ aryl, C$_{7-12}$ aralkyl or 3 to 10 membered heterocycle), NR$_{29}$C(O)R$_{30}$, NR$_{29}$C(O)OR$_{30}$, NR$_{31}$C(O)NR$_{29}$R$_{30}$, C(O)NR$_{29}$R$_{30}$, OC(O)NR$_{29}$R$_{30}$ (wherein R$_{29}$, R$_{30}$ and R$_{31}$ are each independently selected from H, C$_{1-6}$ alkyl, C$_{6-12}$ aryl, C$_{7-12}$ aralkyl or 3 to 10 membered heterocycle, or R$_{29}$ and R$_{30}$ are taken together with the atoms to which they are attached to form a 3 to 10 membered heterocycle), $SO_2NR_{32}R_{33}$, $NR_{32}SO_2R_{33}$ (wherein $R_{32}$ and $R_{33}$ are each independently selected from the group consisting of H, $C_{1-6}$ alkyl, $C_{6-12}$ aryl, 3 to 10 membered heterocycle and $C_{7-12}$ aralkyl), $C(R_{34})NR_{35}$ or $C(R_{34})NOR_{35}$ (wherein $R_{34}$ and $R_{35}$ are each independently selected from the group consisting of H, $C_{1-6}$ alkyl, or $C_{6-12}$aryl).

Preferred substituents for the heterocycle groups include halogen (Br, Cl, I or F), cyano, nitro, oxo, amino, $C_{1-4}$ alkyl (e.g., $CH_3$, $C_2H_5$, isopropyl), $C_{1-4}$ alkoxy (e.g., $OCH_3$, $OC_2H_5$), halogenated $C_{1-4}$ alkyl (e.g., $CF_3$, $CHF_2$), halogenated $C_{1-4}$ alkoxy (e.g., $OCF_3$, $OC_2F_5$), COOH, COO—$C_{1-4}$ alkyl, CO—$C_{1-4}$ alkyl, $C_{1-4}$ alkyl-S— (e.g., $CH_3S$, $C_2H_5S$), halogenated $C_{1-4}$ alkyl-S— (e.g., $CF_3S$, $C_2F_5S$), benzyloxy, and pyrazolyl.

Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl.

The term "heteroaralkyl" represents a heterocycle group attached to the adjacent atom by a $C_{1-6}$ alkyl. The heterocycle and alkyl portions can be optionally substituted as described above.

"Amino-protecting group" is a protecting group conventionally used, which is subject to no particular limitation as long as it protects amino from various reactions. Specific examples include:

acyls such as acetyl; carbamates such as ethoxycarbonyl, alloc, and benzoyloxycarbonyl; aralkyls such as benzyl. Reference and useful additional examples may be found in "*Protective Groups in Organic Synthesis*" second edition, Wiley-interscience pulblication, by T. W. Greene and P. G. M. Wuts.

The term "independently" means that a substituent can be the same or a different definition for each item.

Unless otherwise stated, the term "optionally substituted" represents one or more halogen, halogenated $C_{1-6}$ alkyl, halogenated $C_{1-6}$ alkoxy, amino, amidino, amido, azido, cyano, guanido, hydroxyl, nitro, nitroso, urea, $OS(O)_2R_{21}$ (wherein $R_{21}$ is selected from $C_{1-6}$ alkyl, $C_{6-12}$ aryl or 3 to 10 membered heterocycle), $OS(O)_2OR_{22}$ (wherein $R_{22}$ is selected from H, $C_{1-6}$ alkyl, $C_{6-12}$ aryl or 3 to 10 membered heterocycle), $S(O)_2OR_{23}$ (wherein $R_{23}$ is selected from H, $C_{1-6}$ alkyl, $C_{6-12}$ aryl or 3 to 10 membered heterocycle), $S(O)_{0-2}R_{24}$ (wherein $R_{24}$ is selected from H, $C_{1-6}$ alkyl, $C_{6-12}$ aryl or 3 to 10 membered heterocycle), $OP(O)OR_{25}OR_{26}$, $P(O)OR_{25}OR_{26}$ (wherein $R_{25}$ and $R_{26}$ are each independently selected from H or $C_{1-6}$ alkyl), $C_{1-6}$alkyl, $C_{7-12}$ aralkyl, $C_{6-12}$ aryl, $C_{1-6}$ alkoxy, $C_{7-12}$ aralkyl oxy (e.g. $C_{7-12}$ aralkyloxy), $C_{6-12}$ aryloxy, 3 to 10 membered heterocycle, $C(O)R_{27}$ (wherein $R_{27}$ is selected from H, $C_{1-6}$ alkyl, $C_{6-12}$ aryl or 3 to 10 membered heterocycle), $C(O)OR_{28}$ (wherein $R_{28}$ is selected from H, $C_{1-6}$ alkyl, $C_{6-12}$ aryl, $C_{7-12}$ aralkyl or 3 to 10 membered heterocycle), $NR_{29}C(O)R_{30}$, $NR_{29}C(O)OR_{30}$, $NR_{31}C(O)NR_{29}R_{30}$, $C(O)NR_{29}R_{30}$, $OC(O)NR_{29}R_{30}$ (wherein $R_{29}$, $R_{30}$ and $R_{31}$ are each independently selected from H, $C_{1-6}$ alkyl, $C_{6-12}$ aryl, $C_{7-12}$ aralkyl or 3 to 10 membered heterocycle, or $R_{29}$ and $R_{30}$ are taken together with the atoms to which they are attached to form a 3 to 10 membered heterocycle), $SO_2NR_{32}R_{33}$, $NR_{32}SO_2R_{33}$ (wherein $R_{32}$ and $R_{33}$ are each independently selected from the group consisting of H, $C_{1-6}$ alkyl, $C_{6-12}$ aryl, 3 to 10 membered heterocycle and $C_{7-12}$ aralkyl), $C(R_{34})NR_{35}$ or $C(R_{34})NOR_{35}$ (wherein $R_{34}$ and $R_{35}$ are each independently selected from the group consisting of H, $C_{1-6}$ alkyl, or $C_{6-12}$ aryl).

The term "urea" represents —$N(R_{36})CONR_{37}R_{38}$ wherein $R_{36}$ is H or $C_{1-6}$ alkyl and wherein $R_{37}$ and $R_{38}$ are each independently selected from the group consisting of H, $C_{1-6}$ alkyl, $C_{6-12}$ aryl, 3 to 10 membered heterocycle and $C_{7-12}$ aralkyl, or $R_{37}$ and $R_{38}$ are taken together with the nitrogen to which they are attached to form a 3 to 10 membered heterocycle.

"Oxidation levels": When there is a sulfur atom present, the sulfur atom can be at different oxidation levels, i.e. S, SO, or $SO_2$. All such oxidation levels are within the scope of the present invention. When there is a nitrogen atom present, the nitrogen atom can be at different oxidation levels, i.e. N or NO. All such oxidation levels are within the scope of the present invention.

There is also provided "pharmaceutically acceptable hydrates" of the compounds of the present invention. "Hydrates" exist when the compound of the invention incorporates water. The hydrate may contain one or more molecule of water per molecule of compound of the invention. Illustrative non-limiting examples include monohydrate, dihydrate, trihydrate and tetrahydrate. The hydrate may contain one or more molecule of compound of the invention per molecule of water. Illustrative non-limiting examples include semi-hydrate. In one embodiment, the water may be held in the crystal in various ways and thus, the water molecules may occupy lattice positions in the crystal, or they may form bonds with salts of the compounds as described herein. The hydrate must be "acceptable" in the sense of not being deleterious to the recipient thereof. The hydration may be assessed by methods known in the art such as Loss on Drying techniques (LOD) and Karl Fisher titration.

There is also provided "pharmaceutically acceptable salts" of the compounds of the present invention. By the term "pharmaceutically acceptable salts" of compounds are meant those derived from pharmaceutically acceptable inorganic and organic acids and bases. Examples of suitable acids include but are not limited to hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal, alkaline earth metal or ammonium salts. The salt(s) must be "acceptable" in the sense of not being deleterious to the recipient thereof. Non-limiting examples of such salts known by those of ordinary skill in the art include without limitation calcium, potassium, sodium, choline, ethylenediamine, tromethamine, arginine, glycinelycine, lycine, magnesium and meglumine.

There is also provided a "pharmaceutically acceptable solvates" of the compounds of the present invention. The term "solvate" means that the compound of the invention incorporates one or more pharmaceutically acceptable solvent. The solvate may contain one or more molecule of solvent per molecule of compound of the invention or may contain one or more molecule of compound of the invention per molecule of solvent. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The solvation may be assessed by methods known in the art such as Loss on Drying techniques (LOD).

Reference hereinafter to a compound according to the invention includes compounds of the general formula (I) and their pharmaceutically acceptable salts, hydrates and solvates.

"Polymorphs": It will be appreciated by those skilled in the art that the compounds in accordance with the present invention can exist in several different crystalline forms due to a different arrangement of molecules in the crystal lattice. This may include solvate or hydrate (also known as pseudopolymorphs) and amorphous forms. All such crystalline forms and polymorphs are included within the scope of the invention. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC), differential thermal analysis (DTA), thermogravimetric analysis (TGA)), Raman spectroscopy, comparative intrinsic dissolution rate, scanning electron microscopy (SEM).

In one aspect, the present invention provides novel compounds including:

| Compound# | Compound name |
|---|---|
| 1 | (3S,4S)-3-[3-(4-Methanesulfonylbenzyl)-bicyclo[3.2.1]-2,4-dioxo-1α,3,8-triaza-spiro[4.5]dodec-8-ylmethyl]-4-phenyl-pyrrolidine-1-carboxylic acid tert-butyl ester |
| 2 | (3S,4S)-3-[1-Isopropyl-3-methyl-bicyclo[3.2.1]-2,4-dioxo-1β,3,8-triaza-spiro[4.5]dodec-8-ylmethyl]-4-phenyl-pyrrolidine-1-carboxylic acid tert-butyl ester |
| 3 | (3S,4S)-3-[3-Ethyl-1-isopropyl-bicyclo[3.2.1]-2,4-dioxo-1β,3,8-triaza-spiro[4.5]dodec-8-ylmethyl]-4-phenyl-pyrrolidine-1-carboxylic acid tert-butyl ester |
| 4 | (3S,4S)-3-[1-Isopropyl-3-(2-methoxy-ethyl)-bicyclo[3.2.1]-2,4-dioxo-1β,3,8-triaza-spiro[4.5]dodec-8-ylmethyl]-4-phenyl-pyrrolidine-1-carboxylic acid tert-butyl ester |
| 5 | (3S,4S)-3-[1-Isopropyl-3-(tetrahydrofuran-3-yl)-bicyclo[3.2.1]-2,4-dioxo-1β,3,8-triaza-spiro[4.5]dodec-8-ylmethyl]-4-phenyl-pyrrolidine-1-carboxylic acid tert-butyl ester |
| 6 | (3S,4S)-3-[1-Isopropyl-3-(tetrahydropyran-4-yl)-bicyclo[3.2.1]-2,4-dioxo-1β,3,8-triaza-spiro[4.5]dodec-8-ylmethyl]-4-phenyl-pyrrolidine-1-carboxylic acid tert-butyl ester |
| 7 | (3S,4S)-3-[1-Isopropyl-3-methyl-bicyclo[3.2.1]-2-oxo-1β,3,8-triaza-spiro[4.5]dodec-8-ylmethyl]-4-phenyl-pyrrolidine-1-carboxylic acid tert-butyl ester |
| 8 | (3S,4S)-3-[3-Ethyl-1-isopropyl-bicyclo[3.2.1]-2-oxo-1β,3,8-triaza-spiro[4.5]dodec-8-ylmethyl]-4-phenyl-pyrrolidine-1-carboxylic acid tert-butyl ester |
| 9 | (3S,4S)-1-benzyl-3-[3-(2,2-Difluoro-ethyl)-1-isopropyl-bicyclo[3.2.1]-2,4-dioxo-1β,3,8-triaza-spiro[4.5]dodec-8-ylmethyl]-4-phenyl-pyrrolidine |
| 10 | (3S,4S)-3-[3-(2,2-Difluoro-ethyl)-1-isopropyl-bicyclo[3.2.1]-2-oxo-1β,3,8-triaza-spiro[4.5]dodec-8-ylmethyl]-4-phenyl-pyrrolidine-1-carboxylic acid tert-butyl ester |
| 11 | (3S,4S)-3-[1-Isopropyl-3-(2-methoxy-ethyl)-bicyclo[3.2.1]-2-oxo-1β,3,8-triaza-spiro[4.5]dodec-8-ylmethyl]-4-phenyl-pyrrolidine-1-carboxylic acid tert-butyl ester |
| 12 | (3S,4S)-3-[1-Isopropyl-3-(tetrahydrofuran-3-yl)-bicyclo[3.2.1]-2-oxo-1β,3,8-triaza-spiro[4.5]dodec-8-ylmethyl]-4-phenyl-pyrrolidine-1-carboxylic acid tert-butyl ester |
| 13 | (3S,4S)-3-[1-Isopropyl-3-(tetrahydropyran-4-yl)-bicyclo[3.2.1]-2-oxo-1β,3,8-triaza-spiro[4.5]dodec-8-ylmethyl]-4-phenyl-pyrrolidine-1-carboxylic acid tert-butyl ester |
| 14 | (3R,4S)-3-[1-Isopropyl-3-methyl-bicyclo[3.2.1]-2,4-dioxo-1β,3,8-triaza-spiro[4.5]dodec-8-ylmethyl]-4-phenyl-pyrrolidine |
| 15 | (3R,4S)-3-[3-Ethyl-1-isopropyl-bicyclo[3.2.1]-2,4-dioxo-1β,3,8-triaza-spiro[4.5]dodec-8-ylmethyl]-4-phenyl-pyrrolidine |
| 16 | (3R,4S)-3-[3-(2,2-Difluoro-ethyl)-1-isopropyl-bicyclo[3.2.1]-2,4-dioxo-1β,3,8-triaza-spiro[4.5]dodec-8-ylmethyl]-4-phenyl-pyrrolidine |
| 17 | (3R,4S)-3-[1-Isopropyl-3-(2-methoxy-ethyl)-bicyclo[3.2.1]-2,4-dioxo-1β,3,8-triaza-spiro[4.5]dodec-8-ylmethyl]-4-phenyl-pyrrolidine |
| 18 | (3R,4S)-3-[1-Isopropyl-3-(tetrahydrofuran-3-yl)-bicyclo[3.2.1]-2,4-dioxo-1β,3,8-triaza-spiro[4.5]dodec-8-ylmethyl]-4-phenyl-pyrrolidine |
| 19 | (3R,4S)-3-[1-Isopropyl-3-(tetrahydropyran-4-yl)-bicyclo[3.2.1]-2,4-dioxo-1β,3,8-triaza-spiro[4.5]dodec-8-ylmethyl]-4-phenyl-pyrrolidine |
| 20 | (3R,4S)-3-[1-Isopropyl-3-methyl-bicyclo[3.2.1]-2-oxo-1β,3,8-triaza-spiro[4.5]dodec-8-ylmethyl]-4-phenyl-pyrrolidine |
| 21 | (3R,4S)-3-[3-Ethyl-1-isopropyl-bicyclo[3.2.1]-2-oxo-1β,3,8-triaza-spiro[4.5]dodec-8-ylmethyl]-4-phenyl-pyrrolidine |
| 22 | (3R,4S)-3-[3-(2,2-Difluoro-ethyl)-1-isopropyl-bicyclo[3.2.1]-2-oxo-1β,3,8-triaza-spiro[4.5]dodec-8-ylmethyl]-4-phenyl-pyrrolidine |
| 23 | (3R,4S)-3-[1-Isopropyl-3-(2-methoxy-ethyl)-bicyclo[3.2.1]-2-oxo-1β,3,8-triaza-spiro[4.5]dodec-8-ylmethyl]-4-phenyl-pyrrolidine |
| 24 | (3R,4S)-3-[1-Isopropyl-3-(tetrahydrofuran-3-yl)-bicyclo[3.2.1]-2-oxo-1β,3,8-triaza-spiro[4.5]dodec-8-ylmethyl]-4-phenyl-pyrrolidine |
| 25 | (3R,4S)-3-[1-Isopropyl-3-(tetrahydropyran-4-yl)-bicyclo[3.2.1]-2-oxo-1β,3,8-triaza-spiro[4.5]dodec-8-ylmethyl]-4-phenyl-pyrrolidine |
| 26 | (3S,4S)-1-Cyclopentanecarbonyl-3-[1-isopropyl-3-methyl-bicyclo[3.2.1]-2,4-dioxo-1β,3,8-triaza-spiro[4.5]dodec-8-ylmethyl]-4-phenyl-pyrrolidine |
| 27 | (3S,4S)-1-(1-Trifluoromethyl-cyclobutanecarbonyl)-3-[1-isopropyl-3-methyl-bicyclo[3.2.1]-2,4-dioxo-1β,3,8-triaza-spiro[4.5]dodec-8-ylmethyl]-4-phenyl-pyrrolidine |
| 28 | (3S,4S)-1-Cyclopentanecarbonyl-3-[3-ethyl-1-isopropyl-bicyclo[3.2.1]-2,4-dioxo-1β,3,8-triaza-spiro[4.5]dodec-8-ylmethyl]-4-phenyl-pyrrolidine |
| 29 | (3S,4S)-1-(3,3-Dimethyl-butyryl)-3-[3-ethyl-1-isopropyl-bicyclo[3.2.1]-2,4-dioxo-1β,3,8-triaza-spiro[4.5]dodec-8-ylmethyl]-4-phenyl-pyrrolidine |
| 30 | (3S,4S)-1-(1-Trifluoromethyl-cyclobutanecarbonyl)-3-[3-ethyl-1-isopropyl-bicyclo[3.2.1]-2,4-dioxo-1β,3,8-triaza-spiro[4.5]dodec-8-ylmethyl]-4-phenyl-pyrrolidine |
| 31 | (3S,4S)-1-Cyclopentanecarbonyl-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine |
| 32 | (3S,4S)-1-(3,3-Dimethyl-butyryl)-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine |

| Compound# | Compound name |
|---|---|
| 33 | (3S,4S)-1-Cyclopentanecarbonyl-3-[-1-isopropyl-3-(2-methoxy-ethyl)-bicyclo[3.2.1]-2,4-dioxo-1β,3,8-triaza-spiro[4.5]dodec-8-ylmethyl]-4-phenyl-pyrrolidine |
| 34 | (3S,4S)-1-(3,3-Dimethyl-butyryl)-3-[1-isopropyl-3-(2-methoxy-ethyl)-bicyclo[3.2.1]-2,4-dioxo-1β,3,8-triaza-spiro[4.5]dodec-8-ylmethyl]-4-phenyl-pyrrolidine |
| 35 | (3S,4S)-1-(3,3-Dimethyl-butyryl)-3-[1-isopropyl-3-(tetrahydro-furan-3-yl)-bicyclo[3.2.1]-2,4-dioxo-1β,3,8-triaza-spiro[4.5]dodec-8-ylmethyl]-4-phenyl-pyrrolidine |
| 36 | (3S,4S)-1-(3,3-Dimethyl-butyryl)-3-[1-isopropyl-3-(tetrahydro-pyran-4-yl)-bicyclo[3.2.1]-2,4-dioxo-1β,3,8-triaza-spiro[4.5]dodec-8-ylmethyl]-4-phenyl-pyrrolidine |
| 37 | (3S,4S)-1-Cyclopentanecarbonyl-3-[1-isopropyl-3-methyl-bicyclo[3.2.1]-2-oxo-1β,3,8-triaza-spiro[4.5]dodec-8-ylmethyl]-4-phenyl-pyrrolidine |
| 38 | (3S,4S)-1-(3,3-Dimethyl-butyryl)-3-[1-isopropyl-3-methyl-bicyclo[3.2.1]-2-oxo-1β,3,8-triaza-spiro[4.5]dodec-8-ylmethyl]-4-phenyl-pyrrolidine |
| 39 | (3S,4S)-1-(1-Trifluoromethyl-cyclobutanecarbonyl)-3-[1-isopropyl-3-methyl-bicyclo[3.2.1]-2-oxo-1β,3,8-triaza-spiro[4.5]dodec-8-ylmethyl]-4-phenyl-pyrrolidine |
| 40 | (3S,4S)-1-(2-Cyclopropyl-acetyl)-3-[1-isopropyl-3-methyl-bicyclo[3.2.1]-2-oxo-1β,3,8-triaza-spiro[4.5]dodec-8-ylmethyl]-4-phenyl-pyrrolidine |
| 41 | (3S,4S)-1-(3-Methyl-butyryl)-3-[1-isopropyl-3-methyl-bicyclo[3.2.1]-2-oxo-1β,3,8-triaza-spiro[4.5]dodec-8-ylmethyl]-4-phenyl-pyrrolidine |
| 42 | (3S,4S)-1-Cyclopentanecarbonyl-3-[3-ethyl-1-isopropyl-bicyclo[3.2.1]-2-oxo-1β,3,8-triaza-spiro[4.5]dodec-8-ylmethyl]-4-phenyl-pyrrolidine |
| 43 | (3S,4S)-1-(3,3-Dimethyl-butyryl)-3-[3-ethyl-1-isopropyl-bicyclo[3.2.1]-2-oxo-1β,3,8-triaza-spiro[4.5]dodec-8-ylmethyl]-4-phenyl-pyrrolidine |
| 44 | (3S,4S)-1-(1-Trifluoromethyl-cyclobutanecarbonyl)-3-[3-ethyl-1-isopropyl-bicyclo[3.2.1]-2-oxo-1β,3,8-triaza-spiro[4.5]dodec-8-ylmethyl]-4-phenyl-pyrrolidine |
| 45 | (3S,4S)-1-(3,3-Dimethyl-butyryl)-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine |
| 46 | (3S,4S)-1-Cyclopentanecarbonyl-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine |
| 47 | (3S,4S)-1-Cyclopentanecarbonyl-3-[-1-isopropyl-3-(2-methoxy-ethyl)-bicyclo[3.2.1]-2-oxo-1β,3,8-triaza-spiro[4.5]dodec-8-ylmethyl]-4-phenyl-pyrrolidine |
| 48 | (3S,4S)-1-(3,3-Dimethyl-butyryl)-3-[1-isopropyl-3-(2-methoxy-ethyl)-bicyclo[3.2.1]-2-oxo-1β,3,8-triaza-spiro[4.5]dodec-8-ylmethyl]-4-phenyl-pyrrolidine |
| 49 | (3S,4S)-1-(3,3-Dimethyl-butyryl)-3-[1-isobutyl-3-(2-methoxy-ethyl)-bicyclo[3.2.1]-2-oxo-1β,3,8-triaza-spiro[4.5]dodec-8-ylmethyl]-4-phenyl-pyrrolidine |
| 50 | (3S,4S)-1-Cyclopentanecarbonyl-3-[1-isopropyl-3-(tetrahydro-furan-3-yl)-bicyclo[3.2.1]-2-oxo-1β,3,8-triaza-spiro[4.5]dodec-8-ylmethyl]-4-phenyl-pyrrolidine |
| 51 | (3S,4S)-1-(3,3-Dimethyl-butyryl)-3-[1-isopropyl-3-(tetrahydro-furan-3-yl)-bicyclo[3.2.1]-2-oxo-1β,3,8-triaza-spiro[4.5]dodec-8-ylmethyl]-4-phenyl-pyrrolidine |
| 52 | (3S,4S)-1-Cyclopentanecarbonyl-3-[-1-isopropyl-3-(tetrahydro-pyran-4-yl)-bicyclo[3.2.1]-2-oxo-1β,3,8-triaza-spiro[4.5]dodec-8-ylmethyl]-4-phenyl-pyrrolidine |
| 53 | (3S,4S)-1-(3,3-Dimethyl-butyryl)-3-[1-isopropyl-3-(tetrahydro-pyran-4-yl)-bicyclo[3.2.1]-2-oxo-1β,3,8-triaza-spiro[4.5]dodec-8-ylmethyl]-4-phenyl-pyrrolidine |
| 54 | (3S,4S)-1-(4,4-Difluoro-cyclohexanecarbonyl)-3-[3-(4-N,N-dimethyl-benzenesulfonamide)-bicyclo[3.2.1]-2,4-dioxo-1α,3,8-triaza-spiro[4.5]dodec-8-ylmethyl]-4-phenyl-pyrrolidine |
| 55 | (3S,4S)-1-(3,3-Dimethyl-butyryl)-3-[1-isobutyl-3-methyl-bicyclo[3.2.1]-2,4-dioxo-1β,3,8-triaza-spiro[4.5]dodec-8-ylmethyl]-4-phenyl-pyrrolidine |
| 56 | (3S,4S)-1-(3,3-Dimethyl-butyryl)-3-[1-cyclopropylmethyl-3-methyl-bicyclo[3.2.1]-2,4-dioxo-1β,3,8-triaza-spiro[4.5]dodec-8-ylmethyl]-4-phenyl-pyrrolidine |
| 57 | (3S,4S)-1-(4,4-Difluoro-cyclohexanecarbonyl)-3-[1,3-diethyl-bicyclo[3.2.1]-2,4-dioxo-1β,3,8-triaza-spiro[4.5]dodec-8-ylmethyl]-4-phenyl-pyrrolidine |
| 58 | (3S,4S)-1-(3,3-Dimethyl-butyryl)-3-[3-ethyl-1-isobutyl-bicyclo[3.2.1]-2,4-dioxo-1β,3,8-triaza-spiro[4.5]dodec-8-ylmethyl]-4-phenyl-pyrrolidine |
| 59 | (3S,4S)-1-(3,3-Dimethyl-butyryl)-3-[1-isopropyl-3-methyl-bicyclo[3.2.1]-2,4-dioxo-1β,3,8-triaza-spiro[4.5]dodec-8-ylmethyl]-4-phenyl-pyrrolidine |
| 60 | (3S,4S)-1-(3,3-Dimethyl-butyryl)-3-[1-cyclopropylmethyl-3-methyl-bicyclo[3.2.1]-2-oxo-1β,3,8-triaza-spiro[4.5]dodec-8-ylmethyl]-4-phenyl-pyrrolidine |
| 61 | (3S,4S)-1-(3,3-Dimethyl-butyryl)-3-[1-isopropyl-3-methyl-bicyclo[3.2.1]-2,4-dioxo-1β,3,8-triaza-spiro[4.5]dodec-8-ylmethyl]-4-(3-fluorophenyl)-pyrrolidine |
| 62 | (3S,4S)-1-(3,3-Dimethyl-butyryl)-3-[1-isopropyl-3-methyl-bicyclo[3.2.1]-2-oxo-1β,3,8-triaza-spiro[4.5]dodec-8-ylmethyl]-4-(3-fluorophenyl)-pyrrolidine |
| 63 | (3S,4S)-1-Cyclopentanecarbonyl-3-[1-isopropyl-3-methyl-bicyclo[3.2.1]-2,4-dioxo-1β,3,8-triaza-spiro[4.5]dodec-8-ylmethyl]-4-(3-fluorophenyl)-pyrrolidine |
| 64 | (3S,4S)-1-Cyclopentanecarbonyl-3-[1-isopropyl-3-methyl-bicyclo[3.2.1]-2-oxo-1β,3,8-triaza-spiro[4.5]dodec-8-ylmethyl]-4-(3-fluorophenyl)-pyrrolidine |
| 65 | (3S,4S)-1-Cyclobutanecarbonyl-3-[1-isopropyl-3-methyl-bicyclo[3.2.1]-2,4-dioxo-1β,3,8-triaza-spiro[4.5]dodec-8-ylmethyl]-4-phenyl-pyrrolidine |
| 66 | (3S,4S)-1-Cyclobutanecarbonyl-3-[1-isopropyl-3-methyl-bicyclo[3.2.1]-2-oxo-1β,3,8-triaza-spiro[4.5]dodec-8-ylmethyl]-4-phenyl-pyrrolidine |
| 67 | (3S,4S)-1-(1-Methyl-cyclobutanecarbonyl)-3-[1-isopropyl-3-methyl-bicyclo[3.2.1]-2,4-dioxo-1β,3,8-triaza-spiro[4.5]dodec-8-ylmethyl]-4-phenyl-pyrrolidine |
| 68 | (3S,4S)-1-(1-Methyl-cyclobutanecarbonyl)-3-[1-isopropyl-3-methyl-bicyclo[3.2.1]-2-oxo-1β,3,8-triaza-spiro[4.5]dodec-8-ylmethyl]-4-phenyl-pyrrolidine |
| 69 | (3S,4S)-1-(1-Methyl-cyclopentanecarbonyl)-3-[1-isopropyl-3-methyl-bicyclo[3.2.1]-2,4-dioxo-1β,3,8-triaza-spiro[4.5]dodec-8-ylmethyl]-4-phenyl-pyrrolidine |
| 70 | (3S,4S)-1-(1-Methyl-cyclopentanecarbonyl)-3-[1-isopropyl-3-methyl-bicyclo[3.2.1]-2-oxo-1β,3,8-triaza-spiro[4.5]dodec-8-ylmethyl]-4-phenyl-pyrrolidine |
| 71 | (3S,4S)-1-(1-Methyl-cyclohexanecarbonyl)-3-[1-isopropyl-3-methyl-bicyclo[3.2.1]-2,4-dioxo-1β,3,8-triaza-spiro[4.5]dodec-8-ylmethyl]-4-phenyl-pyrrolidine |
| 72 | (3S,4S)-1-(1-Methyl-cyclohexanecarbonyl)-3-[1-isopropyl-3-methyl-bicyclo[3.2.1]-2-oxo-1β,3,8-triaza-spiro[4.5]dodec-8-ylmethyl]-4-phenyl-pyrrolidine |
| 73 | (3S,4S)-1-Cyclobutanecarbonyl-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine |
| 74 | (3S,4S)-1-Cyclobutanecarbonyl-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine |
| 75 | (3S,4S)-1-(1-Methyl-cyclobutanecarbonyl)-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine |
| 76 | (3S,4S)-1-(1-Methyl-cyclobutanecarbonyl)-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine |
| 77 | (3S,4S)-1-(1-Methyl-cyclopentanecarbonyl)-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine |
| 78 | (3S,4S)-1-(1-Methyl-cyclopentanecarbonyl)-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine |
| 79 | (3S,4S)-1-(1-Methyl-cyclohexanecarbonyl)-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine |
| 80 | (3S,4S)-1-(1-Methyl-cyclohexanecarbonyl)-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine |

| Compound# | Compound name |
|---|---|
| 81 | (3S,4S)-1-(3,3-Dimethyl-butyryl)-3-[3-(2-fluoro-ethyl)-1-isopropyl-bicyclo[3.2.1]-2,4-dioxo-1β,3,8-triaza-spiro[4.5]dodec-8-ylmethyl]-4-phenyl-pyrrolidine |
| 82 | (3S,4S)-1-(3,3-Dimethyl-butyryl)-3-[3-(2-fluoro-ethyl)-1-isopropyl-bicyclo[3.2.1]-2-oxo-1β,3,8-triaza-spiro[4.5]dodec-8-ylmethyl]-4-phenyl-pyrrolidine |
| 83 | (3S,4S)-1-Cyclopentanecarbonyl-3-[3-(2-fluoro-ethyl)-1-isopropyl-bicyclo[3.2.1]-2,4-dioxo-1β,3,8-triaza-spiro[4.5]dodec-8-ylmethyl]-4-phenyl-pyrrolidine |
| 84 | (3S,4S)-1-Cyclopentanecarbonyl-3-[3-(2-fluoro-ethyl)-1-isopropyl-bicyclo[3.2.1]-2-oxo-1β,3,8-triaza-spiro[4.5]dodec-8-ylmethyl]-4-phenyl-pyrrolidine |
| 85 | (3S,4S)-1-(3,3-Dimethyl-butyryl)-3-[3-(2,2,2-trifluoro-ethyl)-1-isopropyl-bicyclo[3.2.1]-2,4-dioxo-1β,3,8-triaza-spiro[4.5]dodec-8-ylmethyl]-4-phenyl-pyrrolidine |
| 86 | (3S,4S)-1-(3,3-Dimethyl-butyryl)-3-[3-(2,2,2-trifluoro-ethyl)-1-isopropyl-bicyclo[3.2.1]-2-oxo-1β,3,8-triaza-spiro[4.5]dodec-8-ylmethyl]-4-phenyl-pyrrolidine |
| 87 | (3S,4S)-1-Cyclopentanecarbonyl-3-[3-(2,2,2-trifluoro-ethyl)-1-isopropyl-bicyclo[3.2.1]-2,4-dioxo-1β,3,8-triaza-spiro[4.5]dodec-8-ylmethyl]-4-phenyl-pyrrolidine |
| 88 | (3S,4S)-1-Cyclopentanecarbonyl-3-[3-(2,2,2-trifluoro-ethyl)-1-isopropyl-bicyclo[3.2.1]-2-oxo-1β,3,8-triaza-spiro[4.5]dodec-8-ylmethyl]-4-phenyl-pyrrolidine |
| 89 | (3S,4S)-1-(3,3-Dimethyl-butyryl)-3-[1-isopropyl-3-oxetan-2-ylmethyl-bicyclo[3.2.1]-2,4-dioxo-1β,3,8-triaza-spiro[4.5]dodec-8-ylmethyl]-4-phenyl-pyrrolidine |
| 90 | (3S,4S)-1-(3,3-Dimethyl-butyryl)-3-[1-isopropyl-3-oxetan-2-ylmethyl-bicyclo[3.2.1]-2-oxo-1β,3,8-triaza-spiro[4.5]dodec-8-ylmethyl]-4-phenyl-pyrrolidine |
| 91 | (3S,4S)-1-(3,3-Dimethyl-butyryl)-3-[1-isopropyl-3-oxetan-3-ylmethyl-bicyclo[3.2.1]-2,4-dioxo-1β,3,8-triaza-spiro[4.5]dodec-8-ylmethyl]-4-phenyl-pyrrolidine |
| 92 | (3S,4S)-1-(3,3-Dimethyl-butyryl)-3-[1-isopropyl-3-oxetan-3-ylmethyl-bicyclo[3.2.1]-2-oxo-1β,3,8-triaza-spiro[4.5]dodec-8-ylmethyl]-4-phenyl-pyrrolidine |
| 93 | (3S,4S)-1-(3,3-Dimethyl-butyryl)-3-[1-isopropyl-3-(tetrahydro-furan-2-ylmethyl)-bicyclo[3.2.1]-2,4-dioxo-1β,3,8-triaza-spiro[4.5]dodec-8-ylmethyl]-4-phenyl-pyrrolidine |
| 94 | (3S,4S)-1-(3,3-Dimethyl-butyryl)-3-[1-isopropyl-3-(tetrahydro-furan-2-ylmethyl)-bicyclo[3.2.1]-2-oxo-1β,3,8-triaza-spiro[4.5]dodec-8-ylmethyl]-4-phenyl-pyrrolidine |
| 95 | (3S,4S)-1-(3,3-Dimethyl-butyryl)-3-[1-isopropyl-3-(tetrahydro-furan-3-ylmethyl)-bicyclo[3.2.1]-2,4-dioxo-1β,3,8-triaza-spiro[4.5]dodec-8-ylmethyl]-4-phenyl-pyrrolidine |
| 96 | (3S,4S)-1-(3,3-Dimethyl-butyryl)-3-[1-isopropyl-3-(tetrahydro-furan-3-ylmethyl)-bicyclo[3.2.1]-2-oxo-1β,3,8-triaza-spiro[4.5]dodec-8-ylmethyl]-4-phenyl-pyrrolidine |
| 97 | (3S,4S)-1-(3,3-Dimethyl-butyryl)-3-[1-isopropyl-3-(tetrahydro-pyran-2-ylmethyl)-bicyclo[3.2.1]-2,4-dioxo-1β,3,8-triaza-spiro[4.5]dodec-8-ylmethyl]-4-phenyl-pyrrolidine |
| 98 | (3S,4S)-1-(3,3-Dimethyl-butyryl)-3-[1-isopropyl-3-(tetrahydro-pyran-2-ylmethyl)-bicyclo[3.2.1]-2-oxo-1β,3,8-triaza-spiro[4.5]dodec-8-ylmethyl]-4-phenyl-pyrrolidine |
| 99 | (3S,4S)-1-(3,3-Dimethyl-butyryl)-3-[1-isopropyl-3-(tetrahydro-pyran-3-ylmethyl)-bicyclo[3.2.1]-2,4-dioxo-1β,3,8-triaza-spiro[4.5]dodec-8-ylmethyl]-4-phenyl-pyrrolidine |
| 100 | (3S,4S)-1-(3,3-Dimethyl-butyryl)-3-[1-isopropyl-3-(tetrahydro-pyran-3-ylmethyl)-bicyclo[3.2.1]-2-oxo-1β,3,8-triaza-spiro[4.5]dodec-8-ylmethyl]-4-phenyl-pyrrolidine |
| 101 | (3S,4S)-1-(3,3-Dimethyl-butyryl)-3-[1-isopropyl-3-(tetrahydro-pyran-4-ylmethyl)-bicyclo[3.2.1]-2,4-dioxo-1β,3,8-triaza-spiro[4.5]dodec-8-ylmethyl]-4-phenyl-pyrrolidine |
| 102 | (3S,4S)-1-(3,3-Dimethyl-butyryl)-3-[1-isopropyl-3-(tetrahydro-pyran-4-ylmethyl)-bicyclo[3.2.1]-2-oxo-1β,3,8-triaza-spiro[4.5]dodec-8-ylmethyl]-4-phenyl-pyrrolidine |
| 103 | (3S,4S)-1-(3,3-Dimethyl-butyryl)-3-[3-furan-2-ylmethyl-1-isopropyl-bicyclo[3.2.1]-2,4-dioxo-1β,3,8-triaza-spiro[4.5]dodec-8-ylmethyl]-4-phenyl-pyrrolidine |
| 104 | (3S,4S)-1-(3,3-Dimethyl-butyryl)-3-[3-furan-2-ylmethyl-1-isopropyl-bicyclo[3.2.1]-2-oxo-1β,3,8-triaza-spiro[4.5]dodec-8-ylmethyl]-4-phenyl-pyrrolidine |
| 105 | (3S,4S)-1-(3,3-Dimethyl-butyryl)-3-[3-furan-3-ylmethyl-1-isopropyl-bicyclo[3.2.1]-2,4-dioxo-1β,3,8-triaza-spiro[4.5]dodec-8-ylmethyl]-4-phenyl-pyrrolidine |
| 106 | (3S,4S)-1-(3,3-Dimethyl-butyryl)-3-[3-furan-3-ylmethyl-1-isopropyl-bicyclo[3.2.1]-2-oxo-1β,3,8-triaza-spiro[4.5]dodec-8-ylmethyl]-4-phenyl-pyrrolidine |
| 107 | (3S,4S)-1-(3,3-Dimethyl-butyryl)-3-[1-isopropyl-3-oxazol-2-ylmethyl-bicyclo[3.2.1]-2,4-dioxo-1β,3,8-triaza-spiro[4.5]dodec-8-ylmethyl]-4-phenyl-pyrrolidine |
| 108 | (3S,4S)-1-(3,3-Dimethyl-butyryl)-3-[1-isopropyl-3-oxazol-2-ylmethyl-bicyclo[3.2.1]-2-oxo-1β,3,8-triaza-spiro[4.5]dodec-8-ylmethyl]-4-phenyl-pyrrolidine |
| 109 | (3S,4S)-1-(3,3-Dimethyl-butyryl)-3-[3-(2-ethoxy-ethyl)-1-isopropyl-bicyclo[3.2.1]-2,4-dioxo-1β,3,8-triaza-spiro[4.5]dodec-8-ylmethyl]-4-phenyl-pyrrolidine |
| 110 | (3S,4S)-1-(3,3-Dimethyl-butyryl)-3-[3-(2-ethoxy-ethyl)-1-isopropyl-bicyclo[3.2.1]-2-oxo-1β,3,8-triaza-spiro[4.5]dodec-8-ylmethyl]-4-phenyl-pyrrolidine |
| 111 | (3S,4S)-1-(3,3-Dimethyl-butyryl)-3-[1-isopropyl-3-(2-methoxy-propyl)-bicyclo[3.2.1]-2,4-dioxo-1β,3,8-triaza-spiro[4.5]dodec-8-ylmethyl]-4-phenyl-pyrrolidine |
| 112 | (3S,4S)-1-(3,3-Dimethyl-butyryl)-3-[1-isopropyl-3-(2-methoxy-propyl)-bicyclo[3.2.1]-2-oxo-1β,3,8-triaza-spiro[4.5]dodec-8-ylmethyl]-4-phenyl-pyrrolidine | or pharmaceutically acceptable salts, hydrates or solvates thereof.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 μM, preferably about 2 to 50 μM, most preferably about 3 to about 30 μM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a pharmaceutically acceptable derivative thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

When the compound (I) or a pharmaceutically acceptable salt, hydrate or solvate thereof is used in combination with a second therapeutic active agent, the dose of each compound may be either the same as or different from that when the compound is used alone. Conventional doses and regimens are readily appreciated by those skilled in the art, including doses described in the Physicians Desk Reference, 56$^{th}$ edition, 2002.

The present invention is directed to the use of the compounds as modulators of CCR5 chemokine receptor activity. In particular, the compounds of the invention have been found to have activity in binding to the CCR5 receptor in the biological assay, as described in Example 7, generally with an $IC_{50}$ value of less than 25 µM. The terms "modulator" or "modulation" are meant to include antagonism, agonism, mixed and partial antagonism and agonism.

Certain compounds of the present invention have also been tested in an assay for HIV activity, as described in Example 7, and generally having an $IC_{50}$ value of less than 1 µM.

The purity and mass of the following examples were characterized by mass spectra (LC/MS) and or NMR spectra.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

The following general schemes and examples are provided to illustrate various embodiments of the present invention and shall not be considered as limiting in scope.

The following abbreviations may be used as follows:
br broad
DCE 1,2-dichloroethane
DCM dichloromethane
DMF N,N-dimethylformamide
Hal halogen
LAH lithium aluminium hydride
PG protecting group
Sept. septuplet
TFA trifluoroacetic acid
THF tetrahydrofuran
Semi-preparative HPLC purification procedures:
Column: Waters Symmetry Shield RP18, 5 microns, 19×100 mm
Buffer A: 3 mM HCl in H$_2$O (pH 2.4-2.6)
Buffer B: acetonitrile
Method A: 10% B to 35% B in 50 min.
Method B: 5% B to 25% B in 40 min.
Method C: 20% B to 45% B in 50 min.

Scheme 1

Preparation 1

(3R,4S)-3-Formyl-4-phenyl-pyrrolidine-1-carboxylic acid tert-butyl ester

Step 1: To (S)-(+)-4-phenyl-2-oxazolidinone (9.88 g, 60 mmol) in THF (150 mL) at −78° C., was added n-butyl lithium (37.7 mL, 1.6M in hexanes, 60 mmol) over a period of 30 minutes. THF (50 mL) was added to the resultant thick suspension and the reaction mixture allowed warming up to facilitate stirring. Trans-cinnamoylchloride (11.5 g, 69 mmol) in THF (30 mL) was added dropwise. The reaction was stirred at room temperature overnight. The reaction mixture was quenched with a saturated ammonium chloride solution (50 mL) and stirred for 0.5h. The solvent was removed in vacuo, the residue dissolved in ethyl acetate, washed with water (300 mL), 5% sodium bicarbonate (200 mL) and brine (100 mL) and dried over sodium sulfate. The solvent was removed in vacuo to give a pale yellow solid. The compound was crystallized from ethyl acetate and washed with hexanes to give 17.12 g (97%) of (S)-4-phenyl-3-[(E)-(3-phenyl-acryloyl)]-oxazolidin-2-one.

$^1$H NMR (400 MHz, CDCl$_3$): δ [ppm] 7.92 (d, 1H), 7.77 (d, 1H), 7.59 (m, 2H), 7.40-7.35 (m, 8H), 5.55 (dd, 1H), 4.74 (t, 1H), 4.31 (dd, 1H).

Step 2: N-Benzyl-N-(methoxymethyl)trimethylsilylmethylamine (10.03 g, 40.5 mmol) was added to (S)-4-phenyl-3-[(E)-(3-phenyl-acryloyl)]-oxazolidin-2-one (10.3 g, 35.1 mmol) in toluene (150 mL) at 0° C. and stirred for 20 minutes. Trifluoroacetic acid (9.7 mL) in dichloromethane (125 mL) was added dropwise to the reaction mixture keeping the internal temperature at 0° C. The reaction was stirred at room temperature overnight. The reaction mixture was poured into saturated sodium bicarbonate (200 mL) and extracted with dichloromethane (2×75 mL). The combined organic phases were washed with brine and dried over sodium sulfate. The organic phases were concentrated to give a waxy solid, which was purified by flash silica gel chromatography eluting with ethyl acetate:hexanes (1:9) to give 9.68 g (61%) of (S)-3-((3R,4S)-1-benzyl-4-phenyl-pyrrolidine-3-carbonyl)-4-phenyl-oxazolidin-2-one.

$^1$H NMR (400 MHz, CDCl$_3$): δ [ppm] 7.33-7.11 (m, 15H), 5.31 (m, 1H), 4.53 (t, 1H), 4.11 (m, 2H), 3.93 (q, 1H), 3.67 (dd, 1H), 3.48 (d, 1H), 3.22 (t, 1H), 3.03 (t, 1H), 2.69 (dd, 1H), 2.60 (t, 1H).

Step 3: To (S)-3-((3R,4S)-1-benzyl-4-phenyl-pyrrolidine-3-carbonyl)-4-phenyl-oxazolidin-2-one (9.96 g, 23.35 mmol) in THF (100 mL) in a three-necked flask equipped with a thermometer and addition funnel was added lithium aluminium hydride (48 mL, 1M in THF) dropwise so that the temperature did not exceed 40° C. while keeping the reaction vessel in a water bath. When addition was complete the water bath was removed and the reaction stirred at room temperature overnight. The reaction was carefully quenched with water (1.6 mL), NaOH (1.6 mL, 2N) and water (4.5 mL). After stirring for 15 minutes, the reaction mixture was filtered through a pad of celite and rinsed with THF (40 mL). The filtrate was concentrated to give a pale yellow oil, which was purified by flash silica gel chromatography eluting with ethyl acetate:hexanes (1:1) to give 3.38 g (55%) of ((3R,4S)-1-benzyl-4-phenyl-pyrrolidin-3-yl)-methanol.

$^1$H NMR (400 MHz, CDCl$_3$): δ [ppm] 7.4-7.2 (m, 10H), 3.73 (m, 2H), 3.66 (m, 2H), 3.3-3.2 (m, 2H), 2.9-2.8 (m, 2H), 2.5-2.4 (m, 2H).

LC/MS: m/z 267 (MH$^+$).

Step 4: To ((3R,4S)-1-benzyl-4-phenyl-pyrrolidin-3-yl)-methanol (2.28 g, 8.54 mmol) in ethanol (200 mL) was added ammonium formate (5.39 g, 85.49 mmol) and palladium hydroxide (446 mg, 20 wt % Pd) and refluxed for 1.5 h. Ammonia in methanol (0.8 mL, 2M) was added to the reaction mixture and refluxed for an additional 0.5 h. The reaction mixture was filtered through celite and concentrated to give ((3R,4S)-4-phenyl-pyrrolidin-3-yl)-methanol as a colorless oil (1.25 g) which was used directly in the next step.

Step 5: To ((3R,4S)-4-phenyl-pyrrolidin-3-yl)-methanol (1.25 g, 7.05 mmol) in THF (35 mL) was added triethylamine (0.97 mL, 7.05 mmol) at room temperature. The reaction mixture was cooled to 0° C. and di-tert-butyl dicarbonate (1.53 g, 7.05 mmol.) dissolved in THF (10 mL) was added. The reaction mixture was stirred overnight at room temperature. Then the reaction mixture was concentrated to give a colorless oil, which was purified by flash silica gel chromatography eluting with ethyl acetate:hexanes (2:3) to give 1.31 g (70%) of (3R,4S)-3-hydroxymethyl-4-phenyl-pyrrolidine-1-carboxylic acid tert-butyl ester.

$^1$H NMR (400 MHz, CDCl$_3$): δ [ppm] 7.31 (m, 2H), 7.23 (m, 3H), 3.82 (m, 1H), 3.76 (m, 1H), 3.66 (dd, 1H), 3.52 (dd, 1H), 3.38 (t, 1H), 3.28 (t, 1H), 3.11 (m, 2H), 2.49 (m, 2H), 1.46 (s, 9H).

Step 6: Oxalyl chloride (3.3 mL, 2M in CH$_2$Cl$_2$, 6.42 mmol) was stirred in dichloromethane (3 mL) in a three-necked flask. The reaction mixture was cooled to −78° C., and dimethyl sulfoxide (0.91 mL, 12.85 mmol) was added so that the internal temperature did not exceed −65° C. The reaction mixture was then stirred for 15 minutes. The (3R,4S)-3-hydroxymethyl-4-phenyl-pyrrolidine-1-carboxylic acid tert-butyl ester (713 mg, 2.57 mmol) in dichloromethane (6 mL) was added dropwise keeping the internal temperature below −65° C. and then stirred for 15 minutes. Diisopropylethylamine (4.5 mL, 25.7 mmol) was added keeping the internal temperature below −65° C. and then stirred for 20 minutes. The cooling bath was removed and the reaction mixture was stirred at room temperature for 2 h. The reaction mixture was concentrated to give a colorless oil, which was purified by flash silica gel chromatography eluting with ethyl acetate:hexanes (1:4) to give 496 mg (70%) of (3R,4S)-3-formyl-4-phenyl-pyrrolidine-1-carboxylic acid tert-butyl ester.

$^1$H NMR (400 MHz, CDCl$_3$): δ [ppm] 9.65 (s, 1H), 7.36-7.32 (m, 5H), 4.0-3.4 (m, 6H), 3.20 (m, 1H), 1.46 (s, 9H).

Scheme 2

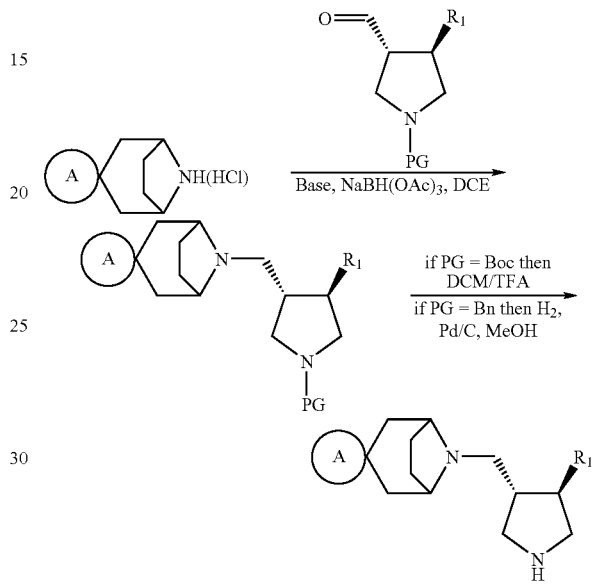

Preparation 2

3-(4-Methanesulfonylbenzyl)-bicyclo[3.2.1]-1α,3,8-triaza-spiro[4.5]dodecan-2,4-dione hydrochloride

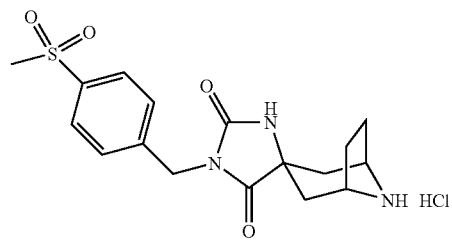

Step 1: A solution of Boc-nortropinone (2 g, 8.9 mmol), potassium cyanide (0.64 g, 9.8 mmol) and ammonium carbonate (2.6 g, 28 mmol) in ethanol (13 mL) and water (10 mL) was agitated for 2 days at room temperature. The mixture was filtered off and the precipitated solid washed with water. After overnight drying in vacuo, 1.21 g (46%) of bicyclo[3.2.1]-1α,3,8-triaza-spiro[4.5]dodecan-2,4-dione-8-carboxylic acid tert-butyl ester was isolated.

$^1$H NMR (400 MHz, DMSO-d$_6$): δ [ppm] 10.77 (s, 1H), 8.35 (s, 1H), 4.05 (s, 2H), 2.11-2.05 (m, 2H), 1.97-1.88 (m, 4H), 1.58-1.50 (m, 2H), 1.42 (s, 9H).

Step 2: To 0.15 g (0.5 mmol) of bicyclo[3.2.1]-1α,3,8-triaza-spiro[4.5]dodecan-2,4-dione-8-carboxylic acid tert-butyl ester were added successively 96 mg (0.56 mmol) of 4-methylthiobenzyl chloride, 70 mg (0.5 mmol) of potassium carbonate and 2.5 mL of anhydrous DMF. The reaction mixture was stirred overnight at room temperature. Then water was added and a white precipitated solid was collected by filtration. This crude material was back washed with water, hexanes and diethyl ether and dried under reduced pressure yielding 0.15 g (70%) of 3-(4-methylsulfanylbenzyl)-bicyclo[3.2.1]-1α,3,8-triaza-spiro[4.5]dodecan-2,4-dione-8-carboxylic acid tert-butyl ester as a white solid.

$^1$H NMR (400 MHz, DMSO-d$_6$): δ [ppm] 8.77 (s, 1H), 7.19 (d, 2H), 7.13 (d, 2H), 4.45 (s, 2H), 4.05 (s, 2H), 2.43 (s, 3H), 2.15-2.05 (m, 2H), 2.00-1.86 (m, 4H), 1.61-1.50 (m, 2H), 1.39 (s, 9H).

Step 3: To a solution of 0.15 g (0.35 mmol) of 3-(4-methylsulfanylbenzyl)-bicyclo[3.2.1]-1α,3,8-triaza-spiro[4.5]dodecan-2,4-dione-8-carboxylic acid tert-butyl ester in 2.3 mL of THF, was added 0.32 g (0.52 mmol) of Oxone® in 2.3 mL of water. The reaction mixture was agitated overnight at room temperature. An aqueous solution of sodium hydroxide (1N, 10 mL) was added and the solution was extracted with DCM (2×20 mL). The combined organic layers were dried (Na$_2$SO$_4$), filtered and evaporated under reduced pressure to yield 0.12 g (75%) of 3-(4-methanesulfonylbenzyl)-bicyclo[3.2.1]-1α,3,8-triaza-spiro[4.5]dodecan-2,4-dione-8-carboxylic acid tert-butyl ester as an off white foam.

$^1$H NMR (400 MHz, DMSO-d$_6$): δ [ppm] 8.84 (s, 1H), 7.87 (d, 2H), 7.43 (d, 2H), 4.62 (s, 2H), 4.07 (s, 2H), 3.18 (s, 3H), 2.22-2.12 (m, 2H), 2.00-1.88 (m, 4H), 1.67-1.55 (m, 2H), 1.39 (s, 9H).

Step 4: To 0.12 g (0.26 mmol) of 3-(4-methanesulfonylbenzyl)-bicyclo[3.2.1]-1α,3,8-triaza-spiro[4.5]dodecan-2,4-dione-8-carboxylic acid tert-butyl ester was added 0.5 mL of dioxane and 0.5 mL of 4N solution of dioxane/HCl. The reaction mixture was stirred for 5 hours at room temperature and concentrated in vacuo. The crude was dissolved in diethyl ether to obtain, after filtration, the 3-(4-methanesulfonylbenzyl)-bicyclo[3.2.1]-1α,3,8-triaza-spiro[4.5]dodecan-2,4-dione hydrochloride as a white solid (90 mg, 87%).

$^1$H NMR (400 MHz, DMSO-d$_6$): δ [ppm] 9.27 (broad s, 1H), 8.90 (s, 1H), 8.73 (broad d, 1H), 7.87 (d, 2H), 7.46 (d, 2H), 4.65 (s, 2H), 4.02 (s, 2H), 3.19 (s, 3H), 2.35 (d×d, 2H), 2.22-2.18 (m, 2H), 2.00-1.92 (m, 4H).

Preparation 3

1-Isopropyl-3-methyl-bicyclo[3.2.1]-1β,3,8-triaza-spiro[4.5]dodecan-2-one

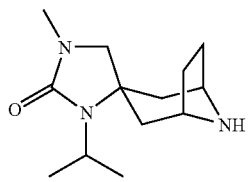

Step 1: To 9.22 g (42.8 mmol) of 8-benzyl-8-aza-bicyclo[3.2.1]octan-3-one previously dissolved in 42 mL of methanol was added successively 27.2 g (342 mmol) of ammonium acetate and 2.54 g of sodium cyanide. After stirring 24 h at room temperature, 100 mL of DCM and 50 mL of water were added and the solution was extracted with DCM (2×100 mL). The organic layers were dried over sodium sulfate, filtered and evaporated in vacuo to yield 10.36 g (100%) of 3β-amino-8-benzyl-8-aza-bicyclo[3.2.1]octane-3-carbonitrile as a pale yellow oil.

Step 2: To 12.06 g (50 mmol) of 3β-amino-8-benzyl-8-aza-bicyclo[3.2.1]octane-3-carbonitrile previously dissolved in 50 mL of acetic acid was added dropwise 21.2 g (250 mmol) of potassium cyanate diluted in 25 mL of water. Then the reaction mixture was heated at 110° C. for one hour. After it had cooled to room temperature, 120 mL of aqueous hydrochloride acid solution (6N) was added and the reaction mixture was heated at 110° C. for one hour and concentrated. The residue was redissolved in 200 mL of ethyl acetate and quenched with a saturated solution of sodium carbonate. The organic layer was washed with brine, dried over sodium sulfate, filtered off and concentrated. The orange residue was purified by flash silica gel chromatography eluting with ethyl acetate then DCM:methanol 2% to 10% to yield 1.93 g (13.5%) of 8-benzyl-bicyclo[3.2.1]-1β,3,8-triaza-spiro[4.5]dodecan-2,4-dione as an off white solid.

$^1$H NMR (400 MHz, DMSO-d$_6$): δ [ppm] 10.39 (br s, 1H), 7.76 (s, 1H), 7.36-7.17 (m, 5H), 3.51 (s, 2H), 3.11 (br s, 2H), 1.98-1.88 (m, 6H), 1.72 (d×d, 2H).

Step 3: To a mixture of 3.58 g (12.54 mmol) of 8-benzyl-bicyclo[3.2.1]-1β,3,8-triaza-spiro[4.5]dodecan-2,4-dione and 1.73 g (12.54 mmol) of potassium carbonate in 100 mL of anhydrous DMF was added 1.29 mL (20.6 mmol) of iodomethane. The reaction mixture was stirred for 18 hours at room temperature, diluted with water and extracted with diethyl ether. The combining organic layers were washed with water, brine, dried over sodium sulfate, filtered and concentrated to yield 1.93 g (52%) of 8-benzyl-3-methyl-bicyclo[3.2.1]-1β,3,8-triaza-spiro[4.5]dodecan-2,4-dione as a white solid.

Step 4: To 1.93 g (6.46 mmol) of 8-benzyl-3-methyl-bicyclo[3.2.1]-1β,3,8-triaza-spiro[4.5]dodecan-2,4-dione previously dissolved in 70 mL of anhydrous DMF was added 776 mg (19.4 mmol) of sodium hydride. The mixture was stirred at room temperature under nitrogen atmosphere for 5 minutes and 2-iodopropane (1.94 mL, 19.4 mmol) was added in one portion. The reaction was stirred for 3 days, quenched with water and extracted twice with diethyl ether. The combined organic layers were washed with water, brine and dried over sodium sulfate to yield, after flash silica gel chromatography eluting with hexanes:ethyl acetate 0% to 100%, 1.03 g (47%) of 8-benzyl-1-isopropyl-3-methyl-bicyclo[3.2.1]-1β,3,8-triaza-spiro[4.5]dodecan-2,4-dione.

$^1$H NMR (400 MHz, CDCl$_3$): δ [ppm] 7.37-7.24 (m, 5H), 3.64 (sept., 1H), 3.51 (s, 2H), 3.22 (br s, 2H), 2.91 (s, 3H), 2.21 (m, 2H), 2.09-2.01 (m, 4H), 1.78 (d×d, 2H), 1.46 (d, 6H).

Step 5: To 200 mg (0.586 mmol) of 8-benzyl-1-isopropyl-3-methyl-bicyclo[3.2.1]-1β,3,8-triaza-spiro[4.5]dodecan-2,4-dione previously dissolved in 4.5 mL of anhydrous THF was added at 0° C. 0.6 mL of a solution of LAH in THF (1M). The reaction mixture was stirred at 0° C. for 2 hours and then quenched with an aqueous solution of THF. The solution was acidified to pH 2 with HCl 0.5N and extracted 3 times with ethyl acetate. The combined organic layers were washed back twice with HCl 0.5N whereas the combined aqueous layers were basified to pH 10 with NaOH 6N and back extracted twice with ethyl acetate. All the organic layers were combined, washed with brine and dried over sodium sulfate, filtered and concentrated. The crude material was dissolved in 4 mL of formic acid and 89 mg (2.34 mmol) of sodium borohydride was added portion wise at 0° C. The reaction mixture was abandoned at room temperature with stirring for 30 minutes, diluted with DCM, neutralized with NaOH 1N and extracted twice with DCM. The combined organic layers were washed with brine, dried over sodium sulfate, filtered and concentrated to yield 180 mg (94%) of 8-benzyl-1-isopropyl-3-methyl-bicyclo[3.2.1]-1β,3,8-triaza-spiro[4.5]dodecan-2-one.

Step 6: To 104 mg (1.65 mmol) of ammonium formate and 77 mg (0.11 mmol) of palladium hydroxide placed in a 5 mL microwave tube was added 180 mg (0.55 mmol) of 8-benzyl-1-isopropyl-3-methyl-bicyclo[3.2.1]-1β,3,8-triaza-spiro[4.5]dodecan-2-one previously dissolved in 4 mL of ethanol. The tube was sealed and subjected to microwaves for 3 minutes at 120° C. and cooled to room temperature. The reaction mixture was filtered through celite, rinsed with ethanol and concentrated in vacuo to yield 130 mg (99%) of 1-isopropyl-3-methyl-bicyclo[3.2.1]-1β,3,8-triaza-spiro[4.5]dodecan-2-one as a white solid.

$^1$H NMR (400 MHz, DMSO-$d_6$): δ [ppm] 3.59 (sept., 1H), 3.46 (br s, 2H), 2.74 (s, 3H), 2.06 (d, 2H), 1.80 (d×d, 2H), 1.66 (d, 2H), 1.58 (m, 2H), 1.29 (d, 6H).

Or alternatively,

Step 1: N-Ethoxycarbonyltropinone (24.53 g, 124.3 mmol) was dissolved in 124 mL of methanol. Ammonium acetate (76.7 g, 8 eq.) was then added followed by sodium cyanide (7 g, 1.15 eq.). The reaction mixture was stirred overnight at room temperature. The solvent was then evaporated and 100 mL of water was added to the residue. The aqueous phase was extracted with DCM (3×200 mL). The resulting combined organic extracts was washed with 50 mL of water, dried over sodium sulfate and evaporated to afford 28.01 g of 3β-amino-3-cyano-8-aza-bicyclo[3.2.1]octane-8-carboxylic acid ethyl ester.

Step 2: To 7.83 g (35 mmol) of 3β-amino-3-cyano-8-aza-bicyclo[3.2.1]octane-8-carboxylic acid ethyl ester in DCM (100 mL) at 0° C. was added methyl isocyanate (2 g, 35 mmol) and the reaction stirred at room temperature overnight. The reaction mixture was diluted with DCM and washed with saturated sodium bicarbonate (2×50 mL), brine (2×20 mL) and then dried over sodium sulfate. The organic layer was concentrated and purified by flash silica gel chromatography eluting with methanol:DCM to give 3.01 g (31%) of 3-cyano-3β-(3-methyl-ureido)-8-aza-bicyclo[3.2.1]octane-8-carboxylic acid ethyl ester as a white foam.

Step 3: 3.01 g (10.7 mmol) of 3-cyano-3β-(3-methyl-ureido)-8-aza-bicyclo[3.2.1]octane-8-carboxylic acid ethyl ester in 6M HCl (20 mL) was heated at 80° C. for one hour. The reaction mixture was neutralized with 1N NaOH (40 mL) and extracted twice with DCM. The combined organics were dried over sodium sulfate, filtered and concentrated to give 2.94 g (97%) of 3-methyl-bicyclo[3.2.1]-1β,3,8-triaza-spiro[4.5]dodecan-2,4-dione-8-carboxylic acid ethyl ester as a white foam.

Step 4: To 2.94 g (10.4 mmol) of 3-methyl-bicyclo[3.2.1]-1β,3,8-triaza-spiro[4.5]dodecan-2,4-dione-8-carboxylic acid ethyl ester in DMF (50 mL) was added sodium hydride (1.25 g, 31.4 mmol). The reaction was stirred at room temperature for 0.5 hour until hydrogen evolution ceased. 2-Iodopropane (3.1 mL, 31.4 mmol) was added to the reaction mixture and heated at 60° C. overnight. A second portion of sodium hydride (0.62 g, 15.7 mmol) was added to the crude reaction mixture and stirred at room temperature for 0.5 hour until hydrogen evolution ceased. A second portion of 2-iodopropane (1.55 mL, 15.7 mmol) was added and heated at 60° C. overnight. The reaction mixture was diluted with water (50 mL) and extracted twice with diethyl ether (2×300 mL). The organics were dried over sodium sulfate, concentrated and purified by flash silica gel chromatography eluting with ethyl acetate:hexanes (20%-100%) to give 2.02 g (60%) of 1-isopropyl-3-methyl-bicyclo[3.2.1]-1β,3,8-triaza-spiro[4.5]dodecan-2,4-dione-8-carboxylic acid ethyl ester as a white foam.

$^1$H NMR (400 MHz, CDCl$_3$): δ [ppm] 4.4-4.2 (m, 4H), 3.09 (sept., 1H), 2.92 (s, 3H), 2.3-1.9 (m, 6H), 1.78 (d, 2H), 1.39 (d, 6H), 1.27 (t, 3H).

Step 5: To 2.02 g (6.24 mmol) of 1-isopropyl-3-methyl-bicyclo[3.2.1]-1β,3,8-triaza-spiro[4.5]dodecan-2,4-dione-8-carboxylic acid ethyl ester in THF (70 mL) was added LAH (6.56 mL, 6.56 mmol, 1M in THF) dropwise at 0° C. The reaction mixture was diluted with water:THF (1:1, 50 mL) and acidified to pH 2 with 1N HCl (20 mL). The aqueous was extracted twice with ethyl acetate (3×150 mL). The organics were washed with 1M NaOH (50 mL), brine (50 mL) dried over sodium sulfate and concentrated to give 1.47 g as a white solid. The crude was taken up in formic acid (25 mL) at 0° C. and sodium borohydride (0.945 g, 24.9 mmol) was added portionwise. The reaction allowed warming to room temperature for 0.5 hour. The reaction mixture was diluted with DCM, and neutralized with 6M NaOH. The aqueous was extracted twice with DCM, the organic layer washed with brine, dried over sodium sulfate and concentrated to give 1.33 g (69%) of 1-isopropyl-3-methyl-bicyclo[3.2.1]-1β,3,8-triaza-spiro[4.5]dodecan-2-one-8-carboxylic acid ethyl ester as a white solid.

Step 6: To 1.33 g (4.3 mmol) of 1-isopropyl-3-methyl-bicyclo[3.2.1]-1β,3,8-triaza-spiro[4.5]dodecan-2-one-8-carboxylic acid ethyl ester in toluene (50 mL) was added iodotrimethylsilane (1.75 mL, 12.9 mmol) and heated at 120° C. for 3 hours. The reaction mixture was concentrated and triturated with methanol (2×20 mL). The residue was purified by flash silica gel chromatography eluting with 2-20% methanol:DCM to give 0.522 g (51%) of 1-isopropyl-3-methyl-bicyclo[3.2.1]-1β,3,8-triaza-spiro[4.5]dodecan-2-one as a white foam.

Example 1

(3S,4S)-3-[3-(4-Methanesulfonylbenzyl)-bicyclo[3.2.1]-2,4-dioxo-1α,3,8-triaza-spiro[4.5]dodec-8-ylmethyl]-4-phenyl-pyrrolidine-1-carboxylic acid tert-butyl ester

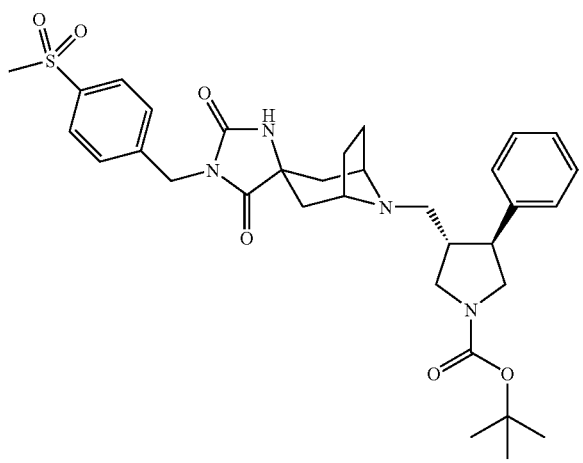

To a solution of 3-(4-methanesulfonylbenzyl)-bicyclo[3.2.1]-1α,3,8-triaza-spiro[4.5]dodecan-2,4-dione hydrochloride (40 mg, 0.1 mmol) in 1.7 mL of anhydrous DCE were added successively 28 mg (0.1 mmol) of (3R,4S)-3-formyl-4-phenyl-pyrrolidine-1-carboxylic acid tert-butyl ester and 17 μL (0.12 mmol) of triethylamine. The reaction mixture was agitated at room temperature for 10 minutes before adding 26 mg (0.125 mmol) of sodium triacetoxyborohydride. After an overnight agitation, 2 mL of saturated solution of sodium bicarbonate was added. The solution was then extracted with DCM (2×2 mL), dried over sodium sulfate, filtered and concentrated in vacuo. The crude mixture was purified by bond elute (ethyl acetate to 5% methanol/DCM) to yield (3S,4S)-3-[3-(4-methanesulfonylbenzyl)-bicyclo[3.2.1]-2,4-dioxo-1α,3,8-triaza-spiro[4.5]dodec-8-ylmethyl]-4-phenyl-pyrrolidine-1-carboxylic acid tert-butyl ester as a white solid (20 mg, 32.1%).

$^1$H NMR (400 MHz, DMSO-$d_6$): δ [ppm] 8.53 (s, 1H), 7.86 (d, 2H), 7.41 (d, 2H), 7.31-7.26 (m, 4H), 7.20-7.18 (m, 1H), 4.60 (s, 2H), 3.68-3.60 (m, 2H), 3.18 (s, 3H), 3.18-2.99 (m, 5H), 2.35-2.20 (m, 2H), 2.09-2.00 (m, 2H), 1.79-1.34 (m, 7H), 1.40 et 1.36 (s, 9H).

Example 2

(3S,4S)-3-[1-Isopropyl-3-methyl-bicyclo[3.2.1]-2-oxo-1β,3,8-triaza-spiro[4.5]dodec-8-ylmethyl]-4-phenyl-pyrrolidine-1-carboxylic acid tert-butyl ester

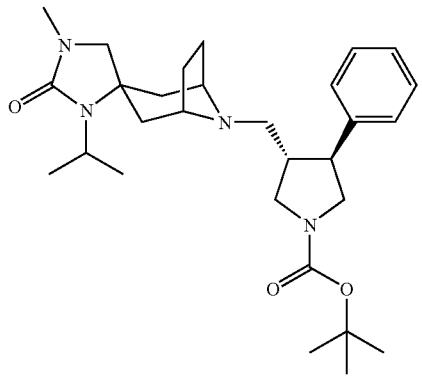

To 527 mg (2.22 mmol) of 1-isopropyl-3-methyl-bicyclo[3.2.1]-1β,3,8-triaza-spiro[4.5]dodecan-2-one in DCE (15 mL) was added 611 mg (2.22 mmol) of (3R,4S)-3-formyl-4-phenyl-pyrrolidine-1-carboxylic acid tert-butyl ester in DCE (10 mL) and stirred for 2 hours at room temperature. Sodium triacetoxyborohydride (706 mg, 3.33 mmol) was then added and the reaction mixture stirred overnight at room temperature. The reaction mixture was diluted with DCM, the organic layer washed with sodium bicarbonate, and then dried over sodium sulfate. The organic layer was concentrated and purified by flash silica gel chromatography eluting with methanol:DCM (0-10%) to give 612 mg (56%) of (3S,4S)-3-[1-isopropyl-3-methyl-bicyclo[3.2.1]-2-oxo-1β,3,8-triaza-spiro[4.5]dodec-8-ylmethyl]-4-phenyl-pyrrolidine-1-carboxylic acid tert-butyl ester as a white foam.

Example 3

(3R,4S)-3-[1-Isopropyl-3-methyl-bicyclo[3.2.1]-2-oxo-1β,3,8-triaza-spiro[4.5]dodec-8-ylmethyl]-4-phenyl-pyrrolidine

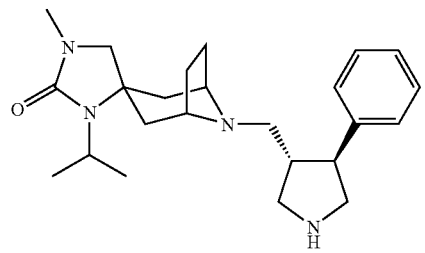

To 612 mg (1.23 mmol) of (3S,4S)-3-[1-isopropyl-3-methyl-bicyclo[3.2.1]-2-oxo-1β,3,8-triaza-spiro[4.5]dodec-8-ylmethyl]-4-phenyl-pyrrolidine-1-carboxylic acid tert-butyl ester in DCM (12 mL) was added TFA (3.3 mL). The reaction mixture was stirred for 0.75 hour at room temperature, neutralized with 1N NaOH (40 mL) and extracted with DCM. The organic layer was dried over sodium sulfate and concentrated to give 448 mg (88%) of (3R,4S)-3-[(1-isopropyl-3-methyl-bicyclo[3.2.1]-2-oxo-1β,3,8-triaza-spiro[4.5]dodec-8-ylmethyl]-4-phenyl-pyrrolidine as a white foam.

Table 1 of compounds illustrates some of the compounds of the present invention which could be synthesized using the procedures described in scheme 2.

Scheme 3a

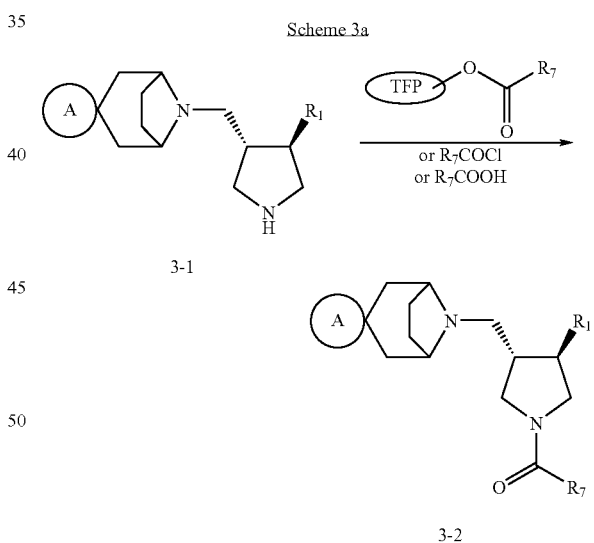

General procedure: the free amine 3-1 is condensed with preactivated carboxylic acid $R_7$COOH on polymeric 4-hydroxy-2,3,5,6-tetrafluorobenzamido (TFP) resin (see preparation in J. M. Salvino et al. *J. Comb. Chem.* 2000, 2, 691-697) in solvent such as DMF, or condensed with acid chloride $R_7$COCl in solvent such as DCM in presence of a base such as triethylamine or diisopropylethylamine, or condensed with a carboxylic acid $R_7$COOH in solvent such as DMF with coupling agents such as HOBt, DIC, HATU, BOP, PyBOP, to provide acylated compound 3-2.

Example 4

(3S,4S)-1-(3,3-Dimethyl-butyryl)-3-[1-isopropyl-3-methyl-bicyclo[3.2.1]-2-oxo-1β,3,8-triaza-spiro[4.5]dodec-8-ylmethyl]-4-phenyl-pyrrolidine hydrochloride

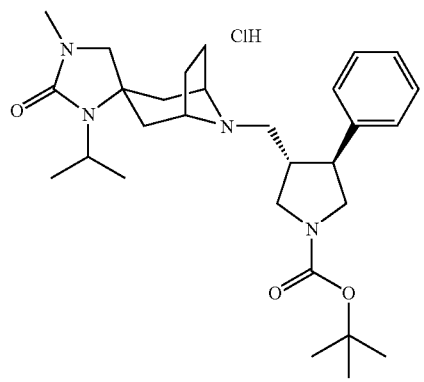

To 27 mg (0.068 mmol) of (3R,4S)-3-[(1-isopropyl-3-methyl-bicyclo[3.2.1]-2-oxo-1β,3,8-triaza-spiro[4.5]dodec-8-ylmethyl]-4-phenyl-pyrrolidine in DMF (1 mL) was added tert-butylacetic acid on polymer supported TFP resin (110 mg, 1.07 mmol/g). The reaction mixture was agitated overnight at room temperature, filtered and purified by semi-preparative HPLC (Method A) and lyophilized to give 14.2 mg (39%) of (3S,4S)-1-(3,3-dimethyl-butyryl)-3-[1-isopropyl-3-methyl-bicyclo[3.2.1]-2-oxo-1β,3,8-triaza-spiro[4.5]dodec-8-ylmethyl]-4-phenyl-pyrrolidine hydrochloride.

Table 2 of compounds illustrates some of the compounds of the present invention which could be synthesized using the procedures described in scheme 3a.

Example 5

(3S,4S)-1-(3,3-Dimethyl-butyryl)-3-[1-isopropyl-3-methyl-bicyclo[3.2.1]-2,4-dioxo-1β,3,8-triaza-spiro[4.5]dodec-8-ylmethyl]-4-phenyl-pyrrolidine hydrochloride

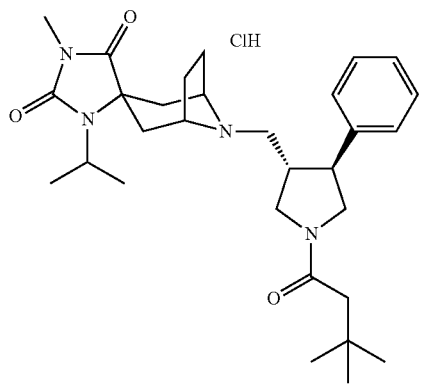

To 89 mg (0.35 mmol) of 1-isopropyl-3-methyl-bicyclo[3.2.1]-1β,3,8-triaza-spiro[4.5]dodecan-2,4-dione in DCE (5 mL) was added 97 mg (0.35 mmol) of (3R,4S)-1-(3,3-dimethyl-butyryl)-4-phenyl-pyrrolidine-3-carbaldehyde in DCE (5 mL) and stirred for 2 hours at room temperature. Sodium triacetoxyborohydride (113 mg, 0.53 mmol) was then added and the reaction mixture stirred overnight at room temperature. The reaction mixture was diluted with DCM, the organic layer washed with sodium bicarbonate, and then dried over sodium sulfate. The reaction mixture was filtered, purified by semi-preparative HPLC (Method B) and lyophilized to give (3S,4S)-1-(3,3-dimethyl-butyryl)-3-[1-isopropyl-3-methyl-bicyclo[3.2.1]-2,4-dioxo-1β,3,8-triaza-spiro[4.5]dodec-8-ylmethyl]-4-phenyl-pyrrolidine hydrochloride (16 mg, 8%).

Scheme 3b

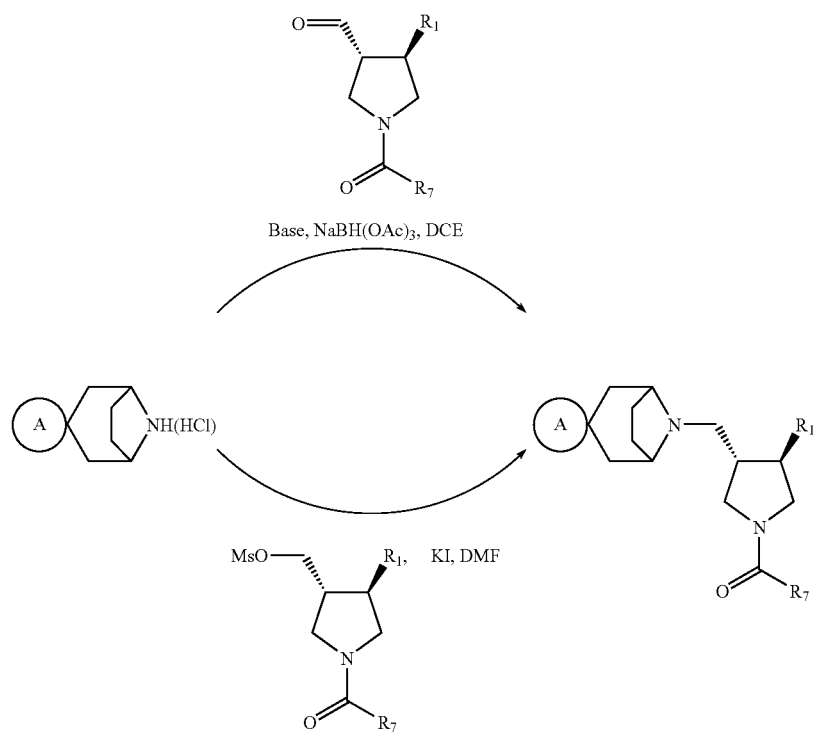

Example 6

(3S,4S)-1-(4,4-Difluoro-cyclohexanecarbonyl)-3-[1,3-diethyl-bicyclo[3.2.1]-2,4-dioxo-1β, 3,8-triaza-spiro[4.5]dodec-8-ylmethyl]-4-phenyl-pyrrolidine hydrochloride

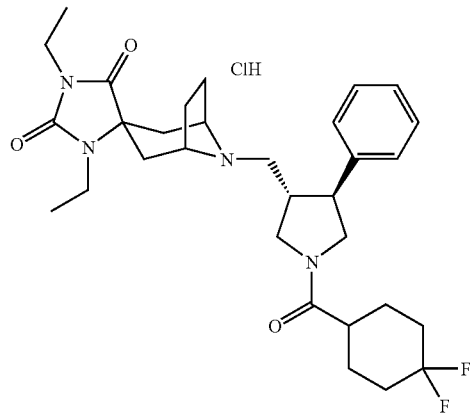

To 22 mg (0.085 mmol) of 1,3-diethyl-bicyclo[3.2.1]-1β,3,8-triaza-spiro[4.5]dodecan-2,4-dione in anhydrous DMF (1 mL) was added 35 mg (0.085 mmol) of methanesulfonic acid (3R,4S)-1-(4,4-difluoro-cyclohexanecarbonyl)-4-phenyl-pyrrolidin-3-ylmethyl ester, potassium iodide (14 mg, 0.085 mmol), and sodium bicarbonate (7 mg, 0.085 mmol) and the reaction stirred overnight at 80° C. The reaction mixture was filtered, purified by semi-preparative HPLC (Method C) and lyophilized to give (3S,4S)-1-(4,4-difluoro-cyclohexanecarbonyl)-3-[(1,3-diethyl-bicyclo[3.2.1]-2,4-dioxo-1β,3,8-triaza-spiro[4.5]dodec-8-ylmethyl]-4-phenyl-pyrrolidine hydrochloride (8.3 mg, 16%).

Table 3 of compounds illustrates some of the compounds of the present invention which could be synthesized using the procedures described in scheme 3b.

Scheme 4

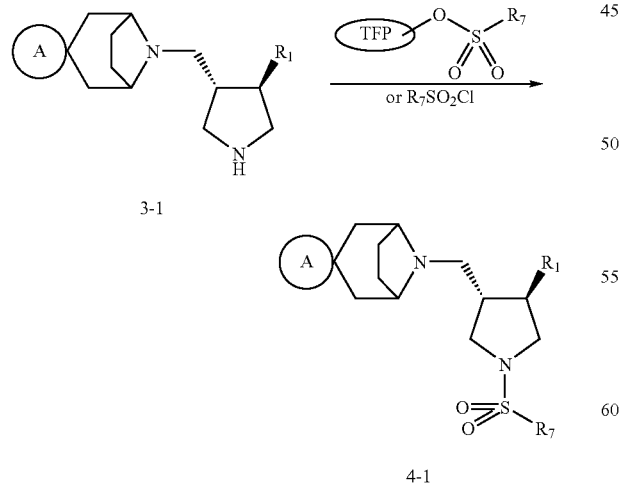

General procedure: the free amine 3-1 is condensed with preactivated sulfonyl chloride $R_7SO_2Cl$ on polymeric 4-hydroxy-2,3,5,6-tetrafluorobenzamido (TFP) resin (see preparation in J. M. Salvino et al. *J. Comb. Chem.* 2000, 2, 691-697) in solvent such as DMF, or with sulfonyl chloride $R_7SO_2Cl$ in solvent such as DCM in presence of a base such as triethylamine or diisopropylethylamine to provide the sulphonamide 4-1.

Scheme 5

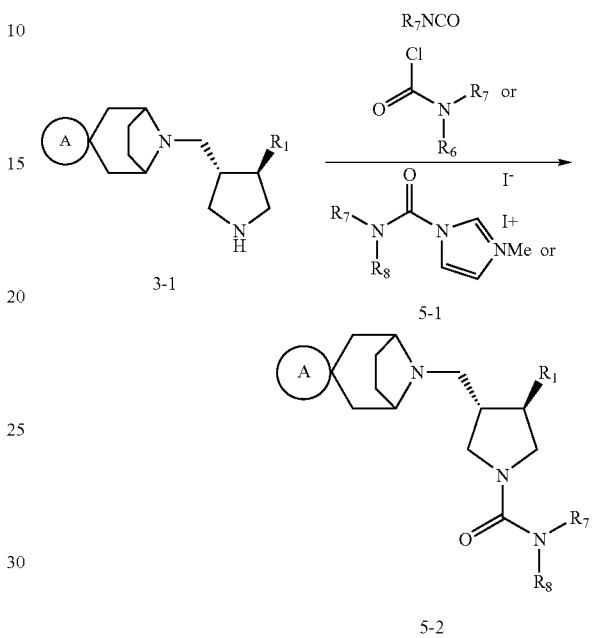

General procedure: the free amine 3-1 is submitted to reaction with isocyanate in solvent such as THF, or condensed with carbamoyl chloride derivative or with cationic carbamoyl imidazolium intermediate 5-1 (see R. A. Batey et al. *Comb. Chem. High Throughput Screening* 2002, 5, 219-232) in solvent such as DCM in presence of base such as triethylamine or diisopropylethylamine to provide the urea 5-2.

Scheme 6

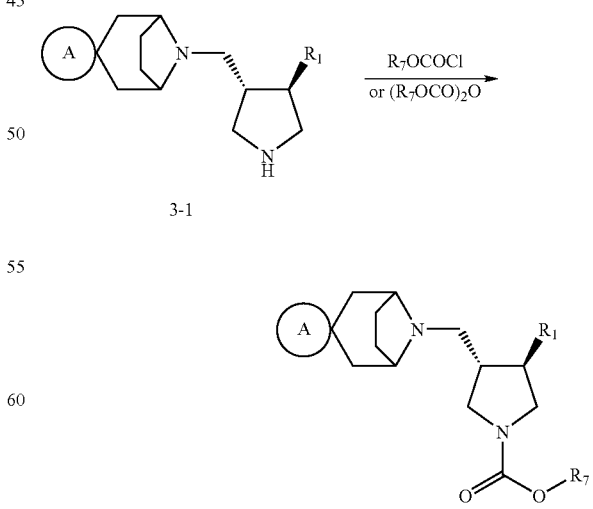

General procedure: the free amine 3-1 is condensed with chloroformate or symmetric anhydride in solvents such as DCM or 1,2-dichloroethane in the presence of a base such as triethylamine or diisopropylethylamine to provide the carbamate 6-1.

Scheme 7

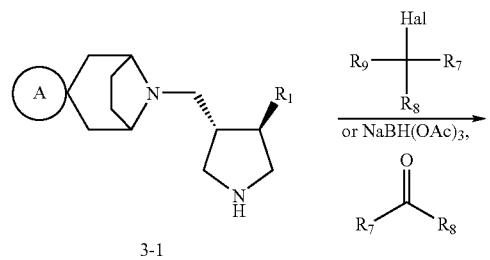

3-1

-continued

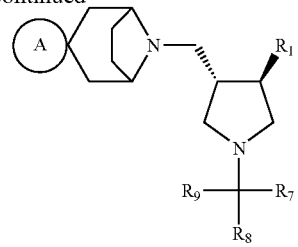

7-1

General procedure: the pyrrolidine 3-1 is reacted with halogenoalkyl derivative $r_7R_8R_9CHal$ in solvents such as DMF or DMA at temperature ranged from 25 to 100° C. using an inorganic base such as $Na_2CO_3$, $K_2CO_3$ or $Cs_2CO_3$, or condensed with aldehyde or ketone using conventional reductive amination reaction condition (see Abdel-Magid A. F. et al. *J. Org. Chem.* 1996, 61, 3849-3862) to provide the amine 7-1.

Table 4 of compounds illustrates some of the compounds of the present invention which could be synthesized using the synthetic schemes and the procedures described herein.

TABLE 1

| CPD # | STRUCTURE | COMPOUND NAME | MW |
|---|---|---|---|
| 1 | 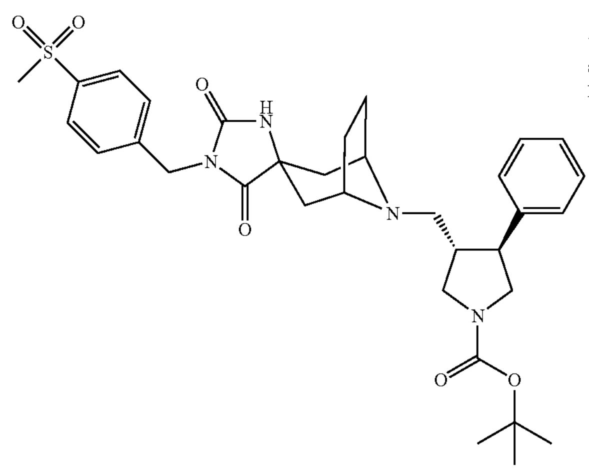 | (3S,4S)-3-[3-(4-Methanesulfonylbenzyl)-bicyclo[3.2.1]-2,4-dioxo-1α,3,8-triaza-spiro[4.5]dodec-8-ylmethyl]-4-phenyl-pyrrolidine-1-carboxylic acid tert-butyl ester | 659.24 |
| 2 | 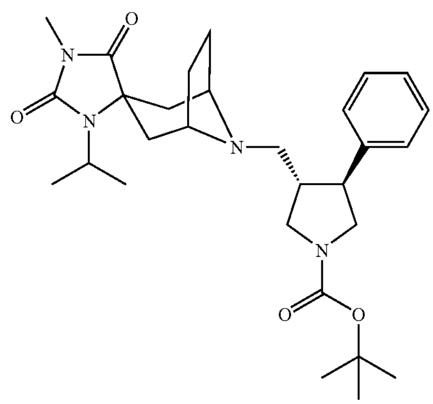 | (3S,4S)-3-[1-Isopropyl-3-methyl-bicyclo[3.2.1]-2,4-dioxo-1β,3,8-triaza-spiro[4.5]dodec-8-ylmethyl]-4-phenyl-pyrrolidine-1-carboxylic acid tert-butyl ester | 510.68 |

TABLE 1-continued

| CPD # | STRUCTURE | COMPOUND NAME | MW |
|---|---|---|---|
| 3 | Chiral | (3S,4S)-3-[3-Ethyl-1-isopropyl-bicyclo[3.2.1]-2,4-dioxo-1β,3,8-triaza-spiro[4.5]dodec-8-ylmethyl]-4-phenyl-pyrrolidine-1-carboxylic acid tert-butyl ester | 524.71 |
| 4 | 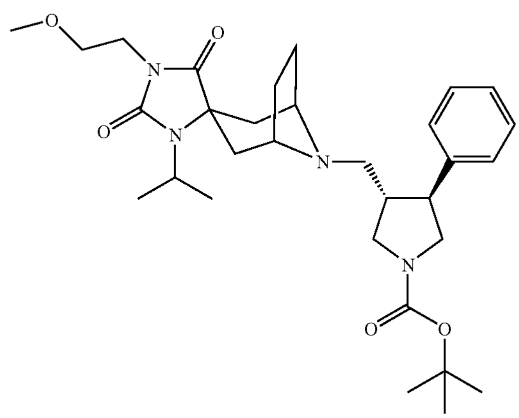 | (3S,4S)-3-[1-Isopropyl-3-(2-methoxy-ethyl)-bicyclo[3.2.1]-2,4-dioxo-1β,3,8-triaza-spiro[4.5]dodec-8-ylmethyl]-4-phenyl-pyrrolidine-1-carboxylic acid tert-butyl ester | 554.74 |
| 5 | 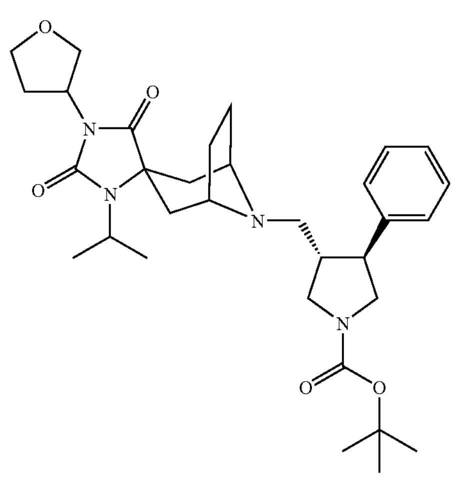 | (3S,4S)-3-[1-Isopropyl-3-(tetrahydrofuran-3-yl)-bicyclo[3.2.1]-2,4-dioxo-1β,3,8-triaza-spiro[4.5]dodec-8-ylmethyl]-4-phenyl-pyrrolidine-1-carboxylic acid tert-butyl ester | 566.75 |

TABLE 1-continued

| CPD # | STRUCTURE | COMPOUND NAME | MW |
|---|---|---|---|
| 6 | 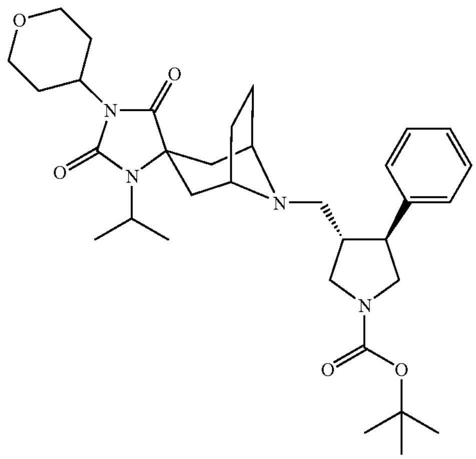 | (3S,4S)-3-[1-Isopropyl-3-(tetrahydropyran-4-yl)-bicyclo[3.2.1]-2,4-dioxo-1β,3,8-triaza-spiro[4.5]dodec-8-ylmethyl]-4-phenyl-pyrrolidine-1-carboxylic acid tert-butyl ester | 580.77 |
| 7 | 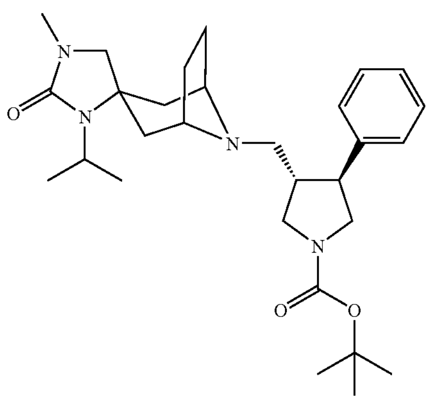 | (3S,4S)-3-[1-Isopropyl-3-methyl-bicyclo[3.2.1]-2-oxo-1β,3,8-triaza-spiro[4.5]dodec-8-ylmethyl]-4-phenyl-pyrrolidine-1-carboxylic acid tert-butyl ester | 496.70 |
| 8 | 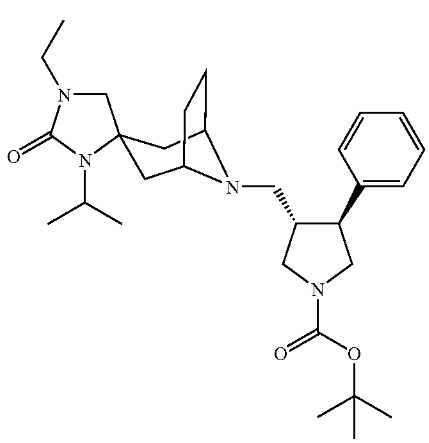 | (3S,4S)-3-[3-Ethyl-1-isopropyl-bicyclo[3.2.1]-2-oxo-1β,3,8-triaza-spiro[4.5]dodec-8-ylmethyl]-4-phenyl-pyrrolidine-1-carboxylic acid tert-butyl ester | 510.73 |

TABLE 1-continued

| CPD # | STRUCTURE | COMPOUND NAME | MW |
|---|---|---|---|
| 9 | 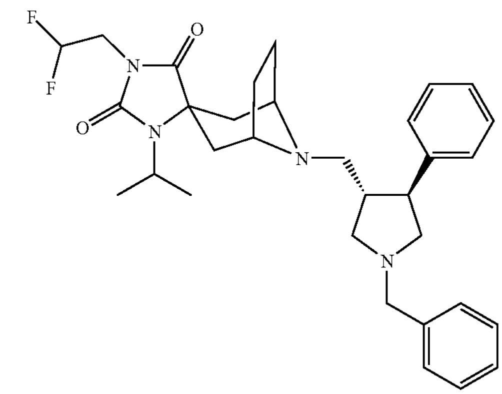 | (3S,4S)-1-benzyl-3-[3-(2,2-Difluoro-ethyl)-1-isopropyl-bicyclo[3.2.1]-2,4-dioxo-1β,3,8-triaza-spiro[4.5]dodec-8-ylmethyl]-4-phenyl-pyrrolidine | 550.7 |
| 10 | 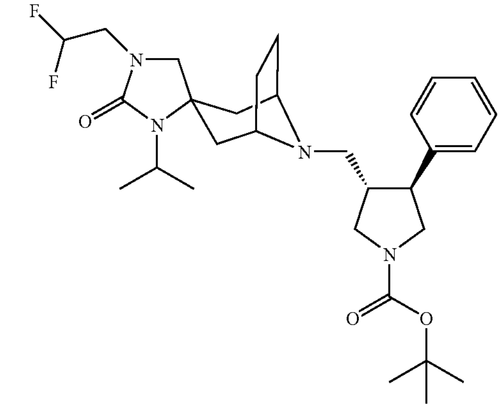 | (3S,4S)-3-[3-(2,2-Difluoro-ethyl)-1-isopropyl-bicyclo[3.2.1]-2-oxo-1β,3,8-triaza-spiro[4.5]dodec-8-ylmethyl]-4-phenyl-pyrrolidine-1-carboxylic acid tert-butyl ester | 546.71 |
| 11 | 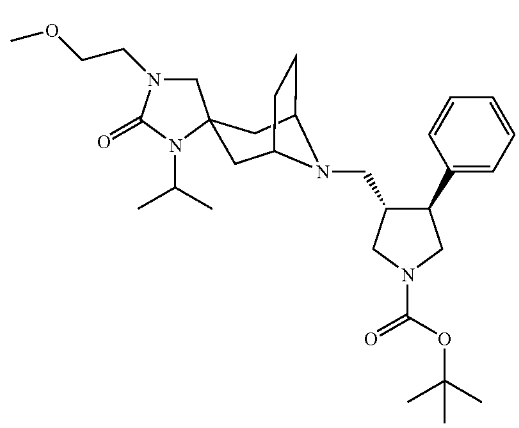 | (3S,4S)-3-[1-Isopropyl-3-(2-methoxy-ethyl)-bicyclo[3.2.1]-2-oxo-1β,3,8-triaza-spiro[4.5]dodec-8-ylmethyl]-4-phenyl-pyrrolidine-1-carboxylic acid tert-butyl ester | 540.75 |

TABLE 1-continued

| CPD # | STRUCTURE | COMPOUND NAME | MW |
|---|---|---|---|
| 12 | 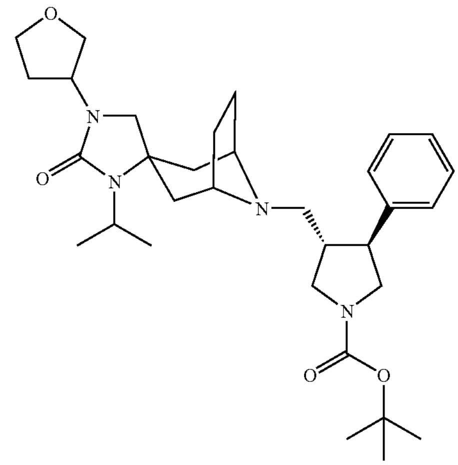 | (3S,4S)-3-[1-Isopropyl-3-(tetrahydrofuran-3-yl)-bicyclo[3.2.1]-2-oxo-1β,3,8-triaza-spiro[4.5]dodec-8-ylmethyl]-4-phenyl-pyrrolidine-1-carboxylic acid tert-butyl ester | 552.76 |
| 13 | 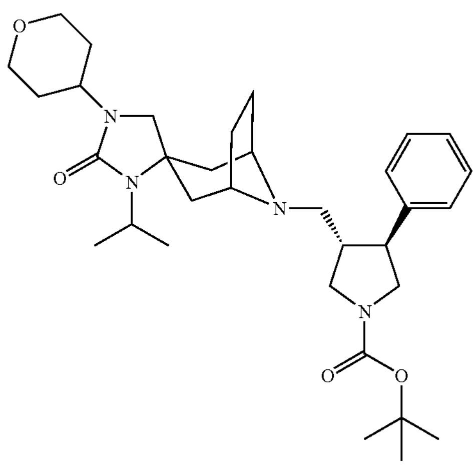 | (3S,4S)-3-[1-Isopropyl-3-(tetrahydropyran-4-yl)-bicyclo[3.2.1]-2-oxo-1β,3,8-triaza-spiro[4.5]dodec-8-ylmethyl]-4-phenyl-pyrrolidine-1-carboxylic acid tert-butyl ester | 566.79 |
| 14 | 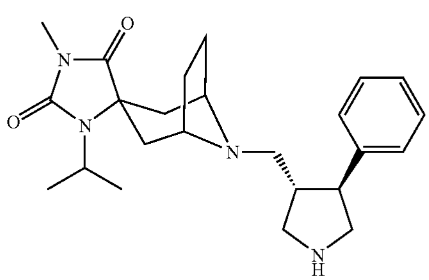 | (3R,4S)-3-[1-Isopropyl-3-methyl-bicyclo[3.2.1]-2,4-dioxo-1β,3,8-triaza-spiro[4.5]dodec-8-ylmethyl]-4-phenyl-pyrrolidine | 410.56 |
| 15 | Chiral | (3R,4S)-3-[3-Ethyl-1-isopropyl-bicyclo[3.2.1]-2,4-dioxo-1β,3,8-triaza-spiro[4.5]dodec-8-ylmethyl]-4-phenyl-pyrrolidine | 424.59 |

TABLE 1-continued

| CPD # | STRUCTURE | COMPOUND NAME | MW |
|---|---|---|---|
| 16 | 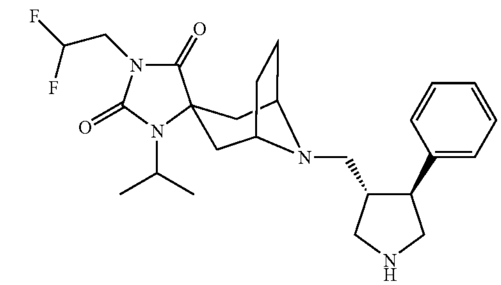 | (3R,4S)-3-[3-(2,2-Difluoro-ethyl)-1-isopropyl-bicyclo[3.2.1]-2,4-dioxo-1β,3,8-triaza-spiro[4.5]dodec-8-ylmethyl]-4-phenyl-pyrrolidine | 460.57 |
| 17 | 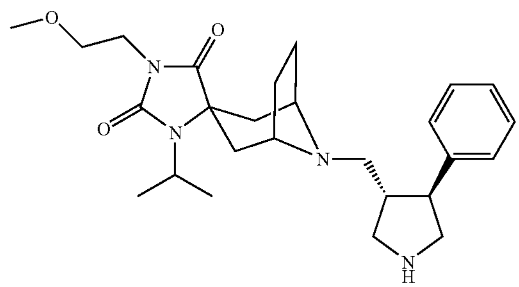 | (3R,4S)-3-[1-Isopropyl-3-(2-methoxy-ethyl)-bicyclo[3.2.1]-2,4-dioxo-1β,3,8-triaza-spiro[4.5]dodec-8-ylmethyl]-4-phenyl-pyrrolidine | 454.62 |
| 18 | 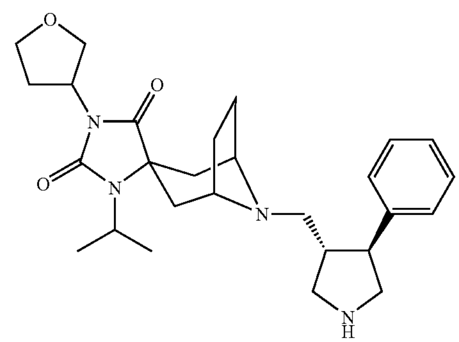 | (3R,4S)-3-[1-Isopropyl-3-(tetrahydrofuran-3-yl)-bicyclo[3.2.1]-2,4-dioxo-1β,3,8-triaza-spiro[4.5]dodec-8-ylmethyl]-4-phenyl-pyrrolidine | 466.63 |
| 19 | 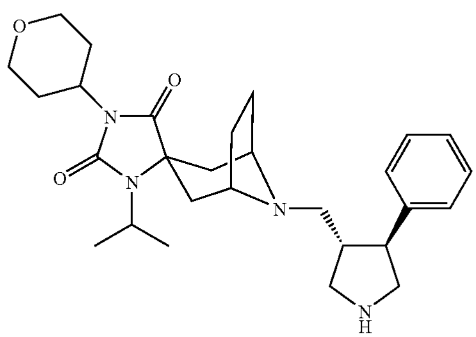 | (3R,4S)-3-[1-Isopropyl-3-(tetrahydropyran-4-yl)-bicyclo[3.2.1]-2,4-dioxo-1β,3,8-triaza-spiro[4.5]dodec-8-ylmethyl]-4-phenyl-pyrrolidine | 480.66 |
| 20 | 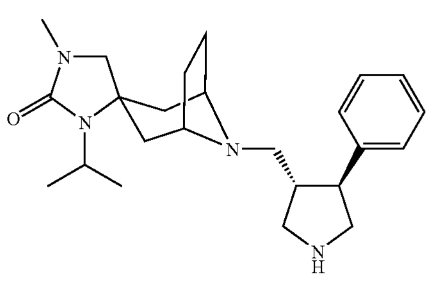 | (3R,4S)-3-[1-Isopropyl-3-methyl-bicyclo[3.2.1]-2-oxo-1β,3,8-triaza-spiro[4.5]dodec-8-ylmethyl]-4-phenyl-pyrrolidine | 396.58 |

TABLE 1-continued

| CPD # | STRUCTURE | COMPOUND NAME | MW |
|---|---|---|---|
| 21 | 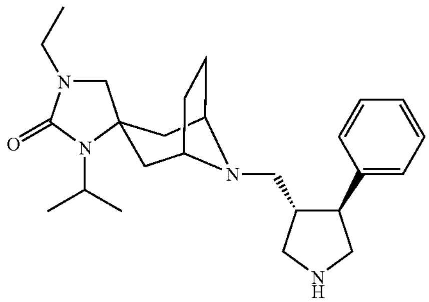 | (3R,4S)-3-[3-Ethyl-1-isopropyl-bicyclo[3.2.1]-2-oxo-1β,3,8-triaza-spiro[4.5]dodec-8-ylmethyl]-4-phenyl-pyrrolidine | 410.61 |
| 22 | 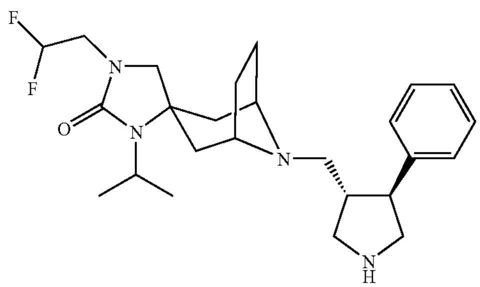 | (3R,4S)-3-[3-(2,2-Difluoro-ethyl)-1-isopropyl-bicyclo[3.2.1]-2-oxo-1β,3,8-triaza-spiro[4.5]dodec-8-ylmethyl]-4-phenyl-pyrrolidine | 446.59 |
| 23 | 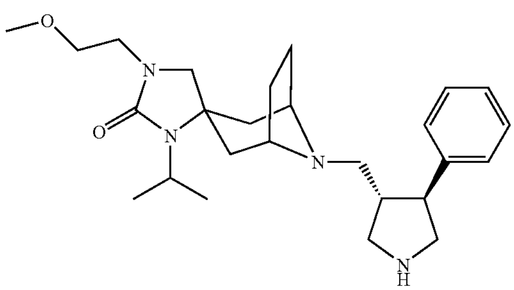 | (3R,4S)-3-[1-Isopropyl-3-(2-methoxy-ethyl)-bicyclo[3.2.1]-2-oxo-1β,3,8-triaza-spiro[4.5]dodec-8-ylmethyl]-4-phenyl-pyrrolidine | 440.63 |
| 24 | 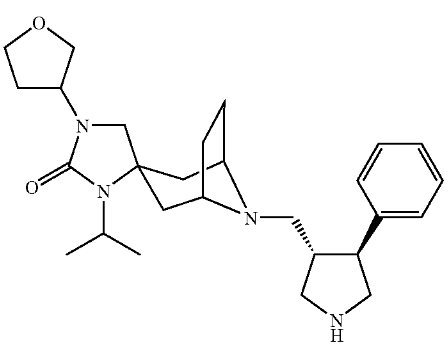 | (3R,4S)-3-[1-Isopropyl-3-(tetrahydrofuran-3-yl)-bicyclo[3.2.1]-2-oxo-1β,3,8-triaza-spiro[4.5]dodec-8-ylmethyl]-4-phenyl-pyrrolidine | 452.65 |
| 25 | 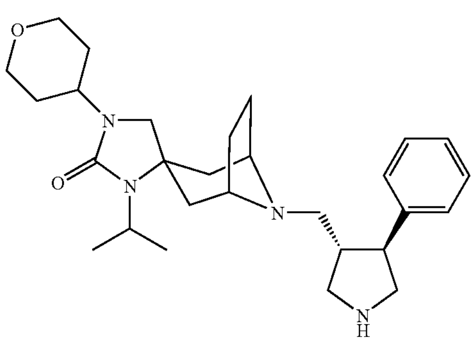 | (3R,4S)-3-[1-Isopropyl-3-(tetrahydropyran-4-yl)-bicyclo[3.2.1]-2-oxo-1β,3,8-triaza-spiro[4.5]dodec-8-ylmethyl]-4-phenyl-pyrrolidine | 466.67 |

TABLE 2

| CPD # | STRUCTURE | COMPOUND NAME | MW |
|---|---|---|---|
| 26 | 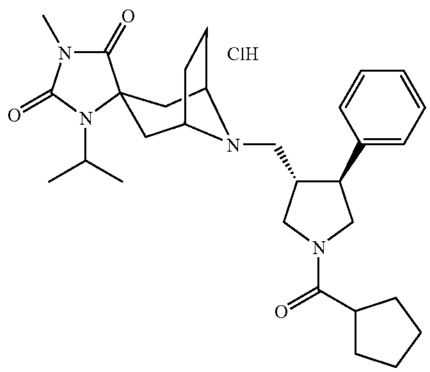 | (3S,4S)-1-Cyclopentanecarbonyl-3-[1-isopropyl-3-methyl-bicyclo[3.2.1]-2,4-dioxo-1β,3,8-triaza-spiro[4.5]dodec-8-ylmethyl]-4-phenyl-pyrrolidine hydrochloride | 543.14 |
| 27 | 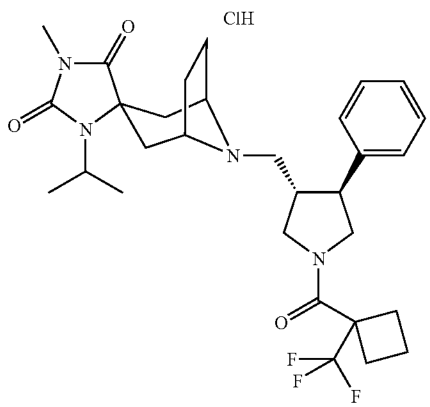 | (3S,4S)-1-(1-Trifluoromethyl-cyclobutanecarbonyl)-3-[1-isopropyl-3-methyl-bicyclo[3.2.1]-2,4-dioxo-1β,3,8-triaza-spiro[4.5]dodec-8-ylmethyl]-4-phenyl-pyrrolidine hydrochloride | 597.11 |
| 28 | 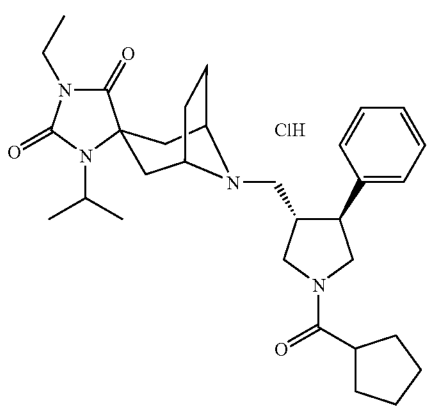 | (3S,4S)-1-Cyclopentanecarbonyl-3-[3-ethyl-1-isopropyl-bicyclo[3.2.1]-2,4-dioxo-1β,3,8-triaza-spiro[4.5]dodec-8-ylmethyl]-4-phenyl-pyrrolidine hydrochloride | 557.18 |

TABLE 2-continued

| CPD # | STRUCTURE | COMPOUND NAME | MW |
|---|---|---|---|
| 29 | 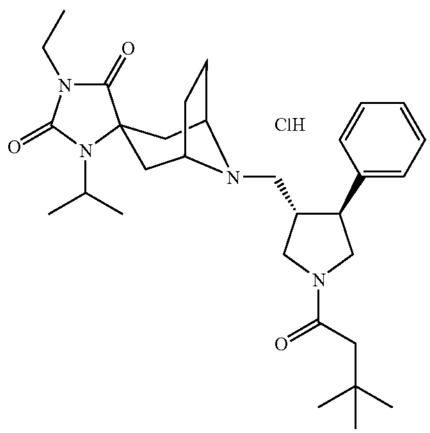 | (3S,4S)-1-(3,3-Dimethyl-butyryl)-3-[3-ethyl-1-isopropyl-bicyclo[3.2.1]-2,4-dioxo-1β,3,8-triaza-spiro[4.5]dodec-8-ylmethyl]-4-phenyl-pyrrolidine hydrochloride | 559.2 |
| 30 | 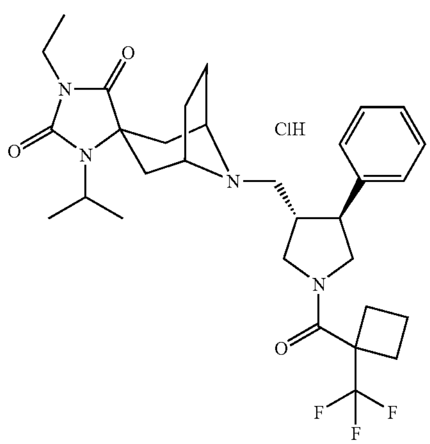 | (3S,4S)-1-(1-Trifluoromethyl-cyclobutanecarbonyl)-3-[3-ethyl-1-isopropyl-bicyclo[3.2.1]-2,4-dioxo-1β,3,8-triaza-spiro[4.5]dodec-8-ylmethyl]-4-phenyl-pyrrolidine hydrochloride | 611.15 |
| 31 | 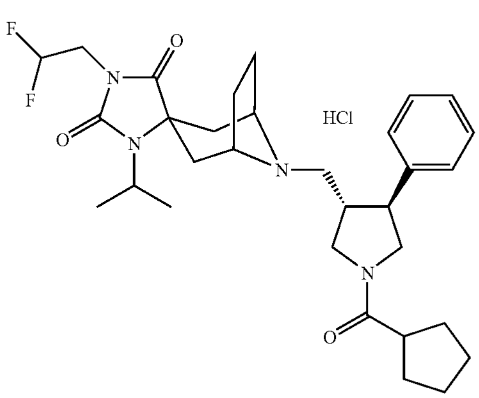 | (3S,4S)-1-Cyclopentanecarbonyl-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine hydrochloride | 593.16 |

TABLE 2-continued

| CPD # | STRUCTURE | COMPOUND NAME | MW |
|---|---|---|---|
| 32 | 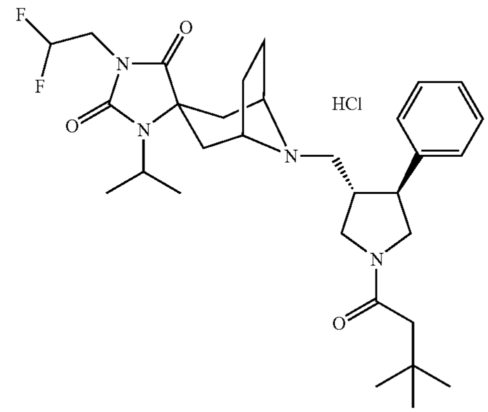 | (3S,4S)-1-(3,3-Dimethyl-butyryl)-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine hydrochloride | 595.18 |
| 33 | 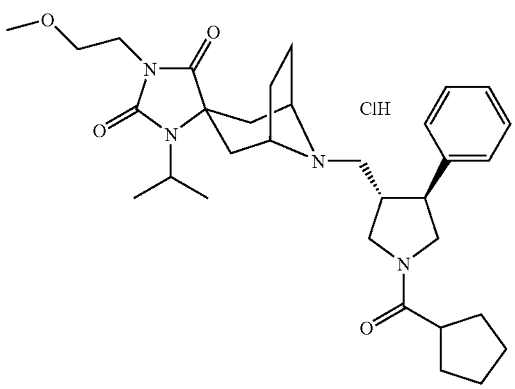 | (3S,4S)-1-Cyclopentanecarbonyl-3-[-1-isopropyl-3-(2-methoxy-ethyl)-bicyclo[3.2.1]-2,4-dioxo-1β,3,8-triaza-spiro[4.5]dodec-8-ylmethyl]-4-phenyl-pyrrolidine hydrochloride | 587.21 |
| 34 | 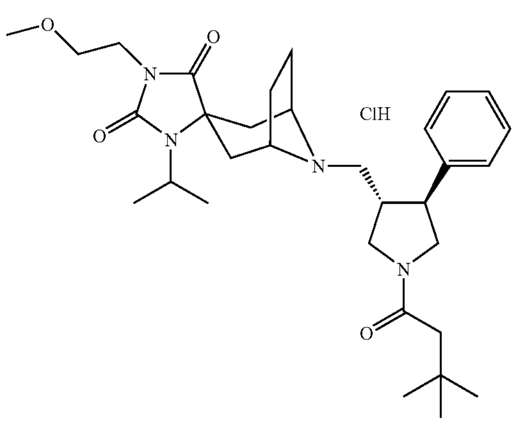 | (3S,4S)-1-(3,3-Dimethyl-butyryl)-3-[1-isopropyl-3-(2-methoxy-ethyl)-bicyclo[3.2.1]-2,4-dioxo-1β,3,8-triaza-spiro[4.5]dodec-8-ylmethyl]-4-phenyl-pyrrolidine hydrochloride | 589.22 |

TABLE 2-continued

| CPD # | STRUCTURE | COMPOUND NAME | MW |
|---|---|---|---|
| 35 | 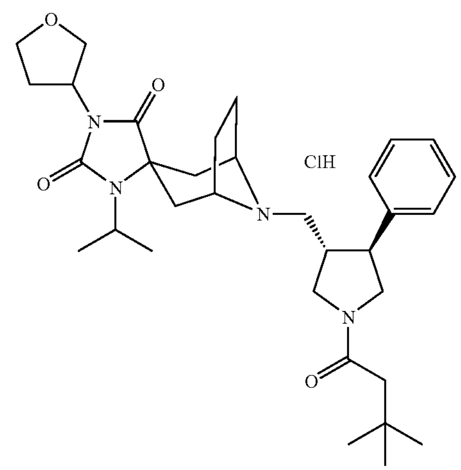 | (3S,4S)-1-(3,3-Dimethyl-butyryl)-3-[1-isopropyl-3-(tetrahydro-furan-3-yl)-bicyclo[3.2.1]-2,4-dioxo-1β,3,8-triaza-spiro[4.5]dodec-8-ylmethyl]-4-phenyl-pyrrolidine hydrochloride | 601.23 |
| 36 | 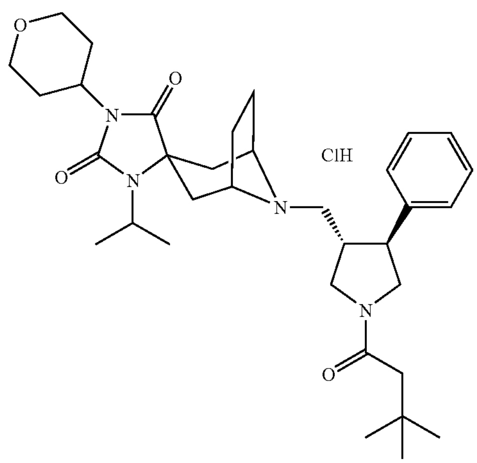 | (3S,4S)-1-(3,3-Dimethyl-butyryl)-3-[1-isopropyl-3-(tetrahydro-pyran-4-yl)-bicyclo[3.2.1]-2,4-dioxo-1β,3,8-triaza-spiro[4.5]dodec-8-ylmethyl]-4-phenyl-pyrrolidine hydrochloride | 615.26 |
| 37 | 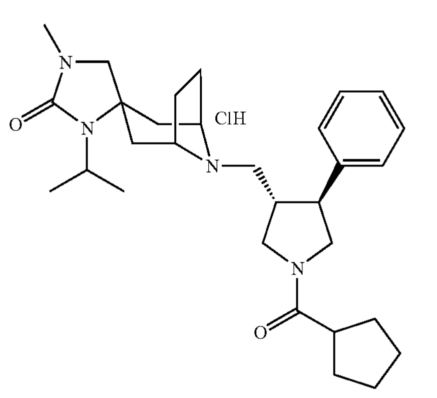 | (3S,4S)-1-Cyclopentanecarbonyl-3-[1-isopropyl-3-methyl-bicyclo[3.2.1]-2-oxo-1β,3,8-triaza-spiro[4.5]dodec-8-ylmethyl]-4-phenyl-pyrrolidine hydrochloride | 529.16 |

TABLE 2-continued

| CPD # | STRUCTURE | COMPOUND NAME | MW |
|---|---|---|---|
| 38 | 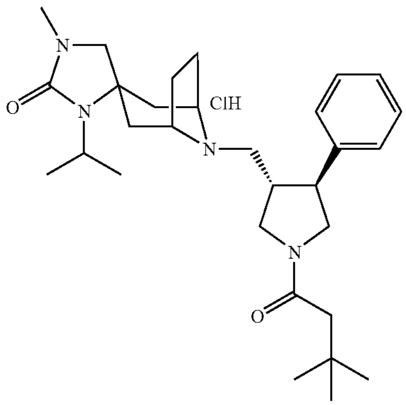 | (3S,4S)-1-(3,3-Dimethyl-butyryl)-3-[1-isopropyl-3-methyl-bicyclo[3.2.1]-2-oxo-1β,3,8-triaza-spiro[4.5]dodec-8-ylmethyl]-4-phenyl-pyrrolidine hydrochloride | 531.18 |
| 39 | 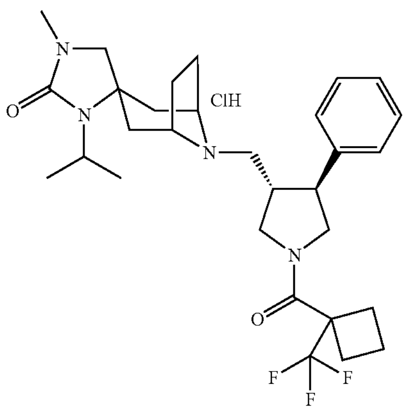 | (3S,4S)-1-(1-Trifluoromethyl-cyclobutanecarbonyl)-3-[1-isopropyl-3-methyl-bicyclo[3.2.1]-2-oxo-1β,3,8-triaza-spiro[4.5]dodec-8-ylmethyl]-4-phenyl-pyrrolidine hydrochloride | 583.13 |
| 40 | 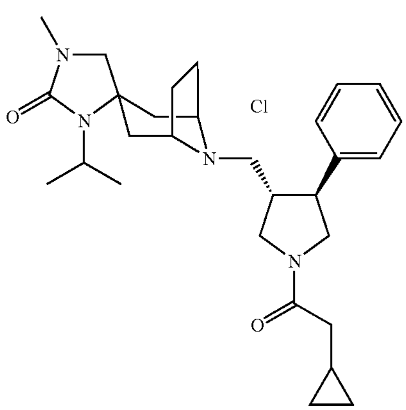 | (3S,4S)-1-(2-Cyclopropyl-acetyl)-3-[1-isopropyl-3-methyl-bicyclo[3.2.1]-2-oxo-1β,3,8-triaza-spiro[4.5]dodec-8-ylmethyl]-4-phenyl-pyrrolidine hydrochloride | 515.13 |
| 41 | 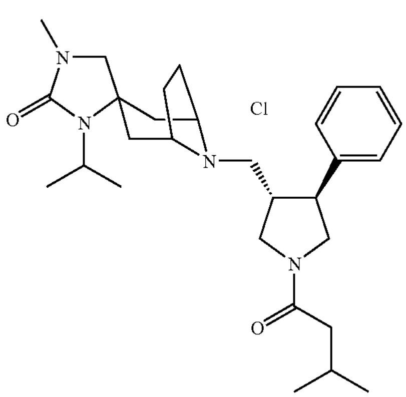 | (3S,4S)-1-(3-Methyl-butyryl)-3-[1-isopropyl-3-methyl-bicyclo[3.2.1]-2-oxo-1β,3,8-triaza-spiro[4.5]dodec-8-ylmethyl]-4-phenyl-pyrrolidine hydrochloride | 517.15 |

TABLE 2-continued

| CPD # | STRUCTURE | COMPOUND NAME | MW |
|---|---|---|---|
| 42 | 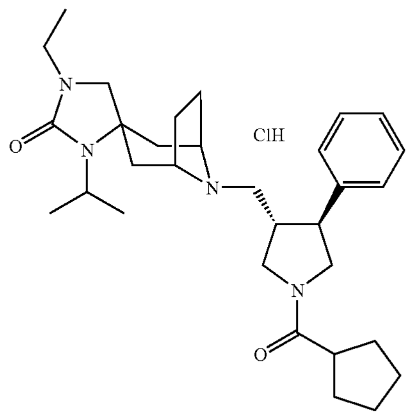 | (3S,4S)-1-Cyclopentanecarbonyl-3-[3-ethyl-1-isopropyl-bicyclo[3.2.1]-2-oxo-1β,3,8-triaza-spiro[4.5]dodec-8-ylmethyl]-4-phenyl-pyrrolidine hydrochloride | 543.2 |
| 43 | 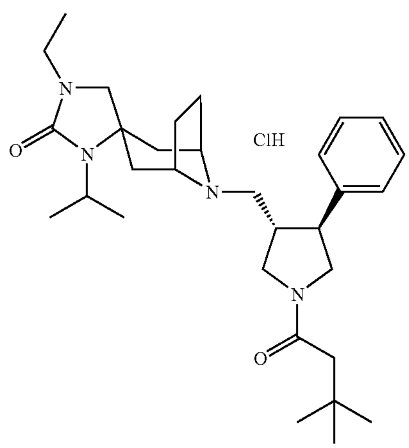 | (3S,4S)-1-(3,3-Dimethyl-butyryl)-3-[3-ethyl-1-isopropyl-bicyclo[3.2.1]-2-oxo-1β,3,8-triaza-spiro[4.5]dodec-8-ylmethyl]-4-phenyl-pyrrolidine hydrochloride | 545.21 |
| 44 | 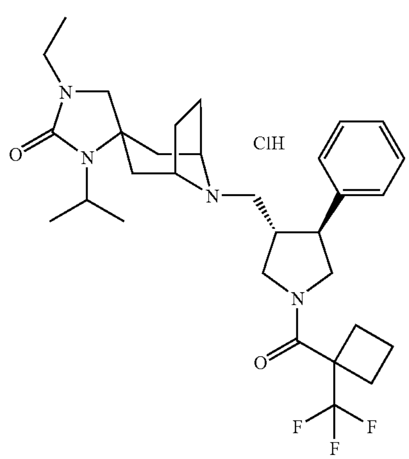 | (3S,4S)-1-(1-Trifluoromethyl-cyclobutanecarbonyl)-3-[3-ethyl-1-isopropyl-bicyclo[3.2.1]-2-oxo-1β,3,8-triaza-spiro[4.5]dodec-8-ylmethyl]-4-phenyl-pyrrolidine hydrochloride | 597.17 |

TABLE 2-continued

| CPD # | STRUCTURE | COMPOUND NAME | MW |
|---|---|---|---|
| 45 | 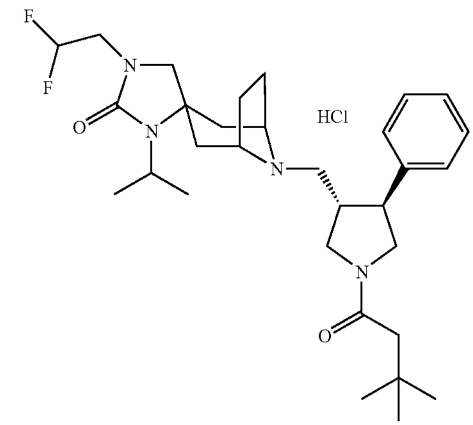 | (3S,4S)-1-(3,3-Dimethyl-butyryl)-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine hydrochloride | 581.19 |
| 46 | 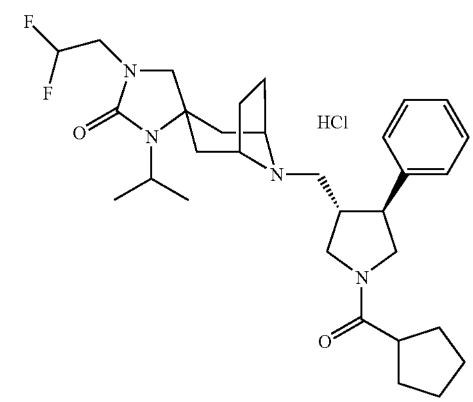 | (3S,4S)-1-Cyclopentanecarbonyl-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine hydrochloride | 579.18 |
| 47 | 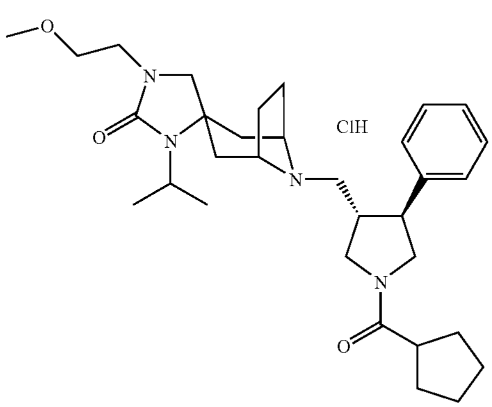 | (3S,4S)-1-Cyclopentanecarbonyl-3-[-1-isopropyl-3-(2-methoxy-ethyl)-bicyclo[3.2.1]-2-oxo-1β,3,8-triaza-spiro[4.5]dodec-8-ylmethyl]-4-phenyl-pyrrolidine hydrochloride | 573.22 |

TABLE 2-continued

| CPD # | STRUCTURE | COMPOUND NAME | MW |
|---|---|---|---|
| 48 | 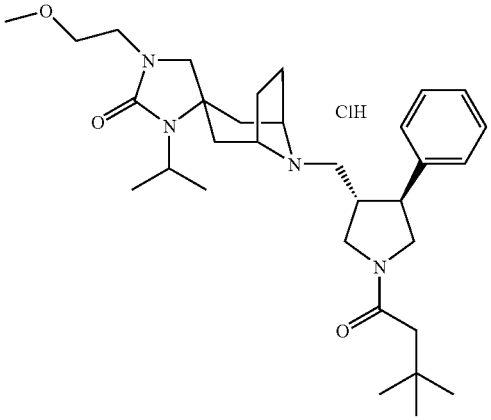 | (3S,4S)-1-(3,3-Dimethyl-butyryl)-3-[1-isopropyl-3-(2-methoxy-ethyl)-bicyclo[3.2.1]-2-oxo-1β,3,8-triaza-spiro[4.5]dodec-8-ylmethyl]-4-phenyl-pyrrolidine hydrochloride | 575.24 |
| 49 | 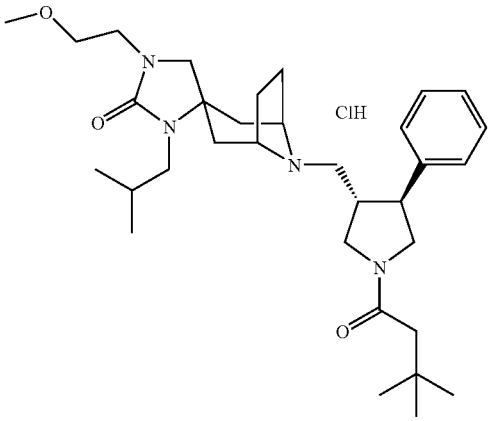 | (3S,4S)-1-(3,3-Dimethyl-butyryl)-3-[1-isobutyl-3-(2-methoxy-ethyl)-bicyclo[3.2.1]-2-oxo-1β,3,8-triaza-spiro[4.5]dodec-8-ylmethyl]-4-phenyl-pyrrolidine hydrochloride | 589.25 |
| 50 | 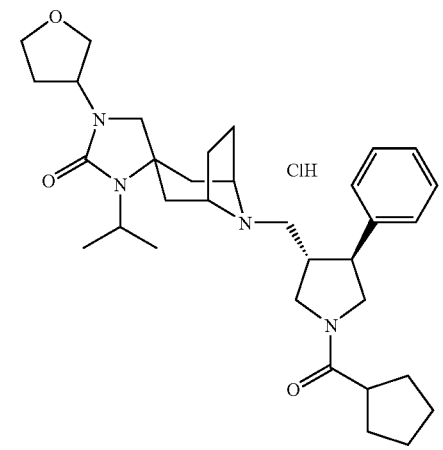 | (3S,4S)-1-Cyclopentanecarbonyl-3-[-1-isopropyl-3-(tetrahydro-furan-3-yl)-bicyclo[3.2.1]-2-oxo-1β,3,8-triaza-spiro[4.5]dodec-8-ylmethyl]-4-phenyl-pyrrolidine hydrochloride | 585.24 |

TABLE 2-continued

| CPD # | STRUCTURE | COMPOUND NAME | MW |
|---|---|---|---|
| 51 | 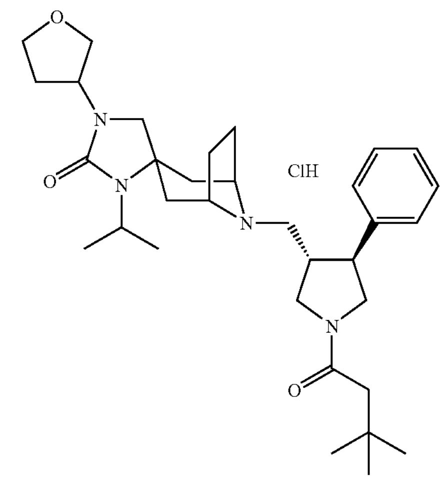 | (3S,4S)-1-(3,3-Dimethyl-butyryl)-3-[1-isopropyl-3-(tetrahydro-furan-3-yl)-bicyclo[3.2.1]-2-oxo-1β,3,8-triaza-spiro[4.5]dodec-8-ylmethyl]-4-phenyl-pyrrolidine hydrochloride | 587.25 |
| 52 | 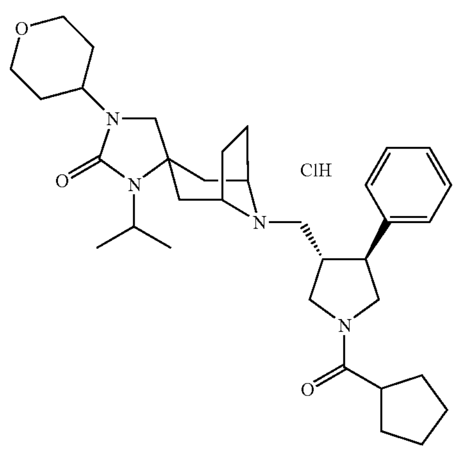 | (3S,4S)-1-Cyclopentanecarbonyl-3-[-1-isopropyl-3-(tetrahydro-pyran-4-yl)-bicyclo[3.2.1]-2-oxo-1β,3,8-triaza-spiro[4.5]dodec-8-ylmethyl]-4-phenyl-pyrrolidine hydrochloride | 599.26 |
| 53 | 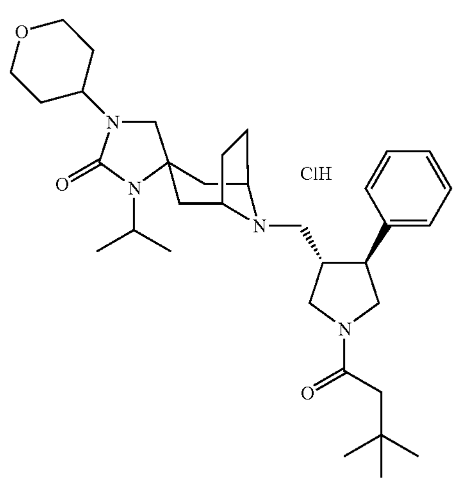 | (3S,4S)-1-(3,3-Dimethyl-butyryl)-3-[1-isopropyl-3-(tetrahydro-pyran-4-yl)-bicyclo[3.2.1]-2-oxo-1β,3,8-triaza-spiro[4.5]dodec-8-ylmethyl]-4-phenyl-pyrrolidine hydrochloride | 601.28 |

TABLE 3

| CPD # | STRUCTURE | COMPOUND NAME | MW |
|---|---|---|---|
| 54 | 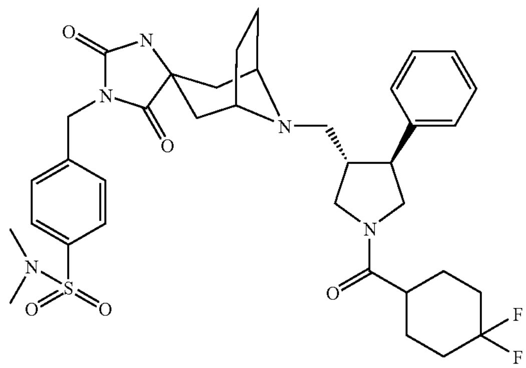 | (3S,4S)-1-(4,4-Difluoro-cyclohexanecarbonyl)-3-[3-(4-N,N-dimethyl-benzenesulfonamide)-bicyclo[3.2.1]-2,4-dioxo-1α,3,8-triaza-spiro[4.5]dodec-8-ylmethyl]-4-phenyl-pyrrolidine | 697.85 |
| 55 | 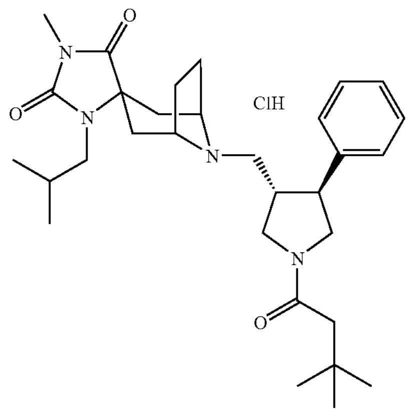 | (3S,4S)-1-(3,3-Dimethyl-butyryl)-3-[1-isobutyl-3-methyl-bicyclo[3.2.1]-2,4-dioxo-1β,3,8-triaza-spiro[4.5]dodec-8-ylmethyl]-4-phenyl-pyrrolidine hydrochloride | 559.19 |
| 56 | 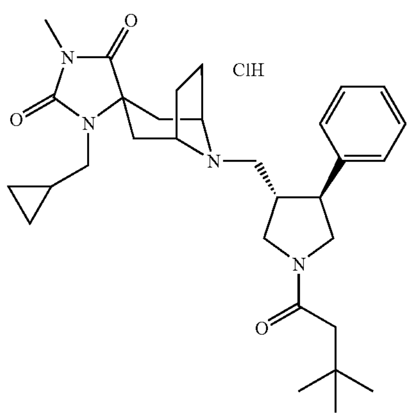 | (3S,4S)-1-(3,3-Dimethyl-butyryl)-3-[1-cyclopropylmethyl-3-methyl-bicyclo[3.2.1]-2,4-dioxo-1β,3,8-triaza-spiro[4.5]dodec-8-ylmethyl]-4-phenyl-pyrrolidine hydrochloride | 557.17 |
| 57 | 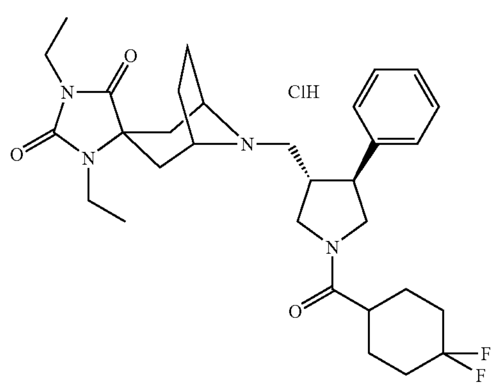 | (3S,4S)-1-(4,4-Difluoro-cyclohexanecarbonyl)-3-[1,3-diethyl-bicyclo[3.2.1]-2,4-dioxo-1β,3,8-triaza-spiro[4.5]dodec-8-ylmethyl]-4-phenyl-pyrrolidine hydrochloride | 593.15 |

TABLE 3-continued

| CPD # | STRUCTURE | COMPOUND NAME | MW |
|---|---|---|---|
| 58 | 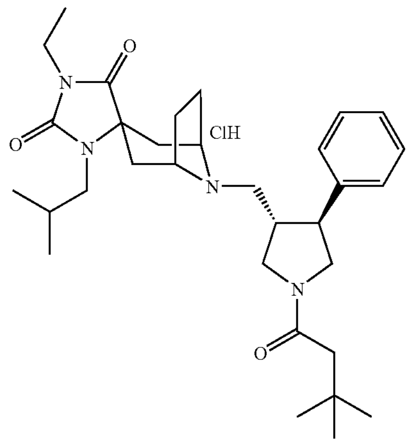 | (3S,4S)-1-(3,3-Dimethyl-butyryl)-3-[3-ethyl-1-isobutyl-bicyclo[3.2.1]-2,4-dioxo-1β,3,8-triaza-spiro[4.5]dodec-8-ylmethyl]-4-phenyl-pyrrolidine hydrochloride | 573.21 |
| 59 | 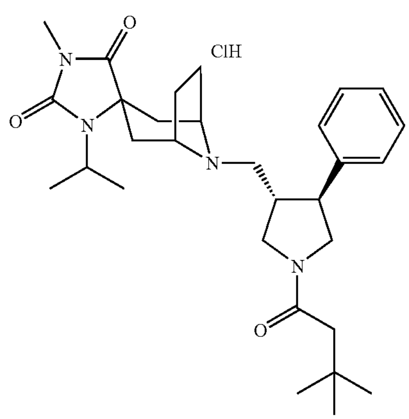 | (3S,4S)-1-(3,3-Dimethyl-butyryl)-3-[1-isopropyl-3-methyl-bicyclo[3.2.1]-2,4-dioxo-1β,3,8-triaza-spiro[4.5]dodec-8-ylmethyl]-4-phenyl-pyrrolidine hydrochloride | 545.16 |
| 60 | 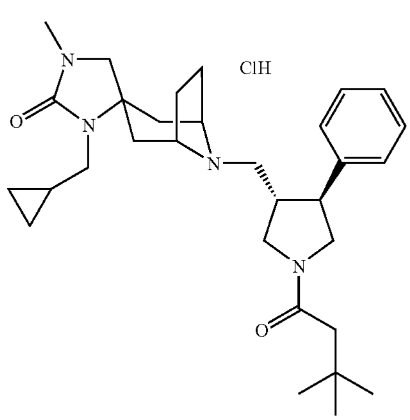 | (3S,4S)-1-(3,3-Dimethyl-butyryl)-3-[1-cyclopropylmethyl-3-methyl-bicyclo[3.2.1]-2-oxo-1β,3,8-triaza-spiro[4.5]dodec-8-ylmethyl]-4-phenyl-pyrrolidine hydrochloride | 543.19 |

TABLE 4

| CPD # | STRUCTURE | COMPOUND NAME | MW |
|---|---|---|---|
| 61 | 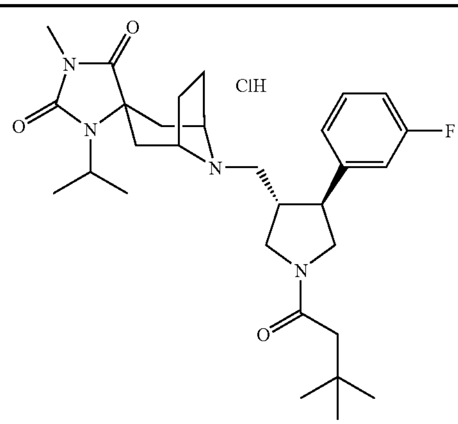 | (3S,4S)-1-(3,3-Dimethyl-butyryl)-3-[1-isopropyl-3-methyl-bicyclo[3.2.1]-2,4-dioxo-1β,3,8-triaza-spiro[4.5]dodec-8-ylmethyl]-4-(3-fluorophenyl)-pyrrolidine hydrochloride | 563.16 |
| 62 | 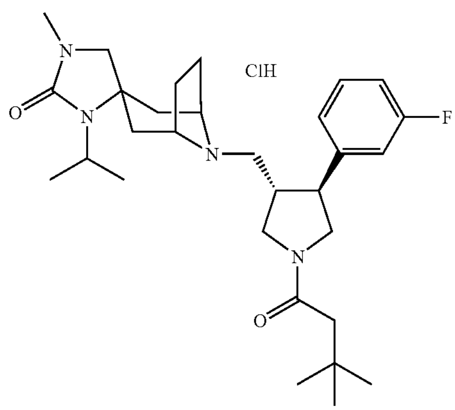 | (3S,4S)-1-(3,3-Dimethyl-butyryl)-3-[1-isopropyl-3-methyl-bicyclo[3.2.1]-2-oxo-1β,3,8-triaza-spiro[4.5]dodec-8-ylmethyl]-4-(3-fluorophenyl)-pyrrolidine hydrochloride | 549.18 |
| 63 | 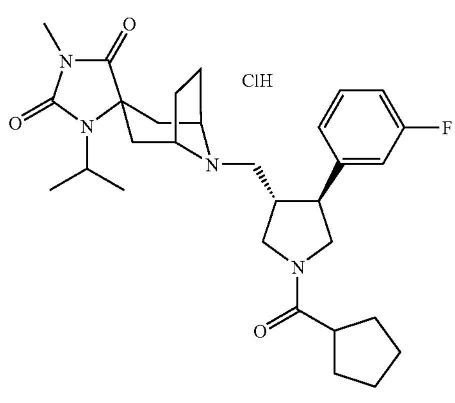 | (3S,4S)-1-Cyclopentanecarbonyl-3-[1-isopropyl-3-methyl-bicyclo[3.2.1]-2,4-dioxo-1β,3,8-triaza-spiro[4.5]dodec-8-ylmethyl]-4-(3-fluorophenyl)-pyrrolidine hydrochloride | 561.14 |
| 64 | 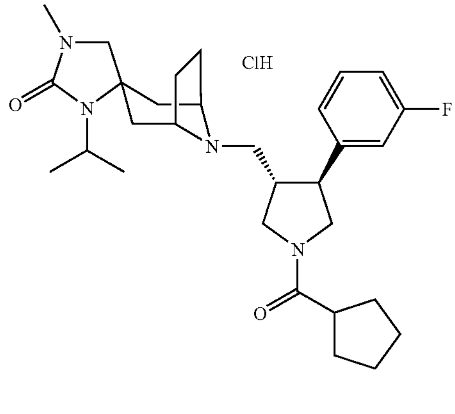 | (3S,4S)-1-Cyclopentanecarbonyl-3-[1-isopropyl-3-methyl-bicyclo[3.2.1]-2-oxo-1β,3,8-triaza-spiro[4.5]dodec-8-ylmethyl]-4-(3-fluorophenyl)-pyrrolidine hydrochloride | 547.16 |

TABLE 4-continued

| CPD # | STRUCTURE | COMPOUND NAME | MW |
|---|---|---|---|
| 65 | 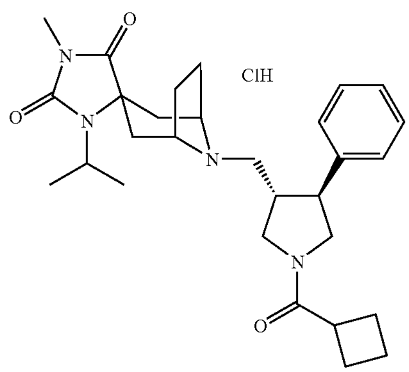 | (3S,4S)-1-Cyclobutanecarbonyl-3-[1-isopropyl-3-methyl-bicyclo[3.2.1]-2,4-dioxo-1β,3,8-triaza-spiro[4.5]dodec-8-ylmethyl]-4-phenyl-pyrrolidine hydrochloride | 529.13 |
| 66 | 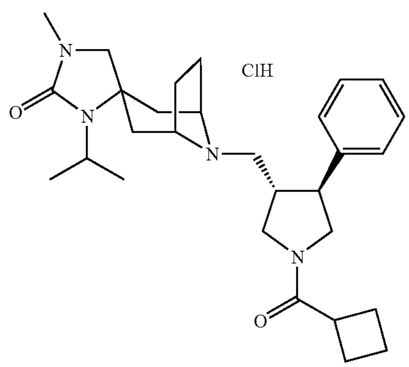 | (3S,4S)-1-Cyclobutanecarbonyl-3-[1-isopropyl-3-methyl-bicyclo[3.2.1]-2-oxo-1β,3,8-triaza-spiro[4.5]dodec-8-ylmethyl]-4-phenyl-pyrrolidine hydrochloride | 515.14 |
| 67 | 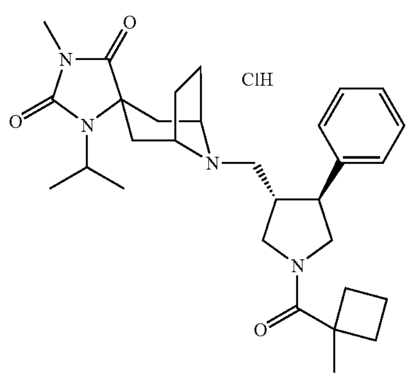 | (3S,4S)-1-(1-Methyl-cyclobutanecarbonyl)-3-[1-isopropyl-3-methyl-bicyclo[3.2.1]-2,4-dioxo-1β,3,8-triaza-spiro[4.5]dodec-8-ylmethyl]-4-phenyl-pyrrolidine hydrochloride | 543.15 |
| 68 | 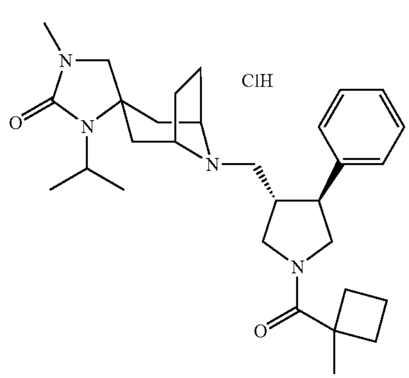 | (3S,4S)-1-(1-Methyl-cyclobutanecarbonyl)-3-[1-isopropyl-3-methyl-bicyclo[3.2.1]-2-oxo-1β,3,8-triaza-spiro[4.5]dodec-8-ylmethyl]-4-phenyl-pyrrolidine hydrochloride | 529.17 |

TABLE 4-continued

| CPD # | STRUCTURE | COMPOUND NAME | MW |
|---|---|---|---|
| 69 | 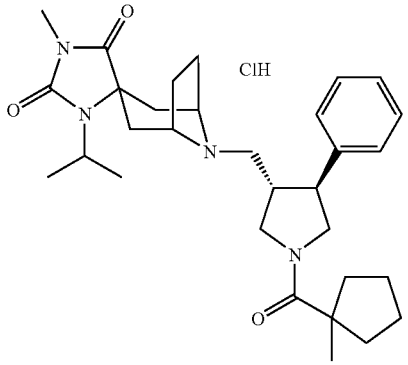 | (3S,4S)-1-(1-Methyl-cyclopentanecarbonyl)-3-[1-isopropyl-3-methyl-bicyclo[3.2.1]-2,4-dioxo-1β,3,8-triaza-spiro[4.5]dodec-8-ylmethyl]-4-phenyl-pyrrolidine hydrochloride | 557.18 |
| 70 | 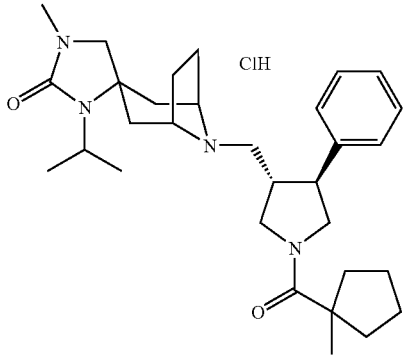 | (3S,4S)-1-(1-Methyl-cyclopentanecarbonyl)-3-[1-isopropyl-3-methyl-bicyclo[3.2.1]-2-oxo-1β,3,8-triaza-spiro[4.5]dodec-8-ylmethyl]-4-phenyl-pyrrolidine hydrochloride | 543.2 |
| 71 | 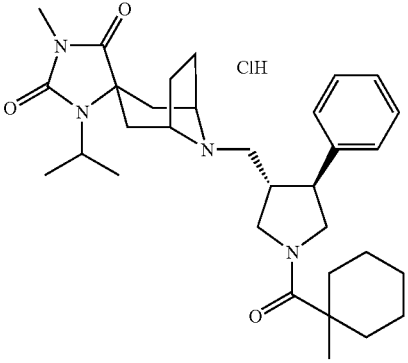 | (3S,4S)-1-(1-Methyl-cyclohexanecarbonyl)-3-[1-isopropyl-3-methyl-bicyclo[3.2.1]-2,4-dioxo-1β,3,8-triaza-spiro[4.5]dodec-8-ylmethyl]-4-phenyl-pyrrolidine hydrochloride | 571.21 |
| 72 | 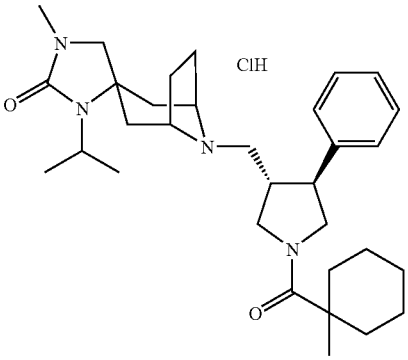 | (3S,4S)-1-(1-Methyl-cyclohexanecarbonyl)-3-[1-isopropyl-3-methyl-bicyclo[3.2.1]-2-oxo-1β,3,8-triaza-spiro[4.5]dodec-8-ylmethyl]-4-phenyl-pyrrolidine hydrochloride | 557.22 |

TABLE 4-continued

| CPD # | STRUCTURE | COMPOUND NAME | MW |
|---|---|---|---|
| 73 | 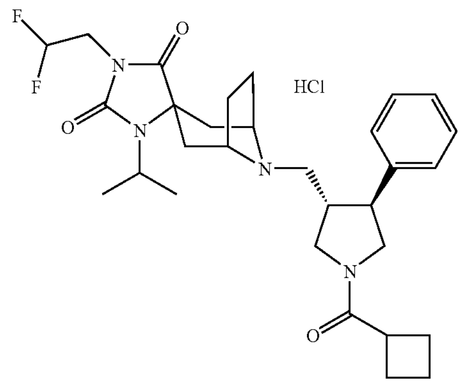 | (3S,4S)-1-Cyclobutanecarbonyl-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine hydrochloride | 579.14 |
| 74 | 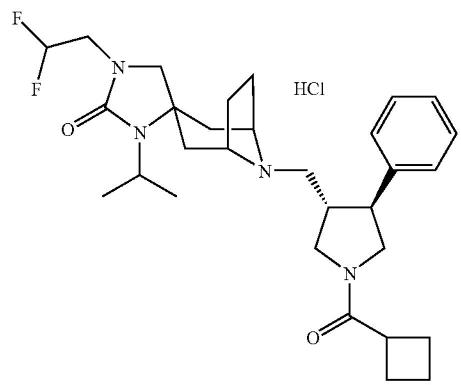 | (3S,4S)-1-Cyclobutanecarbonyl-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine hydrochloride | 565.15 |
| 75 | 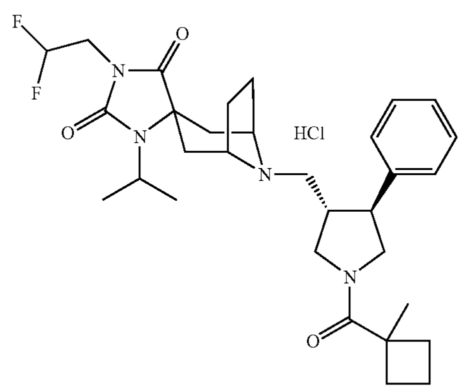 | (3S,4S)-1-(1-Methyl-cyclobutanecarbonyl)-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine hydrochloride | 593.16 |
| 76 | 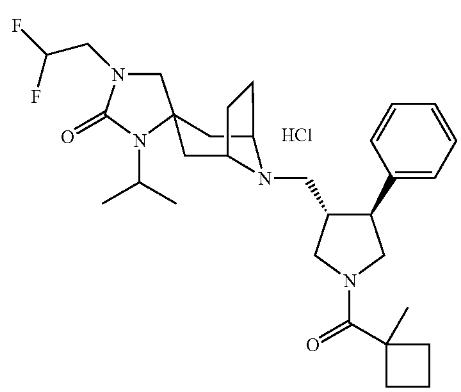 | (3S,4S)-1-(1-Methyl-cyclobutanecarbonyl)-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine hydrochloride | 579.18 |

TABLE 4-continued

| CPD # | STRUCTURE | COMPOUND NAME | MW |
|---|---|---|---|
| 77 | 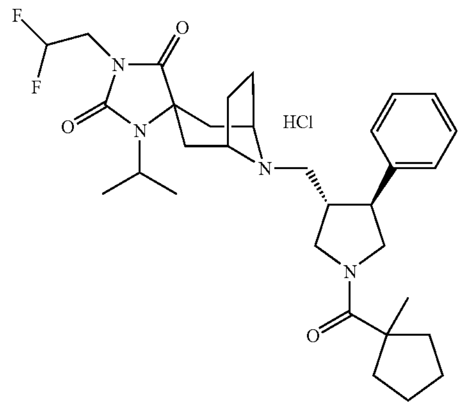 | (3S,4S)-1-(1-Methyl-cyclopentanecarbonyl)-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine hydrochloride | 607.19 |
| 78 | 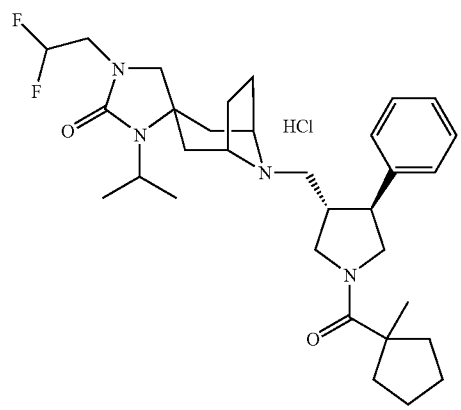 | (3S,4S)-1-(1-Methyl-cyclopentanecarbonyl)-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine hydrochloride | 593.21 |
| 79 | 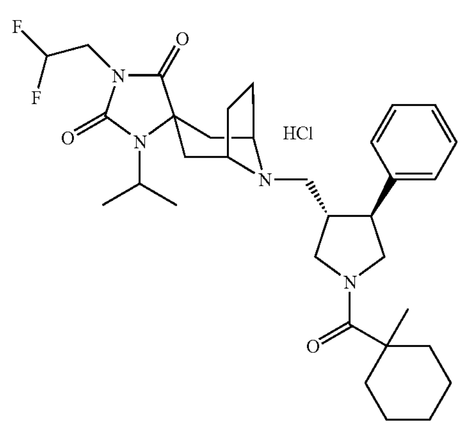 | (3S,4S)-1-(1-Methyl-cyclohexanecarbonyl)-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine hydrochloride | 621.22 |

| CPD # | STRUCTURE | COMPOUND NAME | MW |
|---|---|---|---|
| 80 | 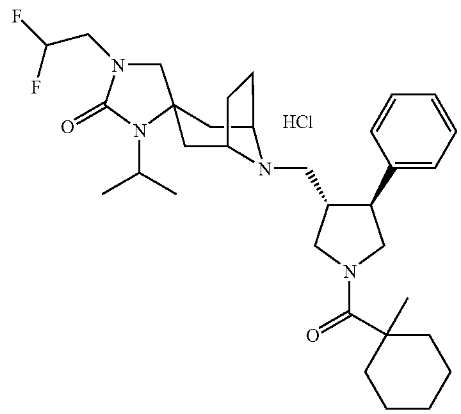 | (3S,4S)-1-(1-Methyl-cyclohexanecarbonyl)-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine hydrochloride | 607.23 |
| 81 | 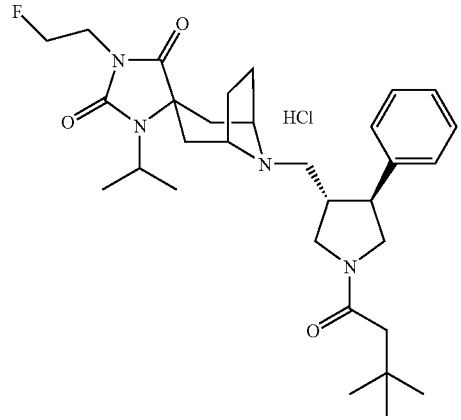 | (3S,4S)-1-(3,3-Dimethyl-butyryl)-3-[3-(2-fluoro-ethyl)-1-isopropyl-bicyclo[3.2.1]-2,4-dioxo-1β,3,8-triaza-spiro[4.5]dodec-8-ylmethyl]-4-phenyl-pyrrolidine hydrochloride | 577.19 |
| 82 | 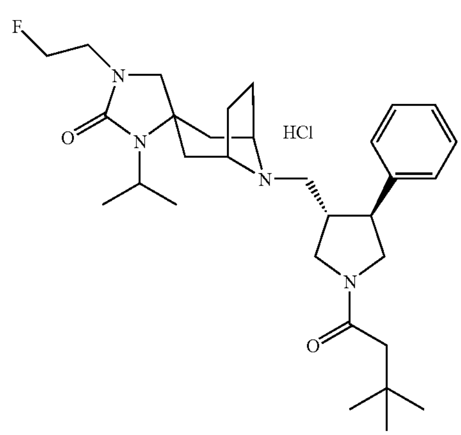 | (3S,4S)-1-(3,3-Dimethyl-butyryl)-3-[3-(2-fluoro-ethyl)-1-isopropyl-bicyclo[3.2.1]-2-oxo-1β,3,8-triaza-spiro[4.5]dodec-8-ylmethyl]-4-phenyl-pyrrolidine hydrochloride | 563.2 |

TABLE 4-continued

| CPD # | STRUCTURE | COMPOUND NAME | MW |
|---|---|---|---|
| 83 | 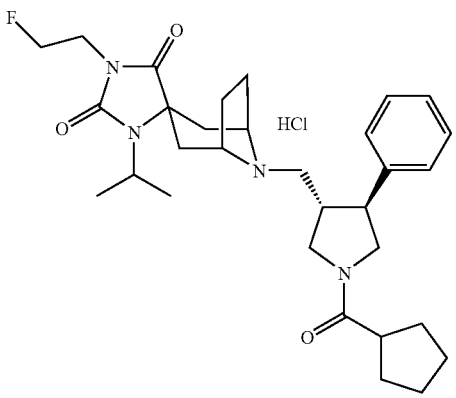 | (3S,4S)-1-Cyclopentanecarbonyl-3-[3-(2-fluoro-ethyl)-1-isopropyl-bicyclo[3.2.1]-2,4-dioxo-1β,3,8-triaza-spiro[4.5]dodec-8-ylmethyl]-4-phenyl-pyrrolidine hydrochloride | 575.17 |
| 84 | 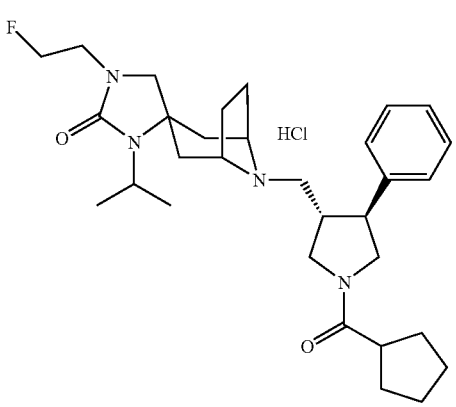 | (3S,4S)-1-Cyclopentanecarbonyl-3-[3-(2-fluoro-ethyl)-1-isopropyl-bicyclo[3.2.1]-2-oxo-1β,3,8-triaza-spiro[4.5]dodec-8-ylmethyl]-4-phenyl-pyrrolidine hydrochloride | 561.19 |
| 85 | 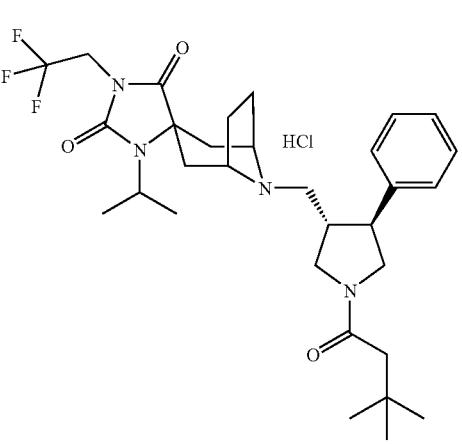 | (3S,4S)-1-(3,3-Dimethyl-butyryl)-3-[3-(2,2,2-trifluoro-ethyl)-1-isopropyl-bicyclo[3.2.1]-2,4-dioxo-1β,3,8-triaza-spiro[4.5]dodec-8-ylmethyl]-4-phenyl-pyrrolidine hydrochloride | 613.17 |

TABLE 4-continued

| CPD # | STRUCTURE | COMPOUND NAME | MW |
|---|---|---|---|
| 86 | 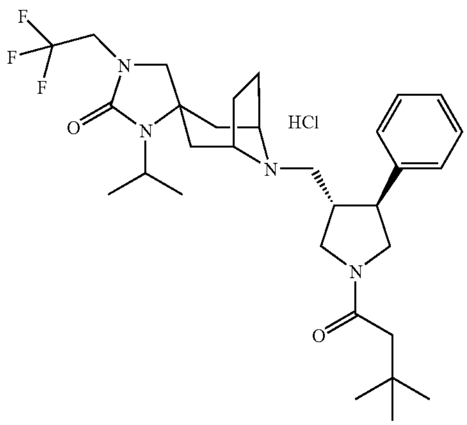 | (3S,4S)-1-(3,3-Dimethyl-butyryl)-3-[3-(2,2,2-trifluoro-ethyl)-1-isopropyl-bicyclo[3.2.1]-2-oxo-1β,3,8-triaza-spiro[4.5]dodec-8-ylmethyl]-4-phenyl-pyrrolidine hydrochloride | 599.19 |
| 87 | 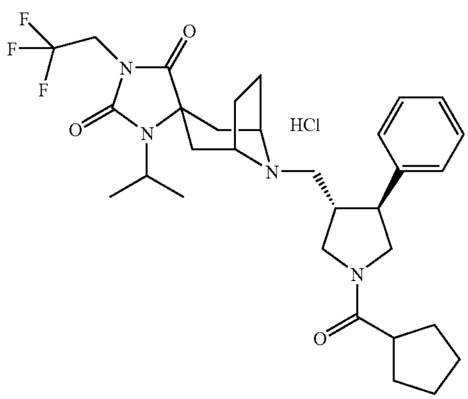 | (3S,4S)-1-Cyclopentanecarbonyl-3-[3-(2,2,2-trifluoro-ethyl)-1-isopropyl-bicyclo[3.2.1]-2,4-dioxo-1β,3,8-triaza-spiro[4.5]dodec-8-ylmethyl]-4-phenyl-pyrrolidine hydrochloride | 611.15 |
| 88 | 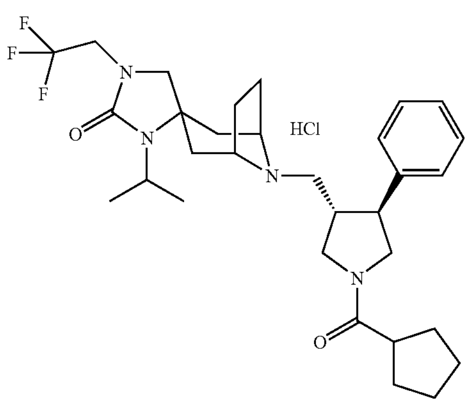 | (3S,4S)-1-Cyclopentanecarbonyl-3-[3-(2,2,2-trifluoro-ethyl)-1-isopropyl-bicyclo[3.2.1]-2-oxo-1β,3,8-triaza-spiro[4.5]dodec-8-ylmethyl]-4-phenyl-pyrrolidine hydrochloride | 597.17 |

| CPD # | STRUCTURE | COMPOUND NAME | MW |
|---|---|---|---|
| 89 | 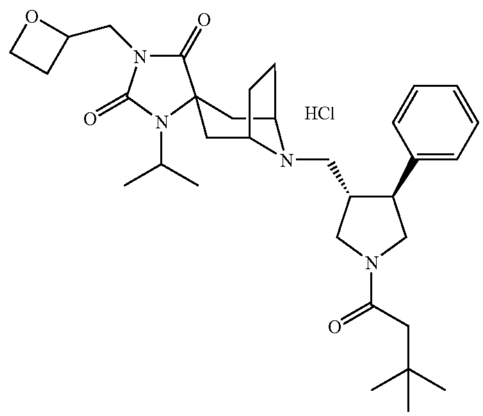 | (3S,4S)-1-(3,3-Dimethyl-butyryl)-3-[1-isopropyl-3-oxetan-2-ylmethyl-bicyclo[3.2.1]-2,4-dioxo-1β,3,8-triaza-spiro[4.5]dodec-8-ylmethyl]-4-phenyl-pyrrolidine hydrochloride | 601.23 |
| 90 | 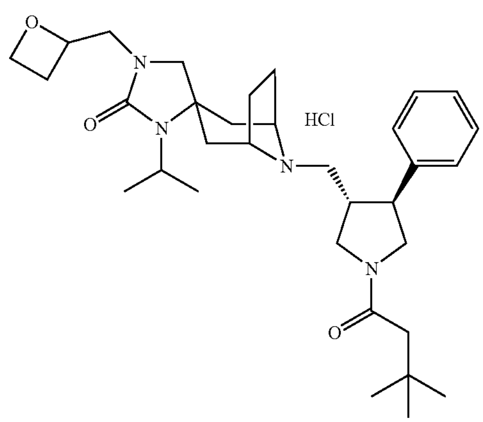 | (3S,4S)-1-(3,3-Dimethyl-butyryl)-3-[1-isopropyl-3-oxetan-2-ylmethyl-bicyclo[3.2.1]-2-oxo-1β,3,8-triaza-spiro[4.5]dodec-8-ylmethyl]-4-phenyl-pyrrolidine hydrochloride | 587.25 |
| 91 | 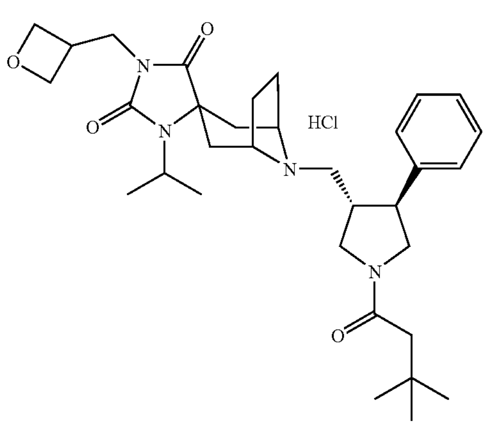 | (3S,4S)-1-(3,3-Dimethyl-butyryl)-3-[1-isopropyl-3-oxetan-3-ylmethyl-bicyclo[3.2.1]-2,4-dioxo-1β,3,8-triaza-spiro[4.5]dodec-8-ylmethyl]-4-phenyl-pyrrolidine hydrochloride | 601.23 |

TABLE 4-continued

| CPD # | STRUCTURE | COMPOUND NAME | MW |
|---|---|---|---|
| 92 | 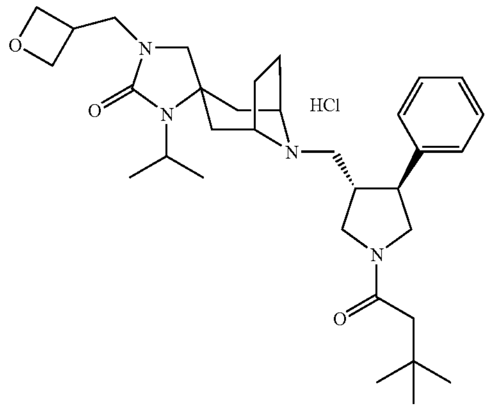 | (3S,4S)-1-(3,3-Dimethyl-butyryl)-3-[1-isopropyl-3-oxetan-3-ylmethyl-bicyclo[3.2.1]-2-oxo-1β,3,8-triaza-spiro[4.5]dodec-8-ylmethyl]-4-phenyl-pyrrolidine hydrochloride | 587.25 |
| 93 | 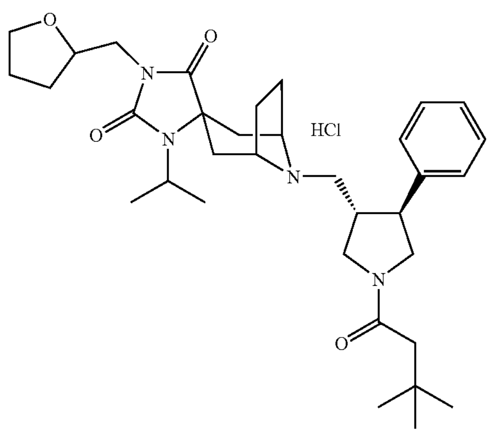 | (3S,4S)-1-(3,3-Dimethyl-butyryl)-3-[1-isopropyl-3-(tetrahydro-furan-2-ylmethyl)-bicyclo[3.2.1]-2,4-dioxo-1β,3,8-triaza-spiro[4.5]dodec-8-ylmethyl]-4-phenyl-pyrrolidine hydrochloride | 615.26 |
| 94 | 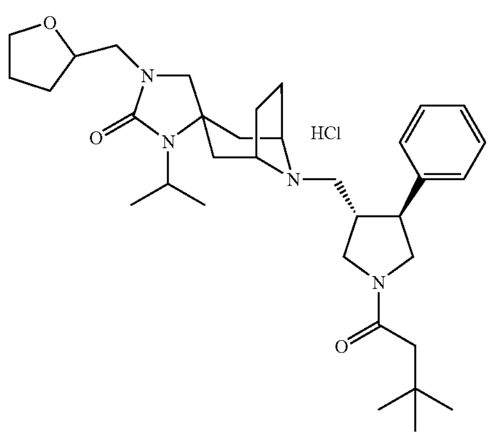 | (3S,4S)-1-(3,3-Dimethyl-butyryl)-3-[1-isopropyl-3-(tetrahydro-furan-2-ylmethyl)-bicyclo[3.2.1]-2-oxo-1β,3,8-triaza-spiro[4.5]dodec-8-ylmethyl]-4-phenyl-pyrrolidine hydrochloride | 601.28 |

TABLE 4-continued

| CPD # | STRUCTURE | COMPOUND NAME | MW |
|---|---|---|---|
| 95 | 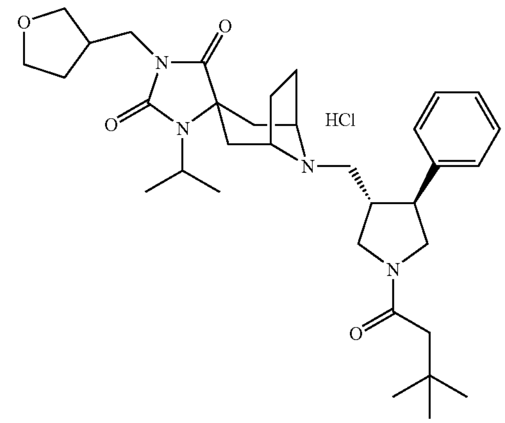 | (3S,4S)-1-(3,3-Dimethyl-butyryl)-3-[1-isopropyl-3-(tetrahydro-furan-3-ylmethyl)-bicyclo[3.2.1]-2,4-dioxo-1β,3,8-triaza-spiro[4.5]dodec-8-ylmethyl]-4-phenyl-pyrrolidine hydrochloride | 615.26 |
| 96 | 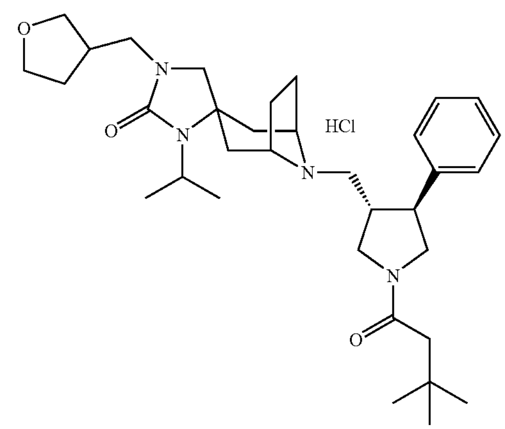 | (3S,4S)-1-(3,3-Dimethyl-butyryl)-3-[1-isopropyl-3-(tetrahydro-furan-3-ylmethyl)-bicyclo[3.2.1]-2-oxo-1β,3,8-triaza-spiro[4.5]dodec-8-ylmethyl]-4-phenyl-pyrrolidine hydrochloride | 601.28 |
| 97 | 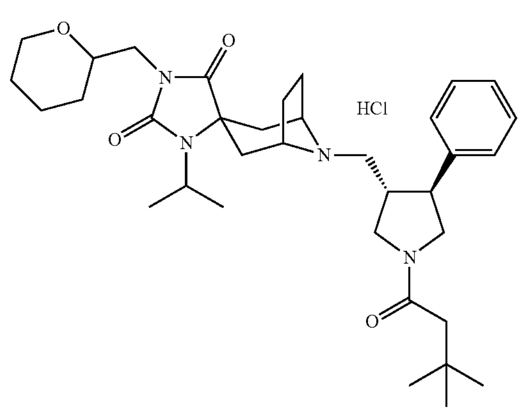 | (3S,4S)-1-(3,3-Dimethyl-butyryl)-3-[1-isopropyl-3-(tetrahydro-pyran-2-ylmethyl)-bicyclo[3.2.1]-2,4-dioxo-1β,3,8-triaza-spiro[4.5]dodec-8-ylmethyl]-4-phenyl-pyrrolidine hydrochloride | 629.29 |

| CPD # | STRUCTURE | COMPOUND NAME | MW |
|---|---|---|---|
| 98 | 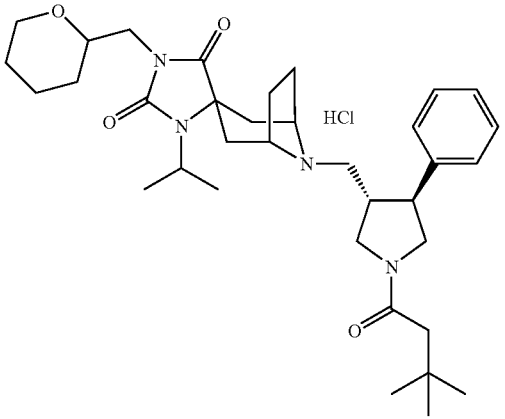 | (3S,4S)-1-(3,3-Dimethyl-butyryl)-3-[1-isopropyl-3-(tetrahydro-pyran-2-ylmethyl)-bicyclo[3.2.1]-2-oxo-1β,3,8-triaza-spiro[4.5]dodec-8-ylmethyl]-4-phenyl-pyrrolidine hydrochloride | 615.31 |
| 99 | 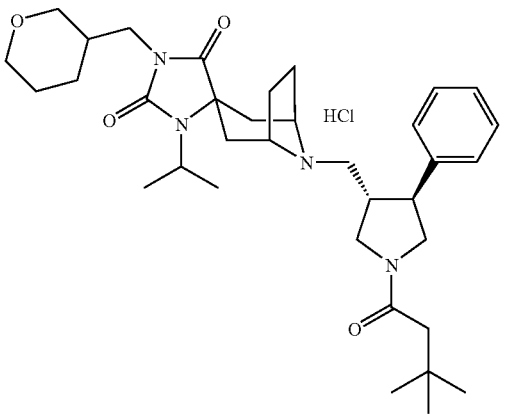 | (3S,4S)-1-(3,3-Dimethyl-butyryl)-3-[1-isopropyl-3-(tetrahydro-pyran-3-ylmethyl)-bicyclo[3.2.1]-2,4-dioxo-1β,3,8-triaza-spiro[4.5]dodec-8-ylmethyl]-4-phenyl-pyrrolidine hydrochloride | 629.29 |
| 100 | 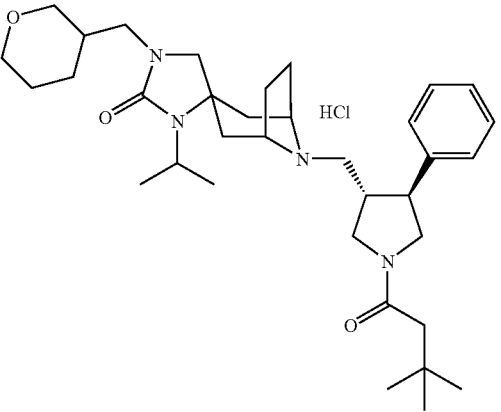 | (3S,4S)-1-(3,3-Dimethyl-butyryl)-3-[1-isopropyl-3-(tetrahydro-pyran-3-ylmethyl)-bicyclo[3.2.1]-2-oxo-1β,3,8-triaza-spiro[4.5]dodec-8-ylmethyl]-4-phenyl-pyrrolidine hydrochloride | 615.31 |

| CPD # | STRUCTURE | COMPOUND NAME | MW |
|---|---|---|---|
| 101 | 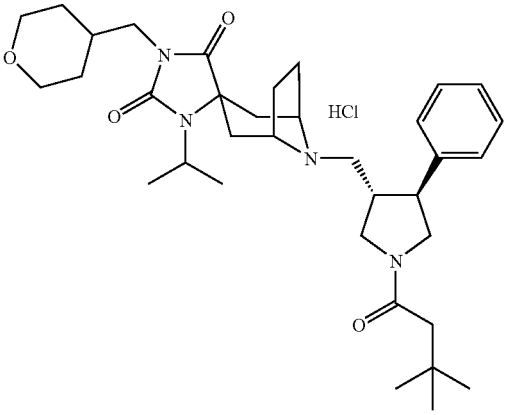 | (3S,4S)-1-(3,3-Dimethyl-butyryl)-3-[1-isopropyl-3-(tetrahydro-pyran-4-ylmethyl)-bicyclo[3.2.1]-2,4-dioxo-1β,3,8-triaza-spiro[4.5]dodec-8-ylmethyl]-4-phenyl-pyrrolidine hydrochloride | 629.29 |
| 102 | 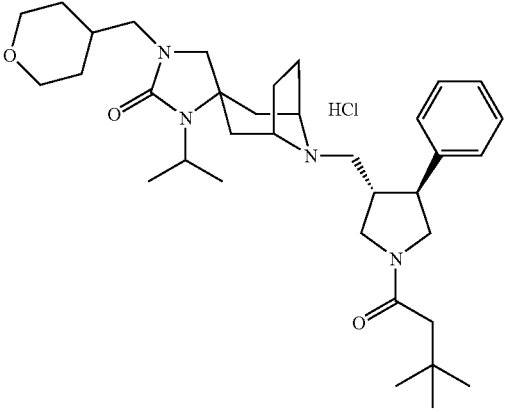 | (3S,4S)-1-(3,3-Dimethyl-butyryl)-3-[1-isopropyl-3-(tetrahydro-pyran-4-ylmethyl)-bicyclo[3.2.1]-2-oxo-1β,3,8-triaza-spiro[4.5]dodec-8-ylmethyl]-4-phenyl-pyrrolidine hydrochloride | 615.31 |
| 103 | 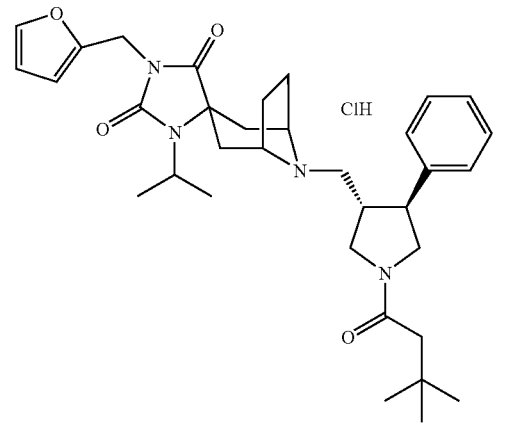 | (3S,4S)-1-(3,3-Dimethyl-butyryl)-3-[3-furan-2-ylmethyl-1-isopropyl-bicyclo[3.2.1]-2,4-dioxo-1β,3,8-triaza-spiro[4.5]dodec-8-ylmethyl]-4-phenyl-pyrrolidine hydrochloride | 611.23 |

TABLE 4-continued

| CPD # | STRUCTURE | COMPOUND NAME | MW |
|---|---|---|---|
| 104 | 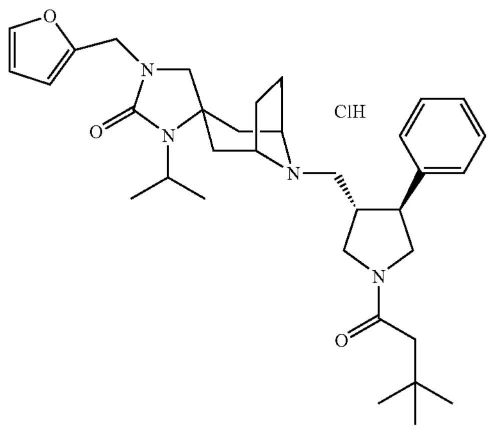 | (3S,4S)-1-(3,3-Dimethyl-butyryl)-3-[3-furan-2-ylmethyl-1-isopropyl-bicyclo[3.2.1]-2-oxo-1β,3,8-triaza-spiro[4.5]dodec-8-ylmethyl]-4-phenyl-pyrrolidine hydrochloride | 597.25 |
| 105 | 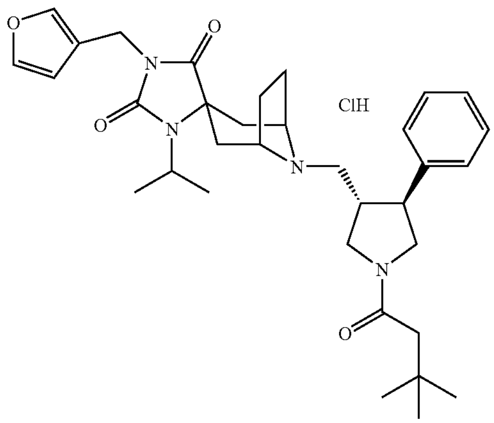 | (3S,4S)-1-(3,3-Dimethyl-butyryl)-3-[3-furan-2-ylmethyl-1-isopropyl-bicyclo[3.2.1]-2,4-dioxo-1β,3,8-triaza-spiro[4.5]dodec-8-ylmethyl]-4-phenyl-pyrrolidine hydrochloride | 611.23 |
| 106 | 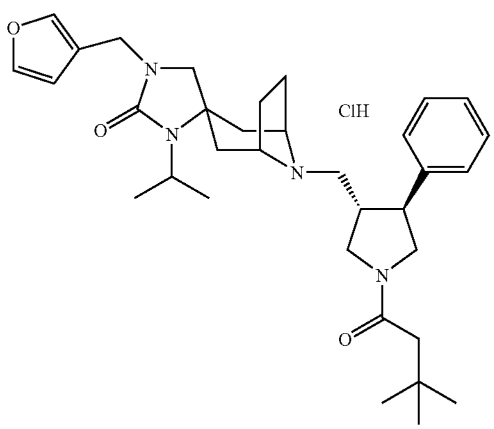 | (3S,4S)-1-(3,3-Dimethyl-butyryl)-3-[3-furan-3-ylmethyl-1-isopropyl-bicyclo[3.2.1]-2-oxo-1β,3,8-triaza-spiro[4.5]dodec-8-ylmethyl]-4-phenyl-pyrrolidine hydrochloride | 597.25 |

TABLE 4-continued

| CPD # | STRUCTURE | COMPOUND NAME | MW |
|---|---|---|---|
| 107 | 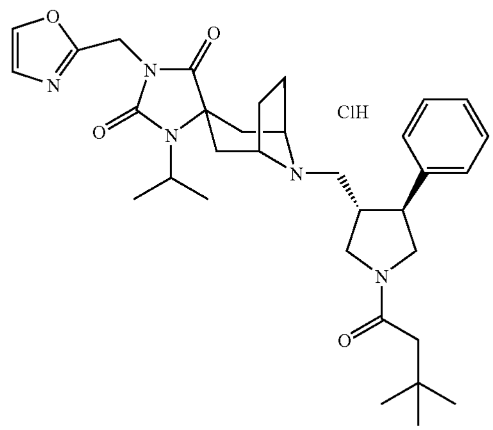 | (3S,4S)-1-(3,3-Dimethyl-butyryl)-3-[1-isopropyl-3-oxazol-2-ylmethyl-bicyclo[3.2.1]-2,4-dioxo-1β,3,8-triaza-spiro[4.5]dodec-8-ylmethyl]-4-phenyl-pyrrolidine hydrochloride | 612.22 |
| 108 | 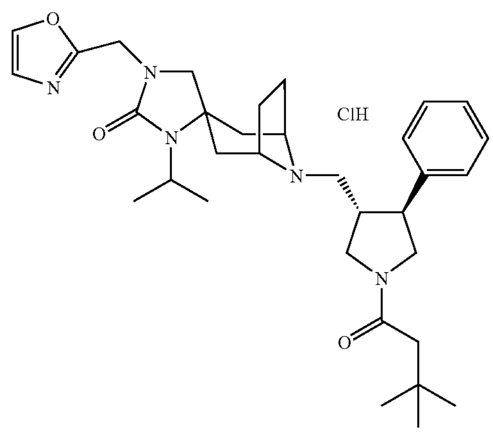 | (3S,4S)-1-(3,3-Dimethyl-butyryl)-3-[1-isopropyl-3-oxazol-2-ylmethyl-bicyclo[3.2.1]-2-oxo-1β,3,8-triaza-spiro[4.5]dodec-8-ylmethyl]-4-phenyl-pyrrolidine hydrochloride | 598.23 |
| 109 | 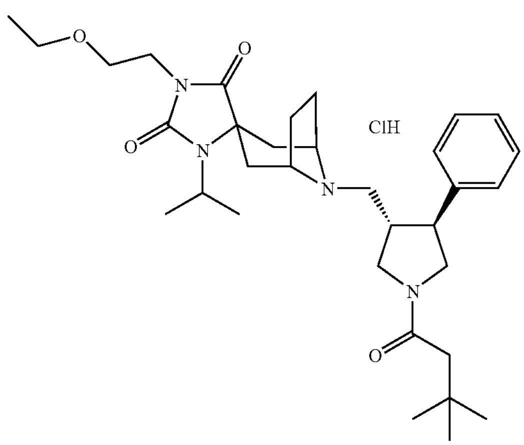 | (3S,4S)-1-(3,3-Dimethyl-butyryl)-3-[3-(2-ethoxy-ethyl)-1-isopropyl-bicyclo[3.2.1]-2,4-dioxo-1β,3,8-triaza-spiro[4.5]dodec-8-ylmethyl]-4-phenyl-pyrrolidine hydrochloride | 603.25 |

TABLE 4-continued

| CPD # | STRUCTURE | COMPOUND NAME | MW |
|---|---|---|---|
| 110 | 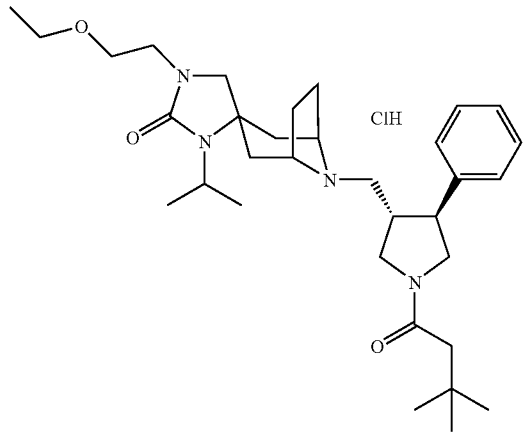 | (3S,4S)-1-(3,3-Dimethyl-butyryl)-3-[3-(2-ethoxy-ethyl)-1-isopropyl-bicyclo[3.2.1]-2-oxo-1β,3,8-triaza-spiro[4.5]dodec-8-ylmethyl]-4-phenyl-pyrrolidine hydrochloride | 589.27 |
| 111 | 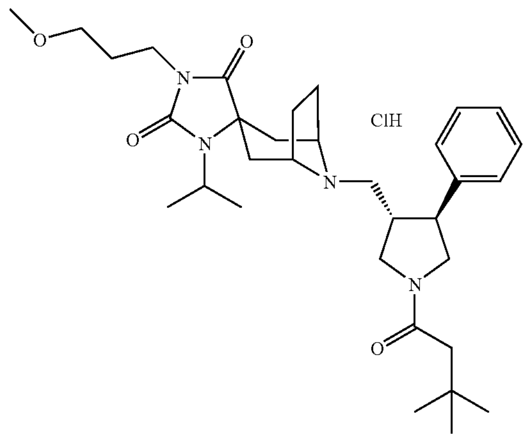 | (3S,4S)-1-(3,3-Dimethyl-butyryl)-3-[1-isopropyl-3-(2-methoxy-propyl)-bicyclo[3.2.1]-2,4-dioxo-1β,3,8-triaza-spiro[4.5]dodec-8-ylmethyl]-4-phenyl-pyrrolidine hydrochloride | 603.25 |
| 112 | 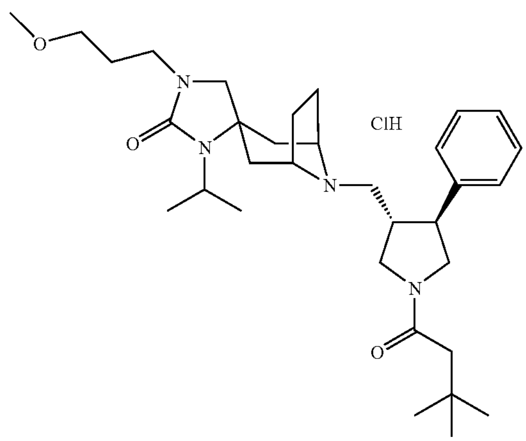 | (3S,4S)-1-(3,3-Dimethyl-butyryl)-3-[1-isopropyl-3-(2-methoxy-propyl)-bicyclo[3.2.1]-2-oxo-1β,3,8-triaza-spiro[4.5]dodec-8-ylmethyl]-4-phenyl-pyrrolidine hydrochloride | 589.27 |

Example 7

Chemokine Binding assay: Membranes (1 µg/well) from human embryonic kidney (HEK-293) cells expressing human CCR5 were incubated with 0.1 nM $^{125}$I-labeled MIP-1α (Amersham) in the presence of varying concentrations of a test compound (10000-0.01 nM) in buffer (50 mM Hepes, pH 7.3/5 mM MgCl$_2$/1 mM CaCl$_2$/0.5% BSA) for 90 min at room temperature. Reaction mixtures (100 µL) were filtered through Multiscreen GFB filters (Millipore) and washed six times with cold wash buffer (50 mM Hepes, pH 7.3/0.5 M NaCl, 0.1% BSA). Bound $^{125}$I-MIP-1α was quantitated by liquid scintillation counting. The nonspecific binding of $^{125}$I-labeled MIP-1α to the membrane was determined based on the radioactivity from the wells added with 100 nM non-radiolabeled MIP-1α. IC$_{50}$ and K$_D$ values were calculated by using GRAPHPAD PRISM software (Intuitive Software for Science, San Diego).

HIV-1 Replication in PBMC Cultures. Isolated PBMC were stimulated in vitro with 5 µg/ml phytohemagglutinin and 50 units/ml IL-2 for 3 days. The cells were resuspended at 4×10⁶/ml in complete medium (RPMI, 10% FBS/50 units/ml IL-2), seeded into 96-well plates (2×10⁵/well), incubated with inhibitor for 1 h at 37° C., and infected in triplicate with 25-100 tissue culture 50% infective dose ($TCID_{50}$) per well of the R5 HIV-1$_{JR-FL}$ strain for 3-4 h. The cells were washed twice in PBS to remove residual virus and cultured in the presence of inhibitor for 4-6 days. HIV-1 replication was determined by the presence of viral RT activity in harvested supernatant fluid. The $IC_{50}$ values for the virus were determined by using GRAPHPAD PRISM software.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound represented by formula (I):

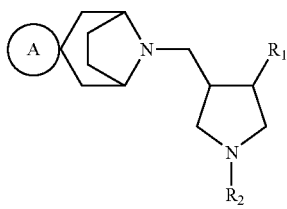

or pharmaceutically acceptable salts, hydrates or solvates thereof,
wherein

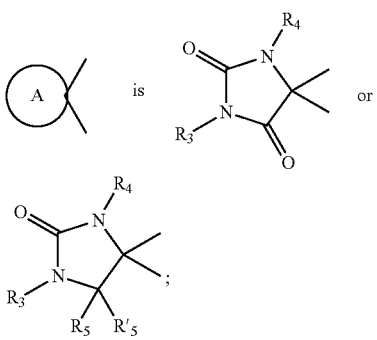

$R_1$ is unsubstituted phenyl or phenyl substituted with at least one substituent chosen from a halogen, $C_{1-6}$ alkyl, $C_{1-6}$alkyloxy, $CF_3$, COOH, $COOC_{1-6}$alkyl, cyano, $NH_2$, nitro, $NH(C_{1-6}$ alkyl), $N(C_{1-6}$ alkyl)$_2$ and a 3-8 member heterocycle;
$R_2$ is H,

or

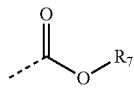

$R_3$ or $R_4$ are each independently methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which is unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino and guanido; wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle; or $R_3$ or $R_4$ are each independently oxetanyl, tetrahydropyranyl, tetrahydrofuranyl, morpholinyl, $CH_2$-oxetanyl, $CH_2$-tetrahydropyranyl, $CH_2$-tetrahydrofuranyl, any of which can be unsubstituted or substituted by one or more substituents chosen from halogen, $C_{1-6}$ alkyl, $NH_2$, nitro, $C(O)OC_{1-6}$ alkyl, COOH, $C_{1-6}$ alkyloxy, cyano, and azido; or $R_3$ or $R_4$ are each independently benzyl unsubstituted or substituted by one or more substituents chosen from halogen, $C_{1-3}$ alkoxy, $SO_2C_{1-3}$alkyl, difluoromethoxy, trifluoromethoxy, trifluoromethyl, CN and pyrazoyl;

$R_5$ and $R'_5$ are each H; and $R_7$ is methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl, any of which can be unsubstituted or substituted by one or more substituents chosen from halogen, nitro, nitroso, $SO_3R_{62}$, $PO_3R_{65}R_{66}$, $CONR_{63}R_{64}$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{7-12}$ aralkyl, 3-10 member heterocycle, 4-16 member heteroaralkyl, hydroxyl, oxo, oxime, $NR_{63}R_{64}$, $C(O)OR_{62}$, cyano, azido, amidino, and guanido; wherein $R_{62}$, $R_{65}$, $R_{66}$, $R_{63}$ and $R_{64}$ are each independently chosen from H, $C_{1-12}$ alkyl, $C_{2-12}$ alkenyl, $C_{2-12}$ alkynyl, $C_{6-12}$ aryl, 3-10 member heterocycle, 4-16 member heteroaralkyl, and $C_{7-18}$ aralkyl, or $R_{65}$ and $R_{66}$ are taken together with the oxygen atoms to form a 5 to 10 member heterocycle, or $R_{63}$ and $R_{64}$ are taken together with the nitrogen atom to form a 3 to 10 member heterocycle.

2. A compound represented by formula (Ia):

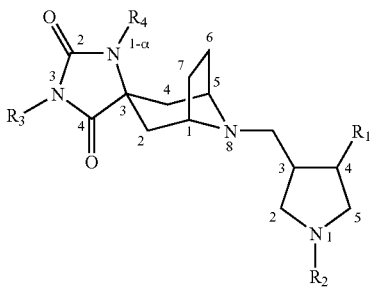

(Ia)

or pharmaceutically acceptable salts thereof wherein $R_1$, $R_2$, $R_3$ and $R_4$ are defined in claim 1.

3. A compound according to claim 1 wherein said compound is represented by formula (Ib):

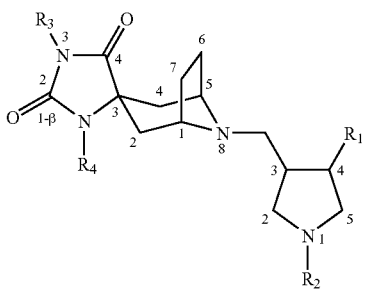

(Ib)

or pharmaceutically acceptable salts thereof wherein $R_1$, $R_2$, $R_3$ and $R_4$ are defined in claim 1.

4. A compound according to claim 1 wherein said compound is represented by formula (Ic):

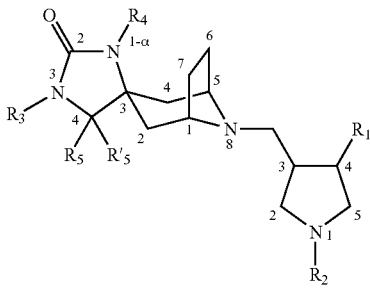

(Ic)

or pharmaceutically acceptable salts thereof wherein $R_1$, $R_2$, $R_3$, $R_4$, $R_5$ and $R'_5$ are defined in claim 1.

5. A compound according to claim 1 wherein said compound is represented by formula (Id):

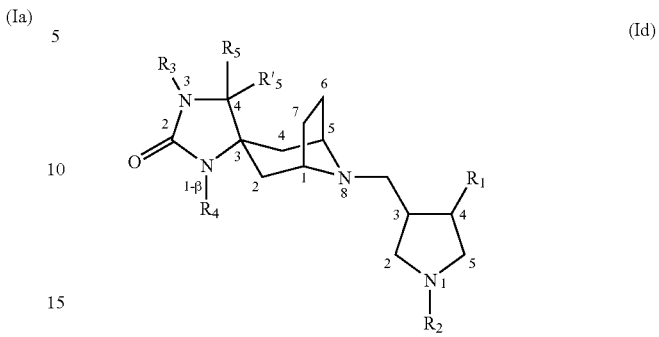

(Id)

or pharmaceutically acceptable salts thereof wherein $R_1$, $R_2$, $R_3$, $R_4$, $R_5$ and $R'_5$ are defined in claim 1.

6. The compound as defined in claim 1 wherein said compound is in the form of the (3R,4R)-diastereomer.

7. The compound as defined in claim 1 wherein said compound is in the form of the (3S,4R)-diastereomer.

8. The compound as defined in claim 1 wherein said compound is in the form of the (3R,4S)-diastereomer.

9. The compound as defined in claim 1 wherein said compound is in the form of the (3S,4S)-diastereomer.

10. The compound of claim 1 wherein $R_7$ is chosen from optionally substituted methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl.

11. The compound of claim 1 wherein $R_7$ is an optionally substituted cyclohexyl, cyclopentyl or cyclobutyl.

12. The compound according to claim 1 wherein $R_3$ or $R_4$ are independently an optionally substituted $CH_2$-oxetanyl, $CH_2$-tetrahydropyranyl, $CH_2$-tetrahydrofuranyl.

13. The compound according to claim 1 wherein $R_3$ or $R_4$ are independently chosen from an optionally substituted methyl, ethyl, vinyl, propyl, propenyl, isopropyl, butyl, isobutyl, pentyl, neopentyl, tert-butyl, cyclopropyl, cyclobutyl, cyclopentyl, cyclohexyl, or cycloheptyl.

14. The compound according to claim 1 wherein $R_3$ or $R_4$ are independently chosen from methyl, ethyl, vinyl, propyl, propenyl, isopropyl, butyl, isobutyl, pentyl, neopentyl, or tert-butyl.

15. The compound according to claim 1 wherein $R_3$ or $R_4$ are independently unsubstituted methyl or methyl substituted by one or more halogens.

16. The compound according to claim 1 wherein $R_3$ or $R_4$ are independently unsubstituted methyl or methyl substituted by one or more fluoro.

17. The compound according to claim 1 wherein $R_3$ or $R_4$ are independently isopropyl or isobutyl.

18. A compound selected from

| | |
|---|---|
| 1 | (3S,4S)-3-[3-(4-Methanesulfonylbenzyl)-bicyclo[3.2.1]-2,4-dioxo-1α,3,8-triaza-spiro[4.5]dodec-8-ylmethyl]-4-phenyl-pyrrolidine-1-carboxylic acid tert-butyl ester; |
| 2 | (3S,4S)-3-[1-Isopropyl-3-methyl-bicyclo[3.2.1]-2,4-dioxo-1β,3,8-triaza-spiro[4.5]dodec-8-ylmethyl]-4-phenyl-pyrrolidine-1-carboxylic acid tert-butyl ester; |

| | |
|---|---|
| 3 | (3S,4S)-3-[3-Ethyl-1-isopropyl-bicyclo[3.2.1]-2,4-dioxo-1β,3,8-triaza-spiro[4.5]dodec-8-ylmethyl]-4-phenyl-pyrrolidine-1-carboxylic acid tert-butyl ester; |
| 4 | (3S,4S)-3-[1-Isopropyl-3-(2-methoxy-ethyl)-bicyclo[3.2.1]-2,4-dioxo-1β,3,8-triaza-spiro[4.5]dodec-8-ylmethyl]-4-phenyl-pyrrolidine-1-carboxylic acid tert-butyl ester; |
| 5 | (3S,4S)-3-[1-Isopropyl-3-(tetrahydrofuran-3-yl)-bicyclo[3.2.1]-2,4-dioxo-1β,3,8-triaza-spiro[4.5]dodec-8-ylmethyl]-4-phenyl-pyrrolidine-1-carboxylic acid tert-butyl ester; |
| 6 | (3S,4S)-3-[1-Isopropyl-3-(tetrahydropyran-4-yl)-bicyclo[3.2.1]-2,4-dioxo-1β,3,8-triaza-spiro[4.5]dodec-8-ylmethyl]-4-phenyl-pyrrolidine-1-carboxylic acid tert-butyl ester; |
| 7 | (3S,4S)-3-[1-Isopropyl-3-methyl-bicyclo[3.2.1]-2-oxo-1β,3,8-triaza-spiro[4.5]dodec-8-ylmethyl]-4-phenyl-pyrrolidine-1-carboxylic acid tert-butyl ester; |
| 8 | (3S,4S)-3-[3-Ethyl-1-isopropyl-bicyclo[3.2.1]-2-oxo-1β,3,8-triaza-spiro[4.5]dodec-8-ylmethyl]-4-phenyl-pyrrolidine-1-carboxylic acid tert-butyl ester; |
| 9 | (3S,4S)-1-benzyl-3-[3-(2,2-Difluoro-ethyl)-1-isopropyl-bicyclo[3.2.1]-2,4-dioxo-1β,3,8-triaza-spiro[4.5]dodec-8-ylmethyl]-4-phenyl-pyrrolidine; |
| 10 | (3S,4S)-3-[3-(2,2-Difluoro-ethyl)-1-isopropyl-bicyclo[3.2.1]-2-oxo-1β,3,8-triaza-spiro[4.5]dodec-8-ylmethyl]-4-phenyl-pyrrolidine-1-carboxylic acid tert-butyl ester; |
| 11 | (3S,4S)-3-[1-Isopropyl-3-(2-methoxy-ethyl)-bicyclo[3.2.1]-2-oxo-1β,3,8-triaza-spiro[4.5]dodec-8-ylmethyl]-4-phenyl-pyrrolidine-1-carboxylic acid tert-butyl ester |
| 12 | (3S,4S)-3-[1-Isopropyl-3-(tetrahydrofuran-3-yl)-bicyclo[3.2.1]-2-oxo-1β,3,8-triaza-spiro[4.5]dodec-8-ylmethyl]-4-phenyl-pyrrolidine-1-carboxylic acid tert-butyl ester |
| 13 | (3S,4S)-3-[1-Isopropyl-3-(tetrahydropyran-4-yl)-bicyclo[3.2.1]-2-oxo-1β,3,8-triaza-spiro[4.5]dodec-8-ylmethyl]-4-phenyl-pyrrolidine-1-carboxylic acid tert-butyl ester; |
| 14 | (3R,4S)-3-[1-Isopropyl-3-methyl-bicyclo[3.2.1]-2,4-dioxo-1β,3,8-triaza-spiro[4.5]dodec-8-ylmethyl]-4-phenyl-pyrrolidine; |
| 15 | (3R,4S)-3-[3-Ethyl-1-isopropyl-bicyclo[3.2.1]-2,4-dioxo-1β,3,8-triaza-spiro[4.5]dodec-8-ylmethyl]-4-phenyl-pyrrolidine; |
| 16 | (3R,4S)-3-[3-(2,2-Difluoro-ethyl)-1-isopropyl-bicyclo[3.2.1]-2,4-dioxo-1β,3,8-triaza-spiro[4.5]dodec-8-ylmethyl]-4-phenyl-pyrrolidine; |
| 17 | (3R,4S)-3-[1-Isopropyl-3-(2-methoxy-ethyl)-bicyclo[3.2.1]-2,4-dioxo-1β,3,8-triaza-spiro[4.5]dodec-8-ylmethyl]-4-phenyl-pyrrolidine; |
| 18 | (3R,4S)-3-[1-Isopropyl-3-(tetrahydrofuran-3-yl)-bicyclo[3.2.1]-2,4-dioxo-1β,3,8-triaza-spiro[4.5]dodec-8-ylmethyl]-4-phenyl-pyrrolidine; |
| 19 | (3R,4S)-3-[1-Isopropyl-3-(tetrahydropyran-4-yl)-bicyclo[3.2.1]-2,4-dioxo-1β,3,8-triaza-spiro[4.5]dodec-8-ylmethyl]-4-phenyl-pyrrolidine; |
| 20 | (3R,4S)-3-[1-Isopropyl-3-methyl-bicyclo[3.2.1]-2-oxo-1β,3,8-triaza-spiro[4.5]dodec-8-ylmethyl]-4-phenyl-pyrrolidine; |
| 21 | (3R,4S)-3-[3-Ethyl-1-isopropyl-bicyclo[3.2.1]-2-oxo-1β,3,8-triaza-spiro[4.5]dodec-8-ylmethyl]-4-phenyl-pyrrolidine; |
| 22 | (3R,4S)-3-[3-(2,2-Difluoro-ethyl)-1-isopropyl-bicyclo[3.2.1]-2-oxo-1β,3,8-triaza-spiro[4.5]dodec-8-ylmethyl]-4-phenyl-pyrrolidine; |
| 23 | (3R,4S)-3-[1-Isopropyl-3-(2-methoxy-ethyl)-bicyclo[3.2.1]-2-oxo-1β,3,8-triaza-spiro[4.5]dodec-8-ylmethyl]-4-phenyl-pyrrolidine; |
| 24 | (3R,4S)-3-[1-Isopropyl-3-(tetrahydrofuran-3-yl)-bicyclo[3.2.1]-2-oxo-1β,3,8-triaza-spiro[4.5]dodec-8-ylmethyl]-4-phenyl-pyrrolidine; |
| 25 | (3R,4S)-3-[1-Isopropyl-3-(tetrahydropyran-4-yl)-bicyclo[3.2.1]-2-oxo-1β,3,8-triaza-spiro[4.5]dodec-8-ylmethyl]-4-phenyl-pyrrolidine; |
| 26 | (3S,4S)-1-Cyclopentanecarbonyl-3-[1-isopropyl-3-methyl-bicyclo[3.2.1]-2,4-dioxo-1β,3,8-triaza-spiro[4.5]dodec-8-ylmethyl]-4-phenyl-pyrrolidine; |
| 27 | (3S,4S)-1-(1-Trifluoromethyl-cyclobutanecarbonyl)-3-[1-isopropyl-3-methyl-bicyclo[3.2.1]-2,4-dioxo-1β,3,8-triaza-spiro[4.5]dodec-8-ylmethyl]-4-phenyl-pyrrolidine; |
| 28 | (3S,4S)-1-Cyclopentanecarbonyl-3-[3-ethyl-1-isopropyl-bicyclo[3.2.1]-2,4-dioxo-1β,3,8-triaza-spiro[4.5]dodec-8-ylmethyl]-4-phenyl-pyrrolidine; |
| 29 | (3S,4S)-1-(3,3-Dimethyl-butyryl)-3-[3-ethyl-1-isopropyl-bicyclo[3.2.1]-2,4-dioxo-1β,3,8-triaza-spiro[4.5]dodec-8-ylmethyl]-4-phenyl-pyrrolidine; |
| 30 | (3S,4S)-1-(1-Trifluoromethyl-cyclobutanecarbonyl)-3-[3-ethyl-1-isopropyl-bicyclo[3.2.1]-2,4-dioxo-1β,3,8-triaza-spiro[4.5]dodec-8-ylmethyl]-4-phenyl-pyrrolidine; |
| 31 | (3S,4S)-1-Cyclopentanecarbonyl-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine; |
| 32 | (3S,4S)-1-(3,3-Dimethyl-butyryl)-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine; |
| 33 | (3S,4S)-1-Cyclopentanecarbonyl-3-[-1-isopropyl-3-(2-methoxy-ethyl)-bicyclo[3.2.1]-2,4-dioxo-1β,3,8-triaza-spiro[4.5]dodec-8-ylmethyl]-4-phenyl-pyrrolidine; |
| 34 | (3S,4S)-1-(3,3-Dimethyl-butyryl)-3-[1-isopropyl-3-(2-methoxy-ethyl)-bicyclo[3.2.1]-2,4-dioxo-1β,3,8-triaza-spiro[4.5]dodec-8-ylmethyl]-4-phenyl-pyrrolidine; |
| 35 | (3S,4S)-1-(3,3-Dimethyl-butyryl)-3-[1-isopropyl-3-(tetrahydro-furan-3-yl)-bicyclo[3.2.1]-2,4-dioxo-1β,3,8-triaza-spiro[4.5]dodec-8-ylmethyl]-4-phenyl-pyrrolidine; |
| 36 | (3S,4S)-1-(3,3-Dimethyl-butyryl)-3-[1-isopropyl-3-(tetrahydro-pyran-4-yl)-bicyclo[3.2.1]-2,4-dioxo-1β,3,8-triaza-spiro[4.5]docdec-8-ylmethyl]-4-phenyl-pyrrolidine; |
| 37 | (3S,4S)-1-Cyclopentanecarbonyl-3-[1-isopropyl-3-methyl-bicyclo[3.2.1]-2-oxo-1β,3,8-triaza-spiro[4.5]dodec-8-ylmethyl]-4-phenyl-pyrrolidine |
| 38 | (3S,4S)-1-(3,3-Dimethyl-butyryl)-3-[1-isopropyl-3-methyl-bicyclo[3.2.1]-2-oxo-1β,3,8-triaza-spiro[4.5]dodec-8-ylmethyl]-4-phenyl-pyrrolidine; |
| 39 | (3S,4S)-1-(1-Trifluoromethyl-cyclobutanecarbonyl)-3-[1-isopropyl-3-methyl-bicyclo[3.2.1]-2-oxo-1β,3,8-triaza-spiro[4.5]dodec-8-ylmethyl]-4-phenyl-pyrrolidine; |
| 40 | (3S,4S)-1-(2-Cyclopropyl-acetyl)-3-[1-isopropyl-3-methyl-bicyclo[3.2.1]-2-oxo-1β,3,8-triaza-spiro[4.5]dodec-8-ylmethyl]-4-phenyl-pyrrolidine; |
| 41 | (3S,4S)-1-(3-Methyl-butyryl)-3-[1-isopropyl-3-methyl-bicyclo[3.2.1]-2-oxo-1β,3,8-triaza-spiro[4.5]dodec-8-ylmethyl]-4-phenyl-pyrrolidine; |
| 42 | (3S,4S)-1-Cyclopentanecarbonyl-3-[3-ethyl-1-isopropyl-bicyclo[3.2.1]-2-oxo-1β,3,8-triaza-spiro[4.5]dodec-8-ylmethyl]-4-phenyl-pyrrolidine; |
| 43 | (3S,4S)-1-(3,3-Dimethyl-butyryl)-3-[3-ethyl-1-isopropyl-bicyclo[3.2.1]-2-oxo-1β,3,8-triaza-spiro[4.5]dodec-8-ylmethyl]-4-phenyl-pyrrolidine; |
| 44 | (3S,4S)-1-(1-Trifluoromethyl-cyclobutanecarbonyl)-3-[3-ethyl-1-isopropyl-bicyclo[3.2.1]-2-oxo-1β,3,8-triaza-spiro[4.5]dodec-8-ylmethyl]-4-phenyl-pyrrolidine; |
| 45 | (3S,4S)-1-(3,3-Dimethyl-butyryl)-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine; |
| 46 | (3S,4S)-1-Cyclopentanecarbonyl-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine; |
| 47 | (3S,4S)-1-Cyclopentanecarbonyl-3-[-1-isopropyl-3-(2-methoxy-ethyl)-bicyclo[3.2.1]-2-oxo-1β,3,8-triaza-spiro[4.5]dodec-8-ylmethyl]-4-phenyl-pyrrolidine; |
| 48 | (3S,4S)-1-(3,3-Dimethyl-butyryl)-3-[1-isopropyl-3-(2-methoxy-ethyl)-bicyclo[3.2.1]-2-oxo-1β,3,8-triaza-spiro[4.5]dodec-8-ylmethyl]-4-phenyl-pyrrolidine; |
| 49 | (3S,4S)-1-(3,3-Dimethyl-butyryl)-3-[1-isobutyl-3-(2-methoxy-ethyl)-bicyclo[3.2.1]-2-oxo-1β,3,8-triaza-spiro[4.5]dodec-8-ylmethyl]-4-phenyl-pyrrolidine; |

| | |
|---|---|
| 50 | (3S,4S)-1-Cyclopentanecarbonyl-3-[-1-isopropyl-3-(tetrahydro-furan-3-yl)-bicyclo[3.2.1]-2-oxo-1β,3,8-triaza-spiro[4.5]dodec-8-ylmethyl]-4-phenyl-pyrrolidine; |
| 51 | (3S,4S)-1-(3,3-Dimethyl-butyryl)-3-[1-isopropyl-3-(tetrahydro-furan-3-yl)-bicyclo[3.2.1]-2-oxo-1β,3,8-triaza-spiro[4.5]dodec-8-ylmethyl]-4-phenyl-pyrrolidine; |
| 52 | (3S,4S)-1-Cyclopentanecarbonyl-3-[-1-isopropyl-3-(tetrahydro-pyran-4-yl)-bicyclo[3.2.1]-2-oxo-1β,3,8-triaza-spiro[4.5]dodec-8-ylmethyl]-4-phenyl-pyrrolidine; |
| 53 | (3S,4S)-1-(3,3-Dimethyl-butyryl)-3-[1-isopropyl-3-(tetrahydro-pyran-4-yl)-bicyclo[3.2.1]-2-oxo-1β,3,8-triaza-spiro[4.5]dodec-8-ylmethyl]-4-phenyl-pyrrolidine; |
| 54 | (3S,4S)-1-(4,4-Difluoro-cyclohexanecarbonyl)-3-[3-(4-N,N-dimethyl-benzenesulfonamide)-bicyclo[3.2.1]-2,4-dioxo-1α,3,8-triaza-spiro[4.5]dodec-8-ylmethyl]-4-phenyl-pyrrolidine; |
| 55 | (3S,4S)-1-(3,3-Dimethyl-butyryl)-3-[1-isobutyl-3-methyl-bicyclo[3.2.1]-2,4-dioxo-1β,3,8-triaza-spiro[4.5]dodec-8-ylmethyl]-4-phenyl-pyrrolidine; |
| 56 | (3S,4S)-1-(3,3-Dimethyl-butyryl)-3-[1-cyclopropylmethyl-3-methyl-bicyclo[3.2.1]-2,4-dioxo-1β,3,8-triaza-spiro[4.5]dodec-8-ylmethyl]-4-phenyl-pyrrolidine; |
| 57 | (3S,4S)-1-(4,4-Difluoro-cyclohexanecarbonyl)-3-[1,3-diethyl-bicyclo[3.2.1]-2,4-dioxo-1β,3,8-triaza-spiro[4.5]dodec-8-ylmethyl]-4-phenyl-pyrrolidine; |
| 58 | (3S,4S)-1-(3,3-Dimethyl-butyryl)-3-[3-ethyl-1-isobutyl-bicyclo[3.2.1]-2,4-dioxo-1β,3,8-triaza-spiro[4.5]dodec-8-ylmethyl]-4-phenyl-pyrrolidine; |
| 59 | (3S,4S)-1-(3,3-Dimethyl-butyryl)-3-[1-isopropyl-3-methyl-bicyclo[3.2.1]-2,4-dioxo-1β,3,8-triaza-spiro[4.5]dodec-8-ylmethyl]-4-phenyl-pyrrolidine; |
| 60 | (3S,4S)-1-(3,3-Dimethyl-butyryl)-3-[1-cyclopropylmethyl-3-methyl-bicyclo[3.2.1]-2-oxo-1β,3,8-triaza-spiro[4.5]dodec-8-ylmethyl]-4-phenyl-pyrrolidine; |
| 61 | (3S,4S)-1-(3,3-Dimethyl-butyryl)-3-[1-isopropyl-3-methyl-bicyclo[3.2.1]-2,4-dioxo-1β,3,8-triaza-spiro[4.5]dodec-8-ylmethyl]-4-(3-fluorophenyl)-pyrrolidine; |
| 62 | (3S,4S)-1-(3,3-Dimethyl-butyryl)-3-[1-isopropyl-3-methyl-bicyclo[3.2.1]-2-oxo-1β,3,8-triaza-spiro[4.5]dodec-8-ylmethyl]-4-(3-fluorophenyl)-pyrrolidine; |
| 63 | (3S,4S)-1-Cyclopentanecarbonyl-3-[1-isopropyl-3-methyl-bicyclo[3.2.1]-2,4-dioxo-1β,3,8-triaza-spiro[4.5]dodec-8-ylmethyl]-4-(3-fluorophenyl)-pyrrolidine; |
| 64 | (3S,4S)-1-Cyclopentanecarbonyl-3-[1-isopropyl-3-methyl-bicyclo[3.2.1]-2-oxo-1β,3,8-triaza-spiro[4.5]dodec-8-ylmethyl]-4-(3-fluorophenyl)-pyrrolidine; |
| 65 | (3S,4S)-1-Cyclobutanecarbonyl-3-[1-isopropyl-3-methyl-bicyclo[3.2.1]-2,4-dioxo-1β,3,8-triaza-spiro[4.5]dodec-8-ylmethyl]-4-phenyl-pyrrolidine; |
| 66 | (3S,4S)-1-Cyclobutanecarbonyl-3-[1-isopropyl-3-methyl-bicyclo[3.2.1]-2-oxo-1β,3,8-triaza-spiro[4.5]dodec-8-ylmethyl]-4-phenyl-pyrrolidine; |
| 67 | (3S,4S)-1-(1-Methyl-cyclobutanecarbonyl)-3-[1-isopropyl-3-methyl-bicyclo[3.2.1]-2,4-dioxo-1β,3,8-triaza-spiro[4.5]dodec-8-ylmethyl]-4-phenyl-pyrrolidine; |
| 68 | (3S,4S)-1-(1-Methyl-cyclobutanecarbonyl)-3-[1-isopropyl-3-methyl-bicyclo[3.2.1]-2-oxo-1β,3,8-triaza-spiro[4.5]dodec-8-ylmethyl]-4-phenyl-pyrrolidine; |
| 69 | (3S,4S)-1-(1-Methyl-cyclopentanecarbonyl)-3-[1-isopropyl-3-methyl-bicyclo[3.2.1]-2,4-dioxo-1β,3,8-triaza-spiro[4.5]dodec-8-ylmethyl]-4-phenyl-pyrrolidine; |
| 70 | (3S,4S)-1-(1-Methyl-cyclopentanecarbonyl)-3-[1-isopropyl-3-methyl-bicyclo[3.2.1]-2-oxo-1β,3,8-triaza-spiro[4.5]dodec-8-ylmethyl]-4-phenyl-pyrrolidine; |
| 71 | (3S,4S)-1-(1-Methyl-cyclohexanecarbonyl)-3-[1-isopropyl-3-methyl-bicyclo[3.2.1]-2,4-dioxo-1β,3,8-triaza-spiro[4.5]dodec-8-ylmethyl]-4-phenyl-pyrrolidine; |
| 72 | (3S,4S)-1-(1-Methyl-cyclohexanecarbonyl)-3-[1-isopropyl-3-methyl-bicyclo[3.2.1]-2-oxo-1β,3,8-triaza-spiro[4.5]dodec-8-ylmethyl]-4-phenyl-pyrrolidine; |
| 73 | (3S,4S)-1-Cyclobutanecarbonyl-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine; |
| 74 | (3S,4S)-1-Cyclobutanecarbonyl-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine; |
| 75 | (3S,4S)-1-(1-Methyl-cyclobutanecarbonyl)-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine; |
| 76 | (3S,4S)-1-(1-Methyl-cyclobutanecarbonyl)-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine; |
| 77 | (3S,4S)-1-(1-Methyl-cyclopentanecarbonyl)-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine; |
| 78 | (3S,4S)-1-(1-Methyl-cyclopentanecarbonyl)-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine; |
| 79 | (3S,4S)-1-(1-Methyl-cyclohexanecarbonyl)-3-[3-(2,2-difluoro-ethyl)-1-isopropyl-bicyclo[3.2.1]-2,4-dioxo-1β,3,8-triaza-spiro[4.5]dodec-8-ylmethyl]-4-phenyl-pyrrolidine; |
| 80 | (3S,4S)-1-(1-Methyl-cyclohexanecarbonyl)-3-[3-(2,2-difluoro-ethyl)-1-isopropyl-bicyclo[3.2.1]-2-oxo-1β,3,8-triaza-spiro[4.5]dodec-8-ylmethyl]-4-phenyl-pyrrolidine; |
| 81 | (3S,4S)-1-(3,3-Dimethyl-butyryl)-3-[3-(2-fluoro-ethyl)-1-isopropyl-bicyclo[3.2.1]-2,4-dioxo-1β,3,8-triaza-spiro[4.5]dodec-8-ylmethyl]-4-phenyl-pyrrolidine; |
| 82 | (3S,4S)-1-(3,3-Dimethyl-butyryl)-3-[3-(2-fluoro-ethyl)-1-isopropyl-bicyclo[3.2.1]-2-oxo-1β,3,8-triaza-spiro[4.5]dodec-8-ylmethyl]-4-phenyl-pyrrolidine; |
| 83 | (3S,4S)-1-Cyclopentanecarbonyl-3-[3-(2-fluoro-ethyl)-1-isopropyl-bicyclo[3.2.1]-2,4-dioxo-1β,3,8-triaza-spiro[4.5]dodec-8-ylmethyl]-4-phenyl-pyrrolidine; |
| 84 | (3S,4S)-1-Cyclopentanecarbonyl-3-[3-(2-fluoro-ethyl)-1-isopropyl-bicyclo[3.2.1]-2-oxo-1β,3,8-triaza-spiro[4.5]dodec-8-ylmethyl]-4-phenyl-pyrrolidine; |
| 85 | (3S,4S)-1-(3,3-Dimethyl-butyryl)-3-[3-(2,2,2-trifluoro-ethyl)-1-isopropyl-bicyclo[3.2.1]-2,4-dioxo-1β,3,8-triaza-spiro[4.5]dodec-8-ylmethyl]-4-phenyl-pyrrolidine; |
| 86 | (3S,4S)-1-(3,3-Dimethyl-butyryl)-3-[3-(2,2,2-trifluoro-ethyl)-1-isopropyl-bicyclo[3.2.1]-2-oxo-1β,3,8-triaza-spiro[4.5]dodec-8-ylmethyl]-4-phenyl-pyrrolidine; |
| 87 | (3S,4S)-1-Cyclopentanecarbonyl-3-[3-(2,2,2-trifluoro-ethyl)-1-isopropyl-bicyclo[3.2.1]-2,4-dioxo-1β,3,8-triaza-spiro[4.5]dodec-8-ylmethyl]-4-phenyl-pyrrolidine; |
| 88 | (3S,4S)-1-Cyclopentanecarbonyl-3-[3-(2,2,2-trifluoro-ethyl)-1-isopropyl-bicyclo[3.2.1]-2-oxo-1β,3,8-triaza-spiro[4.5]dodec-8-ylmethyl]-4-phenyl-pyrrolidine; |
| 89 | (3S,4S)-1-(3,3-Dimethyl-butyryl)-3-[1-isopropyl-3-oxetan-2-ylmethyl-bicyclo[3.2.1]-2,4-dioxo-1β,3,8-triaza-spiro[4.5]dodec-8-ylmethyl]-4-phenyl-pyrrolidine; |
| 90 | (3S,4S)-1-(3,3-Dimethyl-butyryl)-3-[1-isopropyl-3-oxetan-2-ylmethyl-bicyclo[3.2.1]-2-oxo-1β,3,8-triaza-spiro[4.5]dodec-8-ylmethyl]-4-phenyl-pyrrolidine; |
| 91 | (3S,4S)-1-(3,3-Dimethyl-butyryl)-3-[1-isopropyl-3-oxetan-3-ylmethyl-bicyclo[3.2.1]-2,4-dioxo-1β,3,8-triaza-spiro[4.5]dodec-8-ylmethyl]-4-phenyl-pyrrolidine; |
| 92 | (3S,4S)-1-(3,3-Dimethyl-butyryl)-3-[1-isopropyl-3-oxetan-3-ylmethyl-bicyclo[3.2.1]-2-oxo-1β,3,8-triaza-spiro[4.5]dodec-8-ylmethyl]-4-phenyl-pyrrolidine; |
| 93 | (3S,4S)-1-(3,3-Dimethyl-butyryl)-3-[1-isopropyl-3-(tetrahydro-furan-2-ylmethyl)-bicyclo[3.2.1]-2,4-dioxo-1β,3,8-triaza-spiro[4.5]dodec-8-ylmethyl]-4-phenyl-pyrrolidine; |

| | |
|---|---|
| 94 | (3S,4S)-1-(3,3-Dimethyl-butyryl)-3-[1-isopropyl-3-(tetrahydro-furan-2-ylmethyl)-bicyclo[3.2.1]-2-oxo-1β,3,8-triaza-spiro[4.5]dodec-8-ylmethyl]-4-phenyl-pyrrolidine; |
| 95 | (3S,4S)-1-(3,3-Dimethyl-butyryl)-3-[1-isopropyl-3-(tetrahydro-furan-3-ylmethyl)-bicyclo[3.2.1]-2,4-dioxo-1β,3,8-triaza-spiro[4.5]dodec-8-ylmethyl]-4-phenyl-pyrrolidine; |
| 96 | (3S,4S)-1-(3,3-Dimethyl-butyryl)-3-[1-isopropyl-3-(tetrahydro-furan-3-ylmethyl)-bicyclo[3.2.1]-2-oxo-1β,3,8-triaza-spiro[4.5]dodec-8-ylmethyl]-4-phenyl-pyrrolidine; |
| 97 | (3S,4S)-1-(3,3-Dimethyl-butyryl)-3-[1-isopropyl-3-(tetrahydro-pyran-2-ylmethyl)-bicyclo[3.2.1]-2,4-dioxo-1β,3,8-triaza-spiro[4.5]dodec-8-ylmethyl]-4-phenyl-pyrrolidine; |
| 98 | (3S,4S)-1-(3,3-Dimethyl-butyryl)-3-[1-isopropyl-3-(tetrahydro-pyran-2-ylmethyl)-bicyclo[3.2.1]-2-oxo-1β,3,8-triaza-spiro[4.5]dodec-8-ylmethyl]-4-phenyl-pyrrolidine; |
| 99 | (3S,4S)-1-(3,3-Dimethyl-butyryl)-3-[1-isopropyl-3-(tetrahydro-pyran-3-ylmethyl)-bicyclo[3.2.1]-2,4-dioxo-1β,3,8-triaza-spiro[4.5]dodec-8-ylmethyl]-4-phenyl-pyrrolidine; |
| 100 | (3S,4S)-1-(3,3-Dimethyl-butyryl)-3-[1-isopropyl-3-(tetrahydro-pyran-3-ylmethyl)-bicyclo[3.2.1]-2-oxo-1β,3,8-triaza-spiro[4.5]dodec-8-ylmethyl]-4-phenyl-pyrrolidine; |
| 101 | (3S,4S)-1-(3,3-Dimethyl-butyryl)-3-[1-isopropyl-3-(tetrahydro-pyran-4-ylmethyl)-bicyclo[3.2.1]-2,4-dioxo-1β,3,8-triaza-spiro[4.5]dodec-8-ylmethyl]-4-phenyl-pyrrolidine; |
| 102 | (3S,4S)-1-(3,3-Dimethyl-butyryl)-3-[1-isopropyl-3-(tetrahydro-pyran-4-ylmethyl)-bicyclo[3.2.1]-2-oxo-1β,3,8-triaza-spiro[4.5]dodec-8-ylmethyl]-4-phenyl-pyrrolidine; |
| 103 | (3S,4S)-1-(3,3-Dimethyl-butyryl)-3-[3-furan-2-ylmethyl-1-isopropyl-bicyclo[3.2.1]-2,4-dioxo-1β,3,8-triaza-spiro[4.5]dodec-8-ylmethyl]-4-phenyl-pyrrolidine; |
| 104 | (3S,4S)-1-(3,3-Dimethyl-butyryl)-3-[3-furan-2-ylmethyl-1-isopropyl-bicyclo[3.2.1]-2-oxo-1β,3,8-triaza-spiro[4.5]dodec-8-ylmethyl]-4-phenyl-pyrrolidine; |
| 105 | (3S,4S)-1-(3,3-Dimethyl-butyryl)-3-[3-furan-3-ylmethyl-1-isopropyl-bicyclo[3.2.1]-2,4-dioxo-1β,3,8-triaza-spiro[4.5]dodec-8-ylmethyl]-4-phenyl-pyrrolidine; |
| 106 | (3S,4S)-1-(3,3-Dimethyl-butyryl)-3-[3-furan-3-ylmethyl-1-isopropyl-bicyclo[3.2.1]-2-oxo-1β,3,8-triaza-spiro[4.5]dodec-8-ylmethyl]-4-phenyl-pyrrolidine; |
| 107 | (3S,4S)-1-(3,3-Dimethyl-butyryl)-3-[1-isopropyl-3-oxazol-2-ylmethyl-bicyclo[3.2.1]-2,4-dioxo-1β,3,8-triaza-spiro[4.5]dodec-8-ylmethyl]-4-phenyl-pyrrolidine; |
| 108 | (3S,4S)-1-(3,3-Dimethyl-butyryl)-3-[1-isopropyl-3-oxazol-2-ylmethyl-bicyclo[3.2.1]-2-oxo-1β,3,8-triaza-spiro[4.5]dodec-8-ylmethyl]-4-phenyl-pyrrolidine; |
| 109 | (3S,4S)-1-(3,3-Dimethyl-butyryl)-3-[3-(2-ethoxy-ethyl)-1-isopropyl-bicyclo[3.2.1]-2,4-dioxo-1β,3,8-triaza-spiro[4.5]dodec-8-ylmethyl]-4-phenyl-pyrrolidine; |
| 110 | (3S,4S)-1-(3,3-Dimethyl-butyryl)-3-[3-(2-ethoxy-ethyl)-1-isopropyl-bicyclo[3.2.1]-2-oxo-1β,3,8-triaza-spiro[4.5]dodec-8-ylmethyl]-4-phenyl-pyrrolidine; |
| 111 | (3S,4S)-1-(3,3-Dimethyl-butyryl)-3-[1-isopropyl-3-(2-methoxy-propyl)-bicyclo[3.2.1]-2,4-dioxo-1β,3,8-triaza-spiro[4.5]dodec-8-ylmethyl]-4-phenyl-pyrrolidine; |
| 112 | (3S,4S)-1-(3,3-Dimethyl-butyryl)-3-[1-isopropyl-3-(2-methoxy-propyl)-bicyclo[3.2.1]-2-oxo-1β,3,8-triaza-spiro[4.5]dodec-8-ylmethyl]-4-phenyl-pyrrolidine; | or pharmaceutically acceptable salts thereof.

19. A pharmaceutical formulation comprising a compound according to claim 1 in combination with a pharmaceutically acceptable carrier or excipient.

* * * * *